(12) United States Patent
Sullenger et al.

(10) Patent No.: US 12,312,588 B2
(45) Date of Patent: May 27, 2025

(54) NUCLEOLIN-TARGETING APTAMERS AND METHODS OF USING THE SAME

(71) Applicant: Duke University, Durham, NC (US)

(72) Inventors: Bruce A. Sullenger, Durham, NC (US); Michael Goldstein, Durham, NC (US); Elizabeth D. Pratico, Durham, NC (US); Michael Kastan, Durham, NC (US); Bethany Gray, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 18/205,390

(22) Filed: Jun. 2, 2023

(65) Prior Publication Data
US 2024/0150772 A1 May 9, 2024

Related U.S. Application Data

(62) Division of application No. 16/645,762, filed as application No. PCT/US2018/050240 on Sep. 10, 2018, now Pat. No. 11,713,464.

(60) Provisional application No. 62/555,745, filed on Sep. 8, 2017.

(51) Int. Cl.
C12N 15/115 (2010.01)
A61P 35/00 (2006.01)
C12Q 1/68 (2018.01)

(52) U.S. Cl.
CPC ............ C12N 15/115 (2013.01); A61P 35/00 (2018.01); C12N 2310/16 (2013.01)

(58) Field of Classification Search
None
See application file for complete search history.

(56) References Cited

U.S. PATENT DOCUMENTS

| | | | |
|---|---|---|---|
| 7,396,664 B2 | 7/2008 | Daly et al. | |
| RE43,612 E | 8/2012 | Anderson et al. | |
| 9,150,867 B2 | 10/2015 | Maher, III et al. | |
| 9,340,591 B2 | 5/2016 | Sullenger et al. | |
| 10,533,059 B2 | 1/2020 | Sengupta et al. | |
| 10,683,506 B2 | 6/2020 | Zu | |
| 2003/0083294 A1 | 5/2003 | Sullenger et al. | |
| 2006/0105975 A1 | 5/2006 | Pendergast et al. | |
| 2008/0207546 A1 | 8/2008 | Sullenger | |
| 2009/0304717 A1 | 12/2009 | Barth et al. | |
| 2010/0184822 A1 | 7/2010 | Sullenger et al. | |
| 2010/0249217 A1 | 9/2010 | Sullenger et al. | |
| 2011/0178161 A1 | 7/2011 | Trent et al. | |
| 2011/0197292 A1 | 8/2011 | Sullenger | |
| 2012/0183564 A1 | 7/2012 | Sullenger | |
| 2013/0115254 A1 | 5/2013 | Odom | |
| 2014/0213636 A1 | 7/2014 | Lee et al. | |
| 2014/0348755 A1 | 11/2014 | Weng | |
| 2015/0203848 A1 | 7/2015 | Yu et al. | |
| 2015/0276750 A1 | 10/2015 | Zu | |
| 2015/0307883 A1 | 10/2015 | Yarden | |
| 2017/0165376 A9 | 6/2017 | Rich | |
| 2018/0117182 A1 | 5/2018 | Sullenger et al. | |
| 2019/0359983 A1 | 11/2019 | O'Neill et al. | |
| 2020/0095636 A1 | 3/2020 | Sullenger | |
| 2020/0283773 A1 | 9/2020 | Sullenger | |

FOREIGN PATENT DOCUMENTS

| | | |
|---|---|---|
| EP | 1800695 | 6/2007 |
| WO | 2002026932 | 4/2002 |
| WO | 2004081021 | 9/2004 |
| WO | 2007071777 | 6/2007 |
| WO | 2009045545 | 4/2009 |
| WO | 2014121256 | 7/2014 |
| WO | 2014/169049 | 10/2014 |

OTHER PUBLICATIONS

Allerson, C. R. et al. "Fully 2'-Modified Oligonucleotide Duplexes with Improved in Vitro Potency and Stability Compared to Unmodified Small Interfering RNA." J. Med. Chem 48 (2005): 901-904.
Bates P Jet Al: "Discovery and development of the G-rich oligonucleotide AS1411 as a novel treatment for cancer", Experimental and Molecular Pathology, Academic Press, US, vol. 86, No. 3, Jun. 1, 2009 (Jun. 1, 2009), pp. 151-164.
Becker et al., "Nucleic acid aptamers in therapeutic anticoagulation. Technology, development and clinical application," (2005) Thromb. Haemost. 93:1014-1020.
Berenbaum et al., "Synergy, additivism and antagonism in immunosuppression. A critical review," (1977) Clin Exp Immunol 28: 1-18.
Champlin, R. E. et al. T-cell depletion of bone marrow transplants for leukemia from donors other than HLA-identical siblings: advantage of T-cell antibodies with narrow specificities. Blood. 2000;95: 3996-4003.
Chen et al., "Cell surface nucleolin serves as receptor for DNA nanoparticles composed of pegylated polylysine and DNA," (2008) Mol. Ther. 16(2):333-42—Abstract.
Cheng, Y, et al. "AS-1411, a guanosine-rich oligonucleotide aptamer targeting nucleolin for the potential treatment of cancer, including acute myeloid leukemia", Current Opinion in Molecular Therapeutics, Current Drugs, London, GB, vol. 12, No. 1, Jan. 31, 2010 (Jan. 31, 2010), pp. 107-114.
Chu et al., "Aptamer mediated siRNA delivery," (2006) Nucleic Acids Research 34(10):e73.
Conrad, R.C. et al. "[20] In vitro selection of nucleic acid aptamers that bind proteins." Methods in enzymology 267 (1996): 336-367.
Dyke et al., "First-in-human experience of an antidote-controlled anticoagulant using RNA aptamer technology: a phase 1a pharmacodynamic evaluation of a drug-antidote pair for the controlled regulation of factor IXa activity," (2006) Circulation 114:2490-2497.
Ellington et al., "In vitro selection of RNA molecules that bind specific ligands." (1990) Nature 346:818-22.

(Continued)

Primary Examiner — Sean McGarry
(74) Attorney, Agent, or Firm — Quarles & Brady, LLP

(57) ABSTRACT

Provided herein are compositions including aptamers capable of binding to and/or inhibiting the activity of nucleolin. Methods of treating cancer in a subject by administering such compositions are also provided.

19 Claims, 46 Drawing Sheets
Specification includes a Sequence Listing.

(56) References Cited

OTHER PUBLICATIONS

Extended European Search Report for European Patent Application No. 18853636.1, dated Nov. 10, 2021.
Farokhzad et al., "Nanoparticle aptamer bioconjugates: A new approach for targeting prostate cancer cells," (2004) Cancer Research 64:7668-7672.
Gen Bank CR446327, CR 446327 XGC-tailbud Xenopus tropicalis cDNA clone TTbA054d215-mRNA sequence. GenBank Accession No. CR446327. Jun. 19, 2004. Retrieved from teh internent: URL:https://.ncbi.nlm.nih.gov/nucest/CR446327.
Goldstein, Michael, et al. "Nucleolin mediates nucleosome disruption critical for DNA double-strand break repair." Proceedings of the National Academy of Sciences 110.42 (2013): 16874-16879.
International Search Report and Written Opinion for application PCT/US2018/050240.Mailed on Jan. 29, 2019 (17 pages).
James et al., "A molecular imaging primer: modalities, imaging agents, and applications," (2012) Physiol Rev 92 (2):897-965.
Keefe, A. D., et al. (2010). Aptamers as therapeutics. Nature reviews Drug discovery, 9(7), 537-550.
Khaled et al., "Controllable self-assembly of nanoparticles for specific delivery of multiple therapeutic molecules to cancer cells using RNA nanotechnology," (2005) Nano Letters 5(9):1797-1808.
Labib, M. et al "Aptamer and Antisense-Mediated Two-Dimensional Isolation of Specific Cancer Cell Subpopulations" J. Am. Chem. Soc. 2016 138:2476-2479.
Lai, Y.-T., et al. "A primer-free method that selects high-affinity single-stranded DNA aptamers using thermostable RNA ligase." Analytical biochemistry 414.2 (2011): 246-253.
Li, F. et al. "A water-soluble nucleolin aptamer-paclitaxel conjugate for tumor-specific targeting in ovarian cancer", Nature Communications, vol. 8, No. 1, Nov. 9, 2017.
Li, N., et al. "Inhibition of cell proliferation by an anti-EGFR aptamer." PloS one 6.6 (2011): e20299.
Lupold et al., "Identification and characterization of nuclease-stabilized RNA molecules that bind human prostate cancer cells via the prostate-specific membrane antigen," (2002) Cancer Research 62:4029-4033.
Nimjee et al., "Aptamers as Therapeutics," (2017) Annual review of pharmacology and toxicology 57:61-79.
Nimjee et al., "Aptamers: an emerging class of therapeutics," (2005) Annual review of medicine 56:555-83.
Office Action for U.S. Appl. No. 16/645,762 dated Jun. 13, 2022.
Osbourne. S.E. et al. "Nucleic acid selection and the challenge of combinatorial chemistry." Chemical reviews 97.2 (1997): 349-370.
Que-Gewirth, N.S. et al., "Gene therapy progress and prospects: RNA aptamers," (2007) Gene Therapy 14 (4):283-291.
Ray, P. et al. "Aptamer-mediated delivery of chemotherapy to pancreatic cancer cells." Nucleic acid therapeutics 22.5 (2012): 295-305.
Restriction Requirement for U.S. Appl. No. 16/645,762, mailed Dec. 3, 2021.
Reyes-Reyes, E. Merit, et al. "Mechanistic studies of anticancer aptamer AS1411 reveal a novel role for nucleolin in regulating Rac1 activation." Molecular oncology 9.7 (2015): 1392-1405.
Schlessinger, J. "Autoinhibition control." Science 300.5620 (2003): 750-752.
Tuerk et al., "Systematic evolution of ligands by exponential enrichment: RNA ligands to bacteriophage T4 DNA polymerase," (1990) Science 249:505-10.
White, R. et al., "Generation of Species Cross-reactive Aptamers Using Toggle SELEX," (2001) Molecular Therapy 4 (6):567-573.
White, R. R. et al., "Developing aptamers into therapeutics," (2000) J. Clin. Investigation 106(8):929-934.

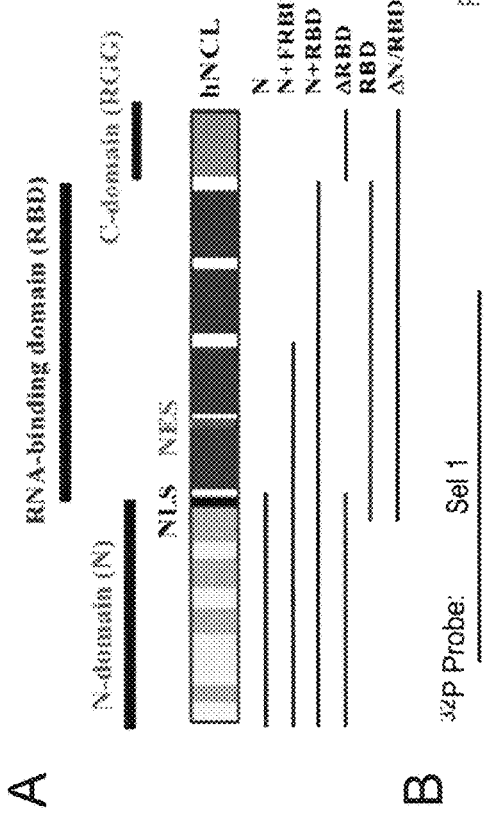
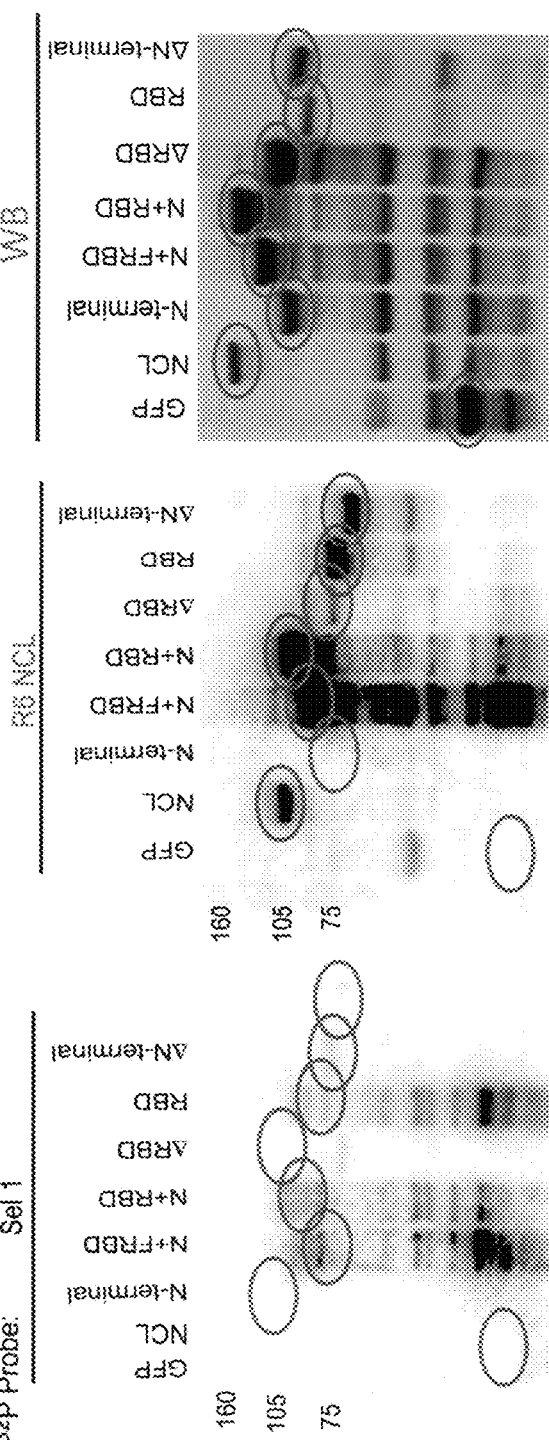
FIG. 3A
FIG. 3B

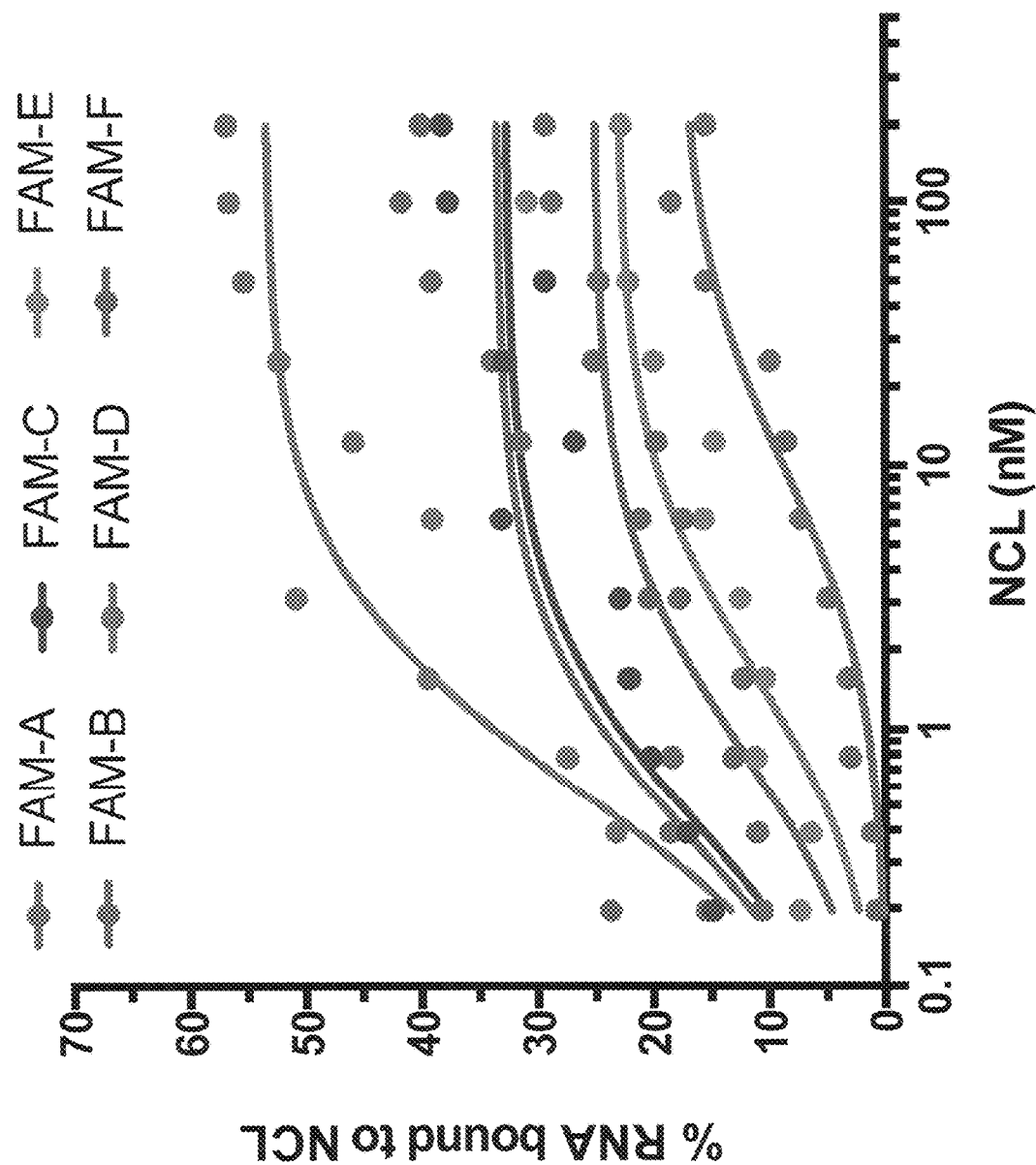

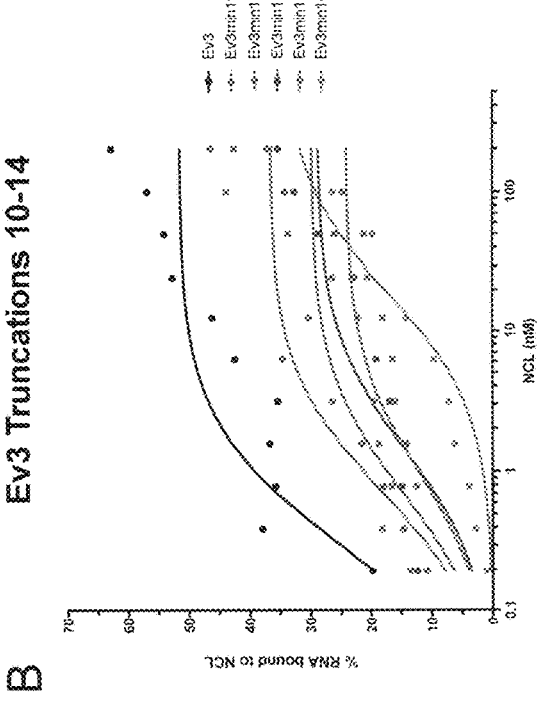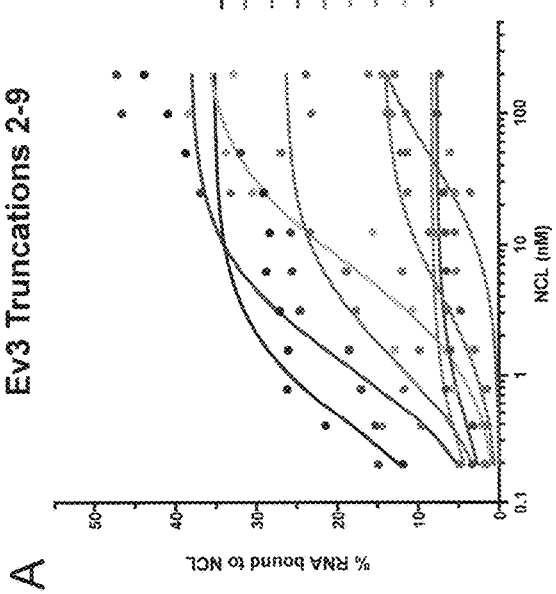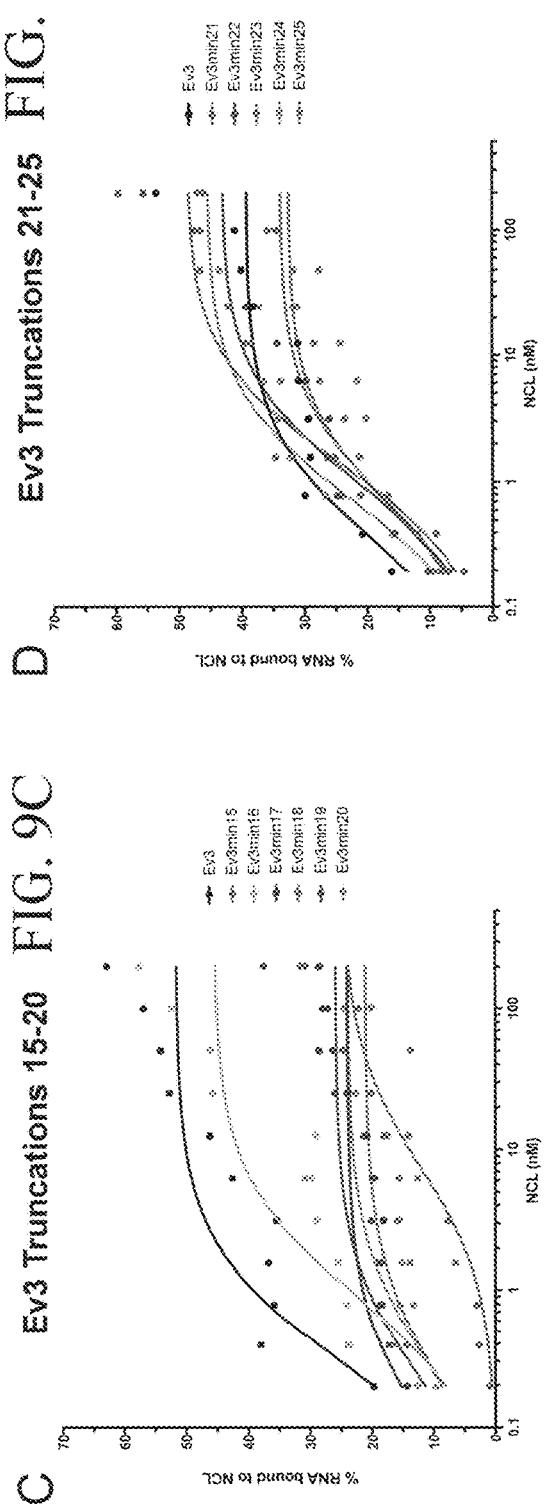
FIG. 9A Ev3 Truncations 2-9
FIG. 9B Ev3 Truncations 10-14
FIG. 9C Ev3 Truncations 15-20
FIG. 9D Ev3 Truncations 21-25

FIG. 11A
Family B (FAM-B)
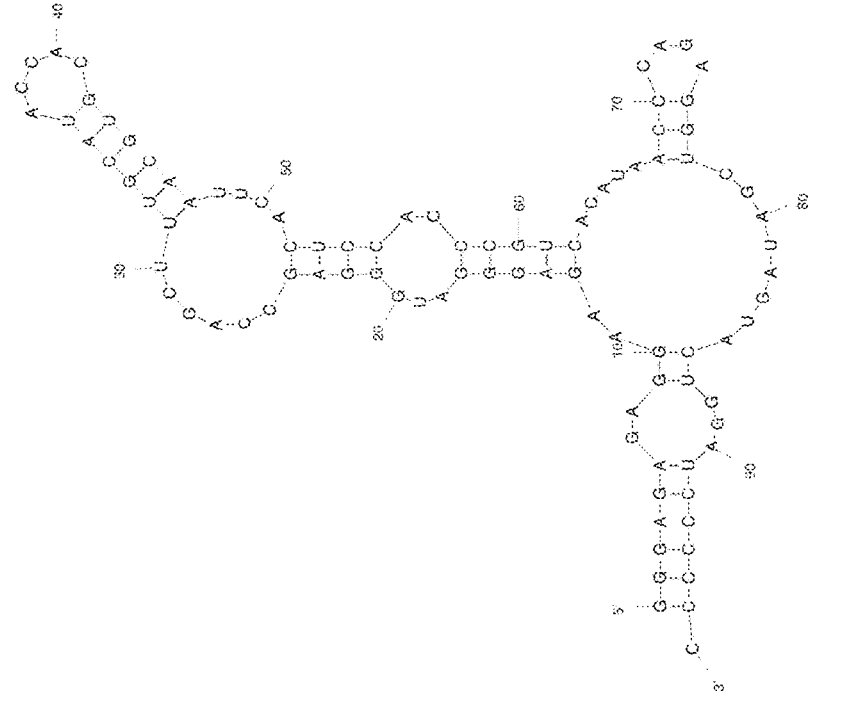
Structure 2
dG = -19.99
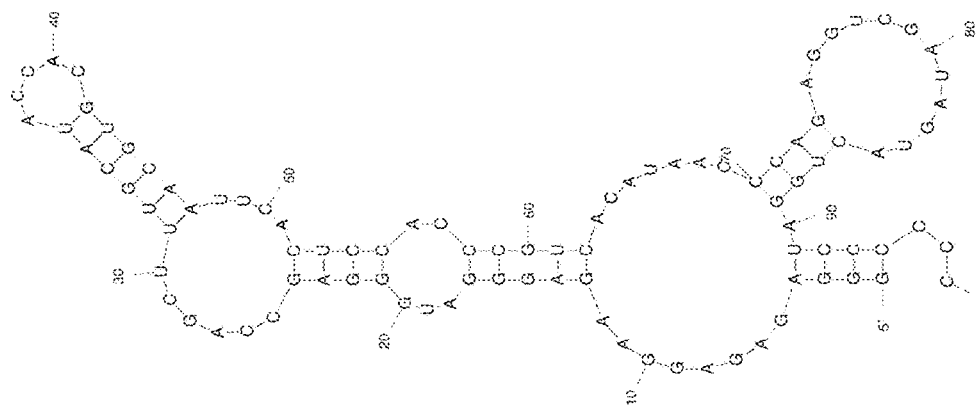
Structure 1
dG = -22.42

Family B (FAM-B)
Structure 3
dG = -22.15

Family C (FAM-C)

Family C (FAM-C)

FIG. 13A
Family D (FAM-D)
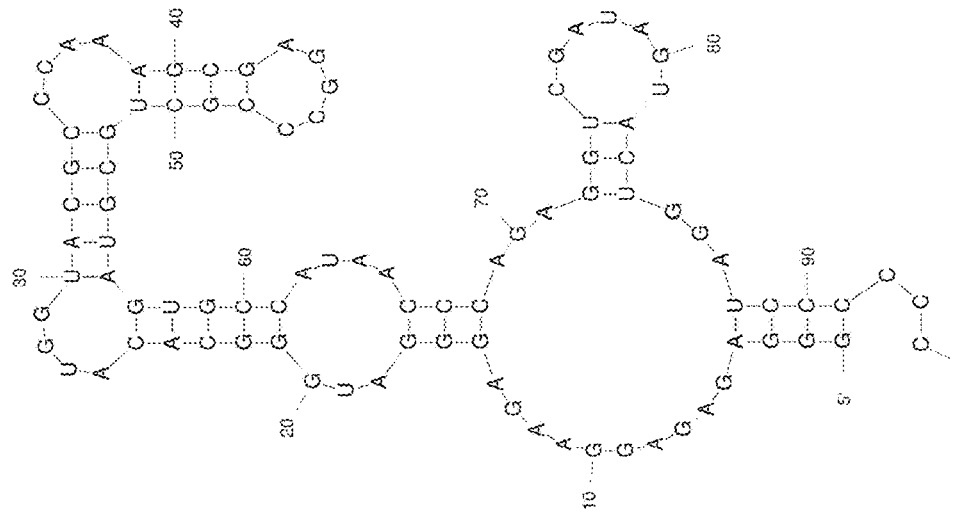
Structure 2
dG = -23.32
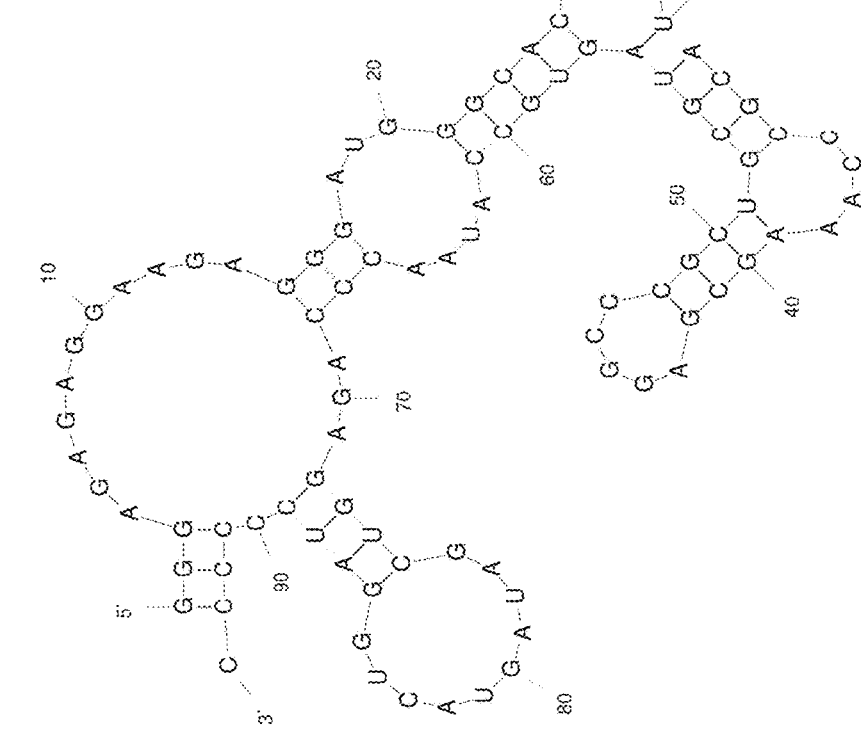
Structure 1
dG = -24.49

FIG. 13B
Family D (FAM-D)
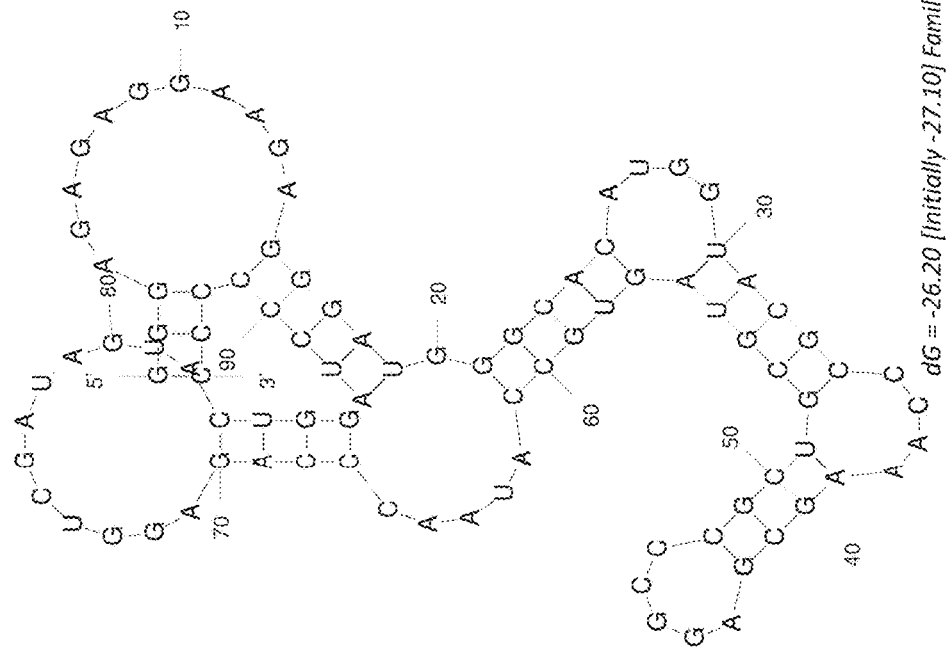
Structure 4
dG = -26.20
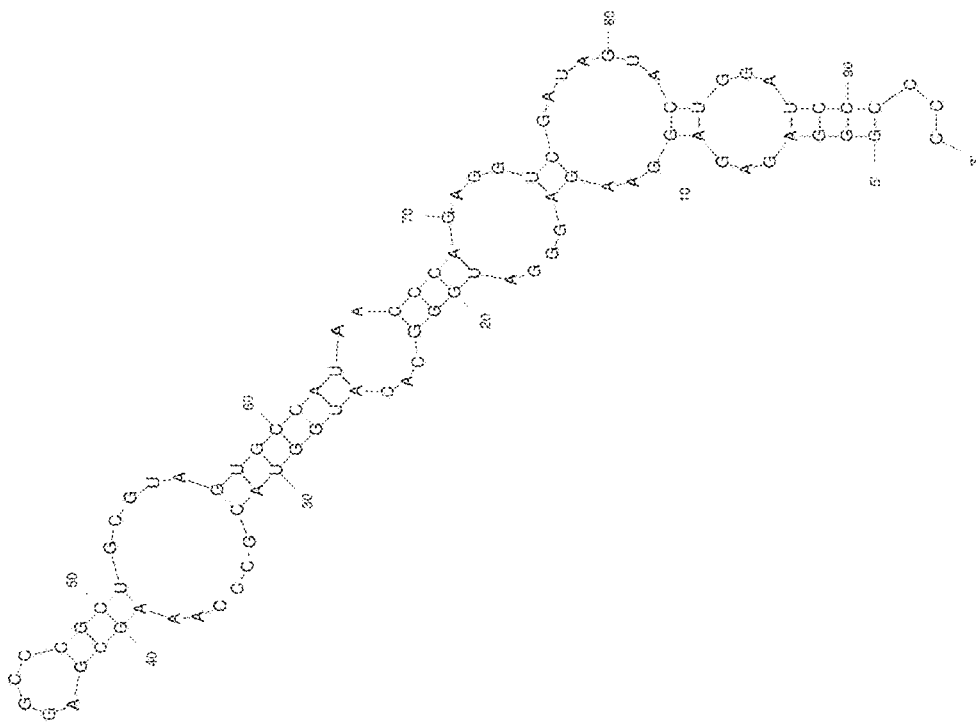
Structure 3
dG = -27.20

Family D (FAM-D)

Structure 5
dG = -23.25

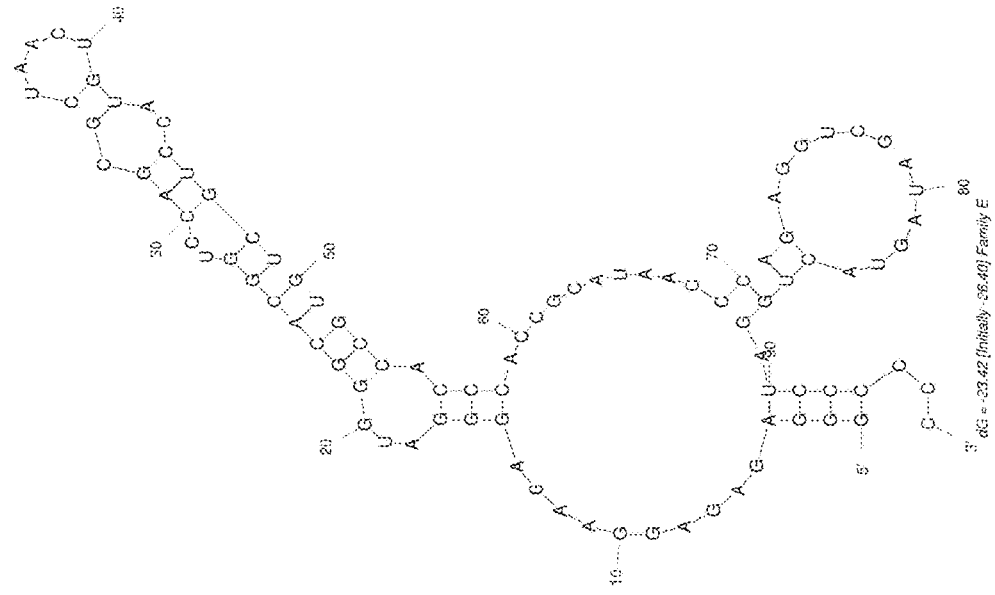
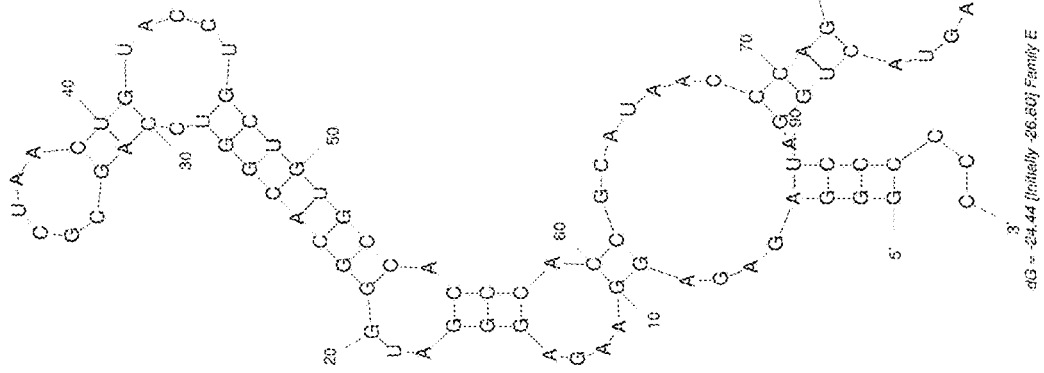
FIG. 14A
Family E (FAM-E)

Family E (FAM-E)

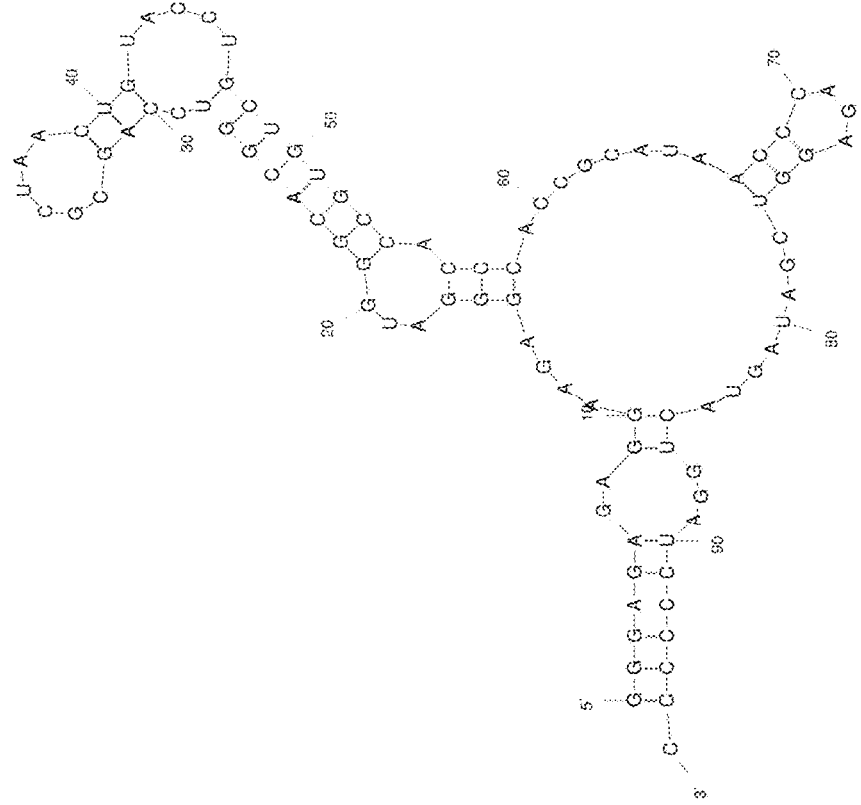
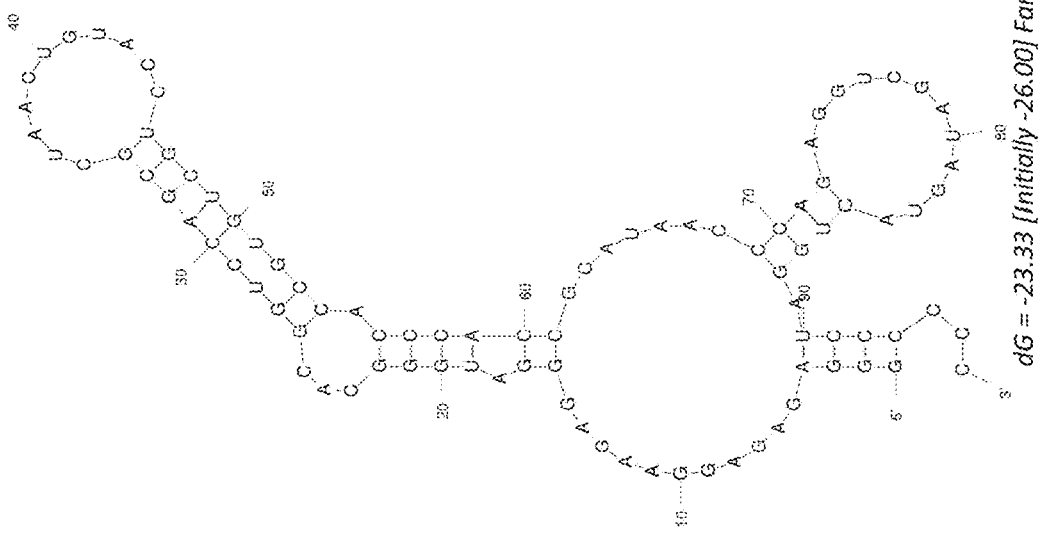
FIG. 14C
Family E (FAM-E)

Family E (FAM-E)

Structure 7
dG = -22.62

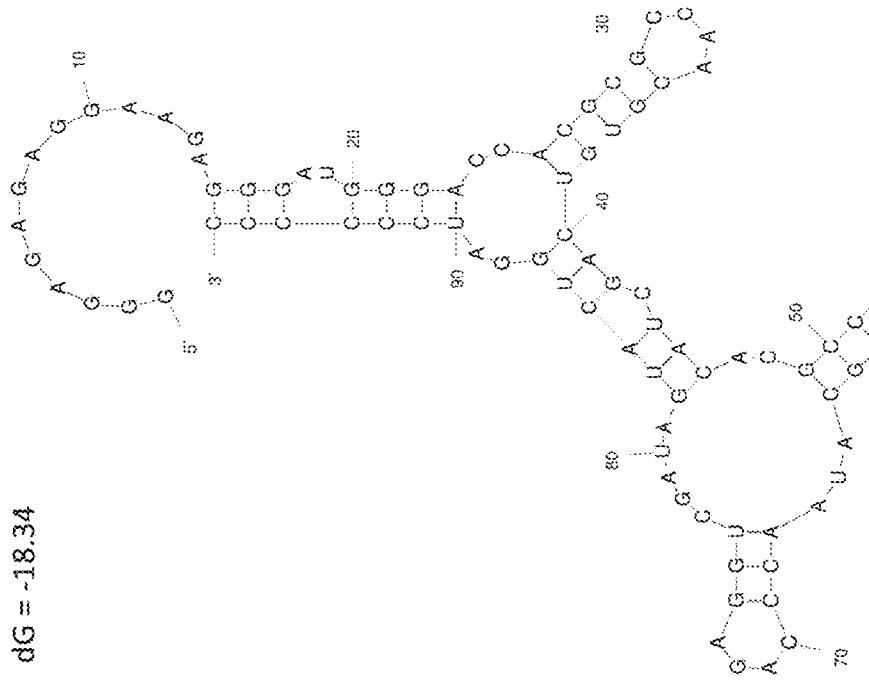
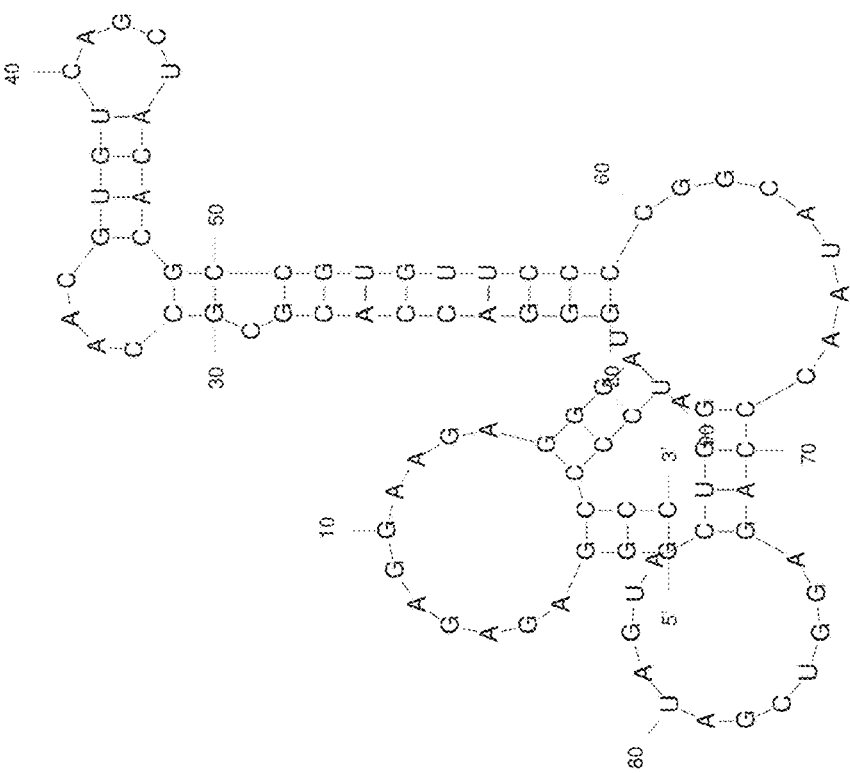
FIG. 15A
Family F (FAM-F)

Family F (FAM-F)

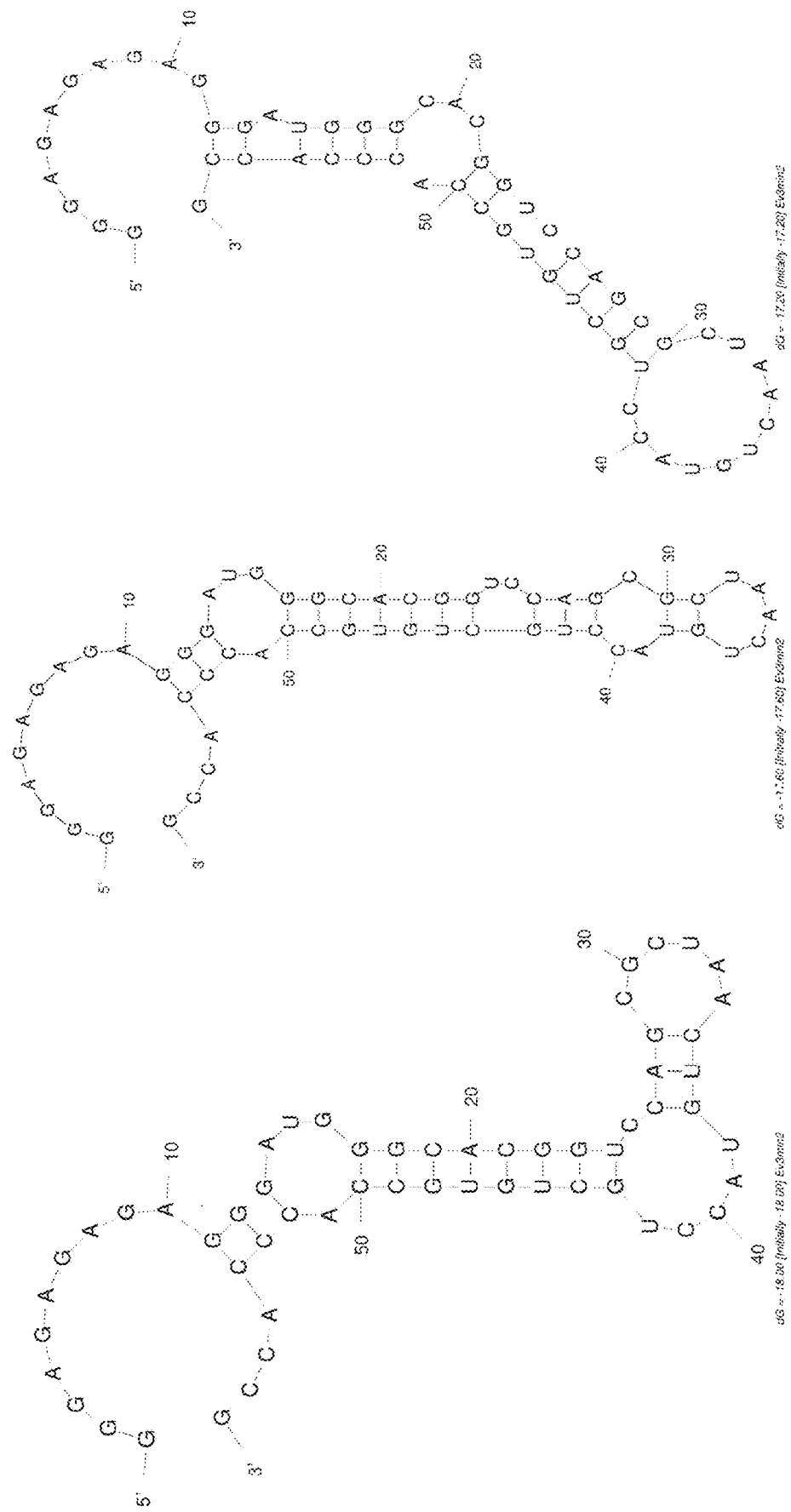

Ev3min3

Ev3min4

Ev3min5

Ev3min6

Ev3min7

Ev3min8

Ev3min9

Ev3min10

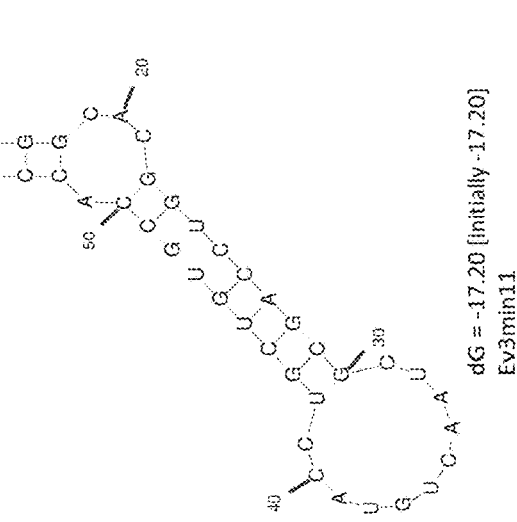
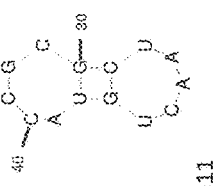
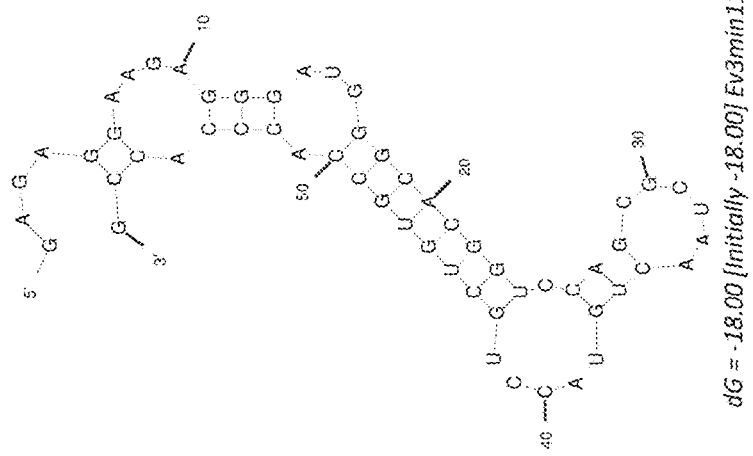
FIG. 25
Ev3min11

Ev3min12

FIG. 27
Ev3min13
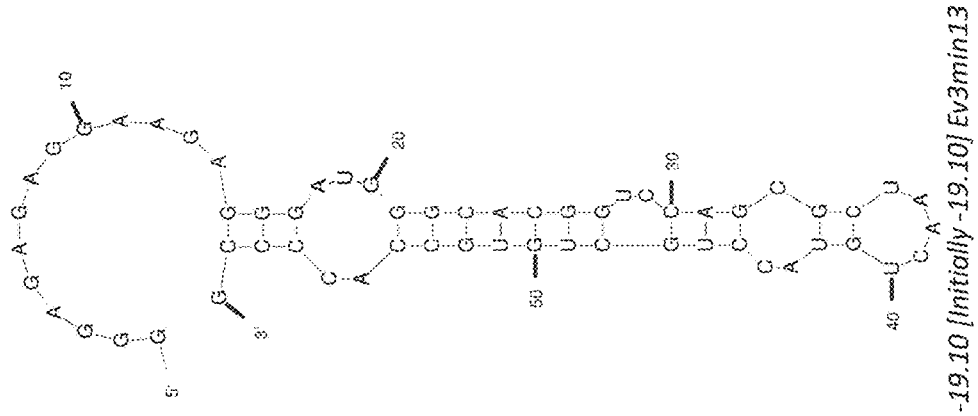
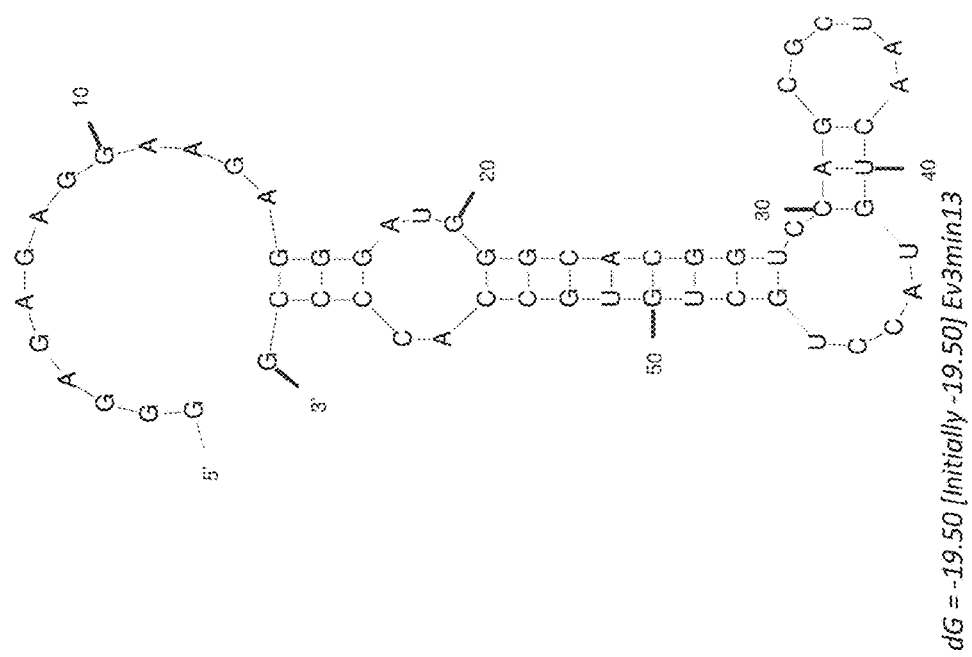

Ev3min15

Ev3min14

Ev3min16

Ev3min17

Ev3min18

Ev3min19

Ev3min20

Ev3min23

Ev3min24

Ev3min25

SEQUENCE LISTING

```
Sequence total quantity: 515
SEQ ID NO: 1            moltype = RNA  length = 39
FEATURE                 Location/Qualifiers
misc_feature            1..39
                        note = Synthetic
source                  1..39
                        mol_type = other RNA
                        organism = synthetic construct
SEQUENCE: 1
ccatctagat ctccgtagat tcccccggct ctttctcgc                          39

SEQ ID NO: 2            moltype = RNA  length = 41
FEATURE                 Location/Qualifiers
misc_feature            1..41
                        note = Synthetic
source                  1..41
                        mol_type = other RNA
                        organism = synthetic construct
SEQUENCE: 2
agccagcttt gcataccacg tgcaattcac tccaccgtc a                        41

SEQ ID NO: 3            moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 3
aagatctgct aagtgcacgc acaatcacca tcgagcgtct                         40
```

```
SEQ ID NO: 4              moltype = RNA   length = 38
FEATURE                   Location/Qualifiers
misc_feature              1..38
                          note = Synthetic
source                    1..38
                          mol_type = other RNA
                          organism = synthetic construct
SEQUENCE: 4
cacatggtac gcccaaagcg aggcccgctg cgtagtgc                              38

SEQ ID NO: 5              moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 5
cacggtccag cgctaactgt acctgctgtg ccacccaccg                            40

SEQ ID NO: 6              moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 6
accacgcgcc aacgtgtcag ctacacgccg tgttccccgg                            40

SEQ ID NO: 7              moltype = RNA   length = 95
FEATURE                   Location/Qualifiers
misc_feature              1..95
                          note = Synthetic
source                    1..95
                          mol_type = other RNA
                          organism = synthetic construct
SEQUENCE: 7
gggagagagg aagagggatg ggccatctag atctccgtag attccccgg ctctttctcg       60
ccataaccca gaggtcgata gtactggatc ccccc                                 95

SEQ ID NO: 8              moltype = RNA   length = 97
FEATURE                   Location/Qualifiers
misc_feature              1..97
                          note = Synthetic
source                    1..97
                          mol_type = other RNA
                          organism = synthetic construct
SEQUENCE: 8
gggagagagg aagagggatg ggagccagct ttgcatacca cgtgcaattc actccacccg      60
tcacataacc cagaggtcga tagtactgga tccccc                                97

SEQ ID NO: 9              moltype = RNA   length = 96
FEATURE                   Location/Qualifiers
misc_feature              1..96
                          note = Synthetic
source                    1..96
                          mol_type = other RNA
                          organism = synthetic construct
SEQUENCE: 9
gggagagagg aagagggatg ggaagatctg ctaagtgcac gcacaatcac catcgagcgt      60
ctcataaccc agaggtcgat agtactggat cccccc                                96

SEQ ID NO: 10             moltype = RNA   length = 94
FEATURE                   Location/Qualifiers
misc_feature              1..94
                          note = Synthetic
source                    1..94
                          mol_type = other RNA
                          organism = synthetic construct
SEQUENCE: 10
gggagagagg aagagggatg ggcacatggt acgcccaaag cgaggcccgc tgcgtagtgc      60
cataacccag aggtcgatag tactggatcc cccc                                  94

SEQ ID NO: 11             moltype = RNA   length = 96
FEATURE                   Location/Qualifiers
misc_feature              1..96
                          note = Synthetic
```

```
                        source              1..96
                                            mol_type = other RNA
                                            organism = synthetic construct
SEQUENCE: 11
gggagagagg aagagggatg ggcacggtcc agcgctaact gtacctgctg tgccacccac    60
cgcataaccc agaggtcgat agtactggat cccccc                              96

SEQ ID NO: 12           moltype = RNA   length = 96
FEATURE                 Location/Qualifiers
misc_feature            1..96
                        note = Synthetic
source                  1..96
                        mol_type = other RNA
                        organism = synthetic construct
SEQUENCE: 12
gggagagagg aagagggatg ggaccacgcg ccaacgtgtc agctacacgc cgtgttcccc    60
ggcataaccc agaggtcgat agtactggat cccccc                              96

SEQ ID NO: 13           moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 13
ccatctagat ctccgtagat tcccccggct ctttctcgc                            39

SEQ ID NO: 14           moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 14
agccagcttt gcataccacg tgcaattcac tccacccgtc a                         41

SEQ ID NO: 15           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 15
aagatctgct aagtgcacgc acaatcacca tcgagcgtct                           40

SEQ ID NO: 16           moltype = RNA   length = 38
FEATURE                 Location/Qualifiers
misc_feature            1..38
                        note = Synthetic
source                  1..38
                        mol_type = other RNA
                        organism = synthetic construct
SEQUENCE: 16
cacatggtac gcccaaagcg aggcccgctg cgtagtgc                             38

SEQ ID NO: 17           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 17
cacggtccag cgctaactgt acctgctgtg ccacccaccg                           40

SEQ ID NO: 18           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 18
accacgcgcc aacgtgtcag ctacacgccg tgttccccgg                           40

SEQ ID NO: 19           moltype = RNA   length = 39
```

```
FEATURE                 Location/Qualifiers
misc_feature            1..39
                        note = Synthetic
source                  1..39
                        mol_type = other RNA
                        organism = synthetic construct
SEQUENCE: 19
aagatcctcg cgcatctgcc gagcaatcac catcggacg                              39

SEQ ID NO: 20           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 20
ccaaatgcca agccgtagcc cggccagtag cccacacgtc                             40

SEQ ID NO: 21           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 21
tgccaagccg aggcccggcc accatccact gatagtgggc                             40

SEQ ID NO: 22           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 22
aagatcctga cgcgacacag caatcaccat cgaaccagct                             40

SEQ ID NO: 23           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 23
aagatctgcg gcaacgcaca atcaccatcg attccgaatt                             40

SEQ ID NO: 24           moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 24
gagctctcga tttcctccgc gacacccatc caaacctca                              39

SEQ ID NO: 25           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 25
ctctccggtc taccatccgg accggcgaca aagtcaactt                             40

SEQ ID NO: 26           moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 26
aagatctgct atgcacaatc accatcgggc gctccgggga a                           41
```

```
SEQ ID NO: 27            moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 27
ttgactctgc tgcgtagttc gcaccaagat caaccacttc                              40

SEQ ID NO: 28            moltype = RNA   length = 38
FEATURE                  Location/Qualifiers
misc_feature             1..38
                         note = Synthetic
source                   1..38
                         mol_type = other RNA
                         organism = synthetic construct
SEQUENCE: 28
taccaagtcg tggcccgact acccagcacg atgcgcaa                                38

SEQ ID NO: 29            moltype = RNA   length = 39
FEATURE                  Location/Qualifiers
misc_feature             1..39
                         note = Synthetic
source                   1..39
                         mol_type = other RNA
                         organism = synthetic construct
SEQUENCE: 29
ctattcgagt tcccacgaat cccccatcg agaacctac                                39

SEQ ID NO: 30            moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 30
tgccaagccg aggcccggcc accgtccccg cggctgatga                              40

SEQ ID NO: 31            moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 31
aatgatctcg ccaatgggcg acaatcacca tgtcttcaca                              40

SEQ ID NO: 32            moltype = RNA   length = 38
FEATURE                  Location/Qualifiers
misc_feature             1..38
                         note = Synthetic
source                   1..38
                         mol_type = other RNA
                         organism = synthetic construct
SEQUENCE: 32
tcagtgcgcc aagtggaggc cccaccgcag cccatcaa                                38

SEQ ID NO: 33            moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 33
tgtatgccag ctttgacgat aactgtcgcg cgtcaattca                              40

SEQ ID NO: 34            moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 34
tacgccaaag tggagcccac tcgtaccca tcatgagctg                               40
```

```
SEQ ID NO: 35              moltype = RNA   length = 40
FEATURE                    Location/Qualifiers
misc_feature               1..40
                           note = Synthetic
source                     1..40
                           mol_type = other RNA
                           organism = synthetic construct
SEQUENCE: 35
ccgccagctt tgggtaccct gaccaattca cggccatcca                              40

SEQ ID NO: 36              moltype = RNA   length = 40
FEATURE                    Location/Qualifiers
misc_feature               1..40
                           note = Synthetic
source                     1..40
                           mol_type = other RNA
                           organism = synthetic construct
SEQUENCE: 36
gtaattgtct gagaccaccg gacaatcaac aagaaatcct                              40

SEQ ID NO: 37              moltype = RNA   length = 40
FEATURE                    Location/Qualifiers
misc_feature               1..40
                           note = Synthetic
source                     1..40
                           mol_type = other RNA
                           organism = synthetic construct
SEQUENCE: 37
tcaggccaaa gtgtgatagc cacacccgca cccatcagga                              40

SEQ ID NO: 38              moltype = RNA   length = 40
FEATURE                    Location/Qualifiers
misc_feature               1..40
                           note = Synthetic
source                     1..40
                           mol_type = other RNA
                           organism = synthetic construct
SEQUENCE: 38
ccgaccgccg accagggtgc cactcgtacc cctgtccgcc                              40

SEQ ID NO: 39              moltype = RNA   length = 40
FEATURE                    Location/Qualifiers
misc_feature               1..40
                           note = Synthetic
source                     1..40
                           mol_type = other RNA
                           organism = synthetic construct
SEQUENCE: 39
tgccaagtcg aagcccgacc acgccatccc taacagtgcc                              40

SEQ ID NO: 40              moltype = RNA   length = 40
FEATURE                    Location/Qualifiers
misc_feature               1..40
                           note = Synthetic
source                     1..40
                           mol_type = other RNA
                           organism = synthetic construct
SEQUENCE: 40
acttgtgctg agtcgccaaa gtgaggccca ctcgccagca                              40

SEQ ID NO: 41              moltype = RNA   length = 40
FEATURE                    Location/Qualifiers
misc_feature               1..40
                           note = Synthetic
source                     1..40
                           mol_type = other RNA
                           organism = synthetic construct
SEQUENCE: 41
ccgccagctc ctctgaggca caagaggttc acggtgatcc                              40

SEQ ID NO: 42              moltype = RNA   length = 40
FEATURE                    Location/Qualifiers
misc_feature               1..40
                           note = Synthetic
source                     1..40
                           mol_type = other RNA
                           organism = synthetic construct
SEQUENCE: 42
```

```
caccaggttc tgctgtcccc aagcgctgac ccatccttcc                              40

SEQ ID NO: 43           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 43
aagatccggt aactcccccac cgcaatcacc gtcgactact                             40

SEQ ID NO: 44           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 44
ccatctagat ctccgtagat tcccccggc tctttctcgc                               40

SEQ ID NO: 45           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 45
ccatctgaac ccacagattc ccccatcatc agccacagtg                              40

SEQ ID NO: 46           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 46
cactaagttg gtagccccaa ctgccccgac acgaggatgt                              40

SEQ ID NO: 47           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 47
ttgtgctccg tggctccccg gaccaaccgc ttccagcagt                              40

SEQ ID NO: 48           moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 48
caatcacgcg tagtacgtcg cggaagatcc ccatgccga                               39

SEQ ID NO: 49           moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 49
cacatggtac gcccaaaagc gaggcccgct gcgtagtgc                               39

SEQ ID NO: 50           moltype = RNA   length = 40
FEATURE                 Location/Qualifiers
misc_feature            1..40
                        note = Synthetic
source                  1..40
                        mol_type = other RNA
                        organism = synthetic construct
```

```
SEQUENCE: 50
tgccatacgc ggttcgaagt cgaagcccga caacccggca                              40

SEQ ID NO: 51           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 51
gttattcaca tgcctcccgt gaatcaacaa gaattccttg                              40

SEQ ID NO: 52           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 52
aaagatctag actgtaagtc tccaatcgcc cagttaattc                              40

SEQ ID NO: 53           moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 53
gcccaatcgc cagtggaacg cgctgaagga tctgcaccc                               39

SEQ ID NO: 54           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 54
tgcaacgtaa aagagagtca tctcaggcta gtcgtctacc                              40

SEQ ID NO: 55           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 55
gtgtacgcca agtcgaggcc cgaccgtacc catacgcgac                              40

SEQ ID NO: 56           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 56
ttagctctac tttcctcttc agtaagacta accgcttctt                              40

SEQ ID NO: 57           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 57
tccaagcgga ggccccgcac ccaccctcca acgggcacgg                              40

SEQ ID NO: 58           moltype = RNA   length = 40
FEATURE                 Location/Qualifiers
misc_feature            1..40
                        note = Synthetic
source                  1..40
                        mol_type = other RNA
```

```
                        organism = synthetic construct
SEQUENCE: 58
tatcgctcca caacgactcc cgtggactac ccaattccaa                              40

SEQ ID NO: 59           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 59
gtcgtgccca agtgaaggcc tcacgcacgc atcctaacct                              40

SEQ ID NO: 60           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 60
aagatctgcg ccagcacaat caccatcgtc ctgagaatgg                              40

SEQ ID NO: 61           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 61
atgccaagca gtggccctgc cacccaccta tcactgtcga                              40

SEQ ID NO: 62           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 62
aacagaccaa gcagcggccc tgctctgcca tcatacgcct                              40

SEQ ID NO: 63           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 63
gtcattcgct gacgaatcaa catgaattcc taactgctga                              40

SEQ ID NO: 64           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 64
acacgccaag ctggtagccc cagccgtgcc cattacggcc                              40

SEQ ID NO: 65           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 65
tagccaagca gcagccctgc caacccatcc tacccgggcg                              40

SEQ ID NO: 66           moltype = RNA   length = 40
FEATURE                 Location/Qualifiers
misc_feature            1..40
                        note = Synthetic
source                  1..40
```

```
                            mol_type = other RNA
                            organism = synthetic construct
SEQUENCE: 66
gcccaaggcg aggcccgccg ctccatccag acgctgaggg                              40

SEQ ID NO: 67               moltype = RNA    length = 40
FEATURE                     Location/Qualifiers
misc_feature                1..40
                            note = Synthetic
source                      1..40
                            mol_type = other RNA
                            organism = synthetic construct
SEQUENCE: 67
aagatctcgt catgctttga cgtcaatcac cattgttccc                              40

SEQ ID NO: 68               moltype = RNA    length = 39
FEATURE                     Location/Qualifiers
misc_feature                1..39
                            note = Synthetic
source                      1..39
                            mol_type = other RNA
                            organism = synthetic construct
SEQUENCE: 68
atcccccagg atgagcacgt tgccatggac tggctatcc                               39

SEQ ID NO: 69               moltype = RNA    length = 40
FEATURE                     Location/Qualifiers
misc_feature                1..40
                            note = Synthetic
source                      1..40
                            mol_type = other RNA
                            organism = synthetic construct
SEQUENCE: 69
ctgttacagt ctcgcgtaac cccccatcg atgtcctcga                               40

SEQ ID NO: 70               moltype = RNA    length = 40
FEATURE                     Location/Qualifiers
misc_feature                1..40
                            note = Synthetic
source                      1..40
                            mol_type = other RNA
                            organism = synthetic construct
SEQUENCE: 70
agccagcttt cggcaaaccg aattcactcc accctgctca                              40

SEQ ID NO: 71               moltype = RNA    length = 40
FEATURE                     Location/Qualifiers
misc_feature                1..40
                            note = Synthetic
source                      1..40
                            mol_type = other RNA
                            organism = synthetic construct
SEQUENCE: 71
cacggtataa cctcctcata tacctgctgt gccacccgcg                              40

SEQ ID NO: 72               moltype = RNA    length = 40
FEATURE                     Location/Qualifiers
misc_feature                1..40
                            note = Synthetic
source                      1..40
                            mol_type = other RNA
                            organism = synthetic construct
SEQUENCE: 72
ccggaagatc tgctcgcact agccggagcc caatcacggc                              40

SEQ ID NO: 73               moltype = RNA    length = 40
FEATURE                     Location/Qualifiers
misc_feature                1..40
                            note = Synthetic
source                      1..40
                            mol_type = other RNA
                            organism = synthetic construct
SEQUENCE: 73
cctgccgaac ggctaagtcg cagcccgacc cgcggcaggg                              40

SEQ ID NO: 74               moltype = RNA    length = 40
FEATURE                     Location/Qualifiers
misc_feature                1..40
                            note = Synthetic
```

```
source                      1..40
                            mol_type = other RNA
                            organism = synthetic construct
SEQUENCE: 74
ctccgacccg cggacgaagt caacttccac agtcccacac                           40

SEQ ID NO: 75               moltype = RNA  length = 40
FEATURE                     Location/Qualifiers
misc_feature                1..40
                            note = Synthetic
source                      1..40
                            mol_type = other RNA
                            organism = synthetic construct
SEQUENCE: 75
acattaggat ctgcgtgatg gggatcaccc gctacatgtc                           40

SEQ ID NO: 76               moltype = RNA  length = 40
FEATURE                     Location/Qualifiers
misc_feature                1..40
                            note = Synthetic
source                      1..40
                            mol_type = other RNA
                            organism = synthetic construct
SEQUENCE: 76
tctaagatgg ggaagatctc cggagcaccg ggcaatcacc                           40

SEQ ID NO: 77               moltype = RNA  length = 38
FEATURE                     Location/Qualifiers
misc_feature                1..38
                            note = Synthetic
source                      1..38
                            mol_type = other RNA
                            organism = synthetic construct
SEQUENCE: 77
ctattcgagt tcccacgaat cccccatcga gaacctac                             38

SEQ ID NO: 78               moltype = RNA  length = 40
FEATURE                     Location/Qualifiers
misc_feature                1..40
                            note = Synthetic
source                      1..40
                            mol_type = other RNA
                            organism = synthetic construct
SEQUENCE: 78
tgccaagccg aggcccggcc agcatccctc acgagagagg                           40

SEQ ID NO: 79               moltype = RNA  length = 40
FEATURE                     Location/Qualifiers
misc_feature                1..40
                            note = Synthetic
source                      1..40
                            mol_type = other RNA
                            organism = synthetic construct
SEQUENCE: 79
gccaagcacg tagcccgtgc ccccacccgc ctgtgtgctg                           40

SEQ ID NO: 80               moltype = RNA  length = 40
FEATURE                     Location/Qualifiers
misc_feature                1..40
                            note = Synthetic
source                      1..40
                            mol_type = other RNA
                            organism = synthetic construct
SEQUENCE: 80
tgccaagcac gaagcccgtg cccccatcca gagtgtgaga                           40

SEQ ID NO: 81               moltype = RNA  length = 42
FEATURE                     Location/Qualifiers
misc_feature                1..42
                            note = Synthetic
source                      1..42
                            mol_type = other RNA
                            organism = synthetic construct
SEQUENCE: 81
agccagcttt tgcataccac gtgcaattca ctccacccgt ca                        42

SEQ ID NO: 82               moltype = RNA  length = 40
FEATURE                     Location/Qualifiers
misc_feature                1..40
```

```
                        note = Synthetic
source                  1..40
                        mol_type = other RNA
                        organism = synthetic construct
SEQUENCE: 82
ctttgtaaac ccggcaaaca aaatcaactt ccatcatcaa                              40

SEQ ID NO: 83           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 83
ccattgtagc gaccacacaa ttccccatcg gacagcatgg                              40

SEQ ID NO: 84           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 84
ctctcgccgt tcccaggcac gacaaaatca acttcccgct                              40

SEQ ID NO: 85           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 85
aagccaagcc gcggcccggc cttcccatgt gctactagag                              40

SEQ ID NO: 86           moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 86
ccaaatgcca aagccgtagc ccggccagta gcccacacgt c                            41

SEQ ID NO: 87           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 87
ccattacgcg acgtaattcc cccatcgttt cctcgttaag                              40

SEQ ID NO: 88           moltype = RNA   length = 38
FEATURE                 Location/Qualifiers
misc_feature            1..38
                        note = Synthetic
source                  1..38
                        mol_type = other RNA
                        organism = synthetic construct
SEQUENCE: 88
ccatctagat ctccgtagat tccccggctc tttctcgc                                38

SEQ ID NO: 89           moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 89
actgtctgca tacacggtat gcccaacgcc atccaaaccg                              40

SEQ ID NO: 90           moltype = RNA   length = 40
FEATURE                 Location/Qualifiers
```

```
misc_feature          1..40
                      note = Synthetic
source                1..40
                      mol_type = other RNA
                      organism = synthetic construct
SEQUENCE: 90
acctgcggct attgccagcg ccataagacc ctccacagta                    40

SEQ ID NO: 91         moltype = RNA  length = 39
FEATURE               Location/Qualifiers
misc_feature          1..39
                      note = Synthetic
source                1..39
                      mol_type = other RNA
                      organism = synthetic construct
SEQUENCE: 91
ccatctagat ctccgtagat tcccccggct ctttctcgc                     39

SEQ ID NO: 92         moltype = RNA  length = 39
FEATURE               Location/Qualifiers
misc_feature          1..39
                      note = Synthetic
source                1..39
                      mol_type = other RNA
                      organism = synthetic construct
SEQUENCE: 92
ccatctagat ctccgtagat tcccccggct cttcctcgc                     39

SEQ ID NO: 93         moltype = RNA  length = 39
FEATURE               Location/Qualifiers
misc_feature          1..39
                      note = Synthetic
source                1..39
                      mol_type = other RNA
                      organism = synthetic construct
SEQUENCE: 93
ccatctagat ctccgtagat tcccccagct ctttctcgc                     39

SEQ ID NO: 94         moltype = RNA  length = 41
FEATURE               Location/Qualifiers
misc_feature          1..41
                      note = Synthetic
source                1..41
                      mol_type = other RNA
                      organism = synthetic construct
SEQUENCE: 94
agccagcttt gcataccacg tgcaattcac tccacccgtc a                  41

SEQ ID NO: 95         moltype = RNA  length = 41
FEATURE               Location/Qualifiers
misc_feature          1..41
                      note = Synthetic
source                1..41
                      mol_type = other RNA
                      organism = synthetic construct
SEQUENCE: 95
agccagcttt gcataccacg tgcaattcac tccacccgtc g                  41

SEQ ID NO: 96         moltype = RNA  length = 40
FEATURE               Location/Qualifiers
misc_feature          1..40
                      note = Synthetic
source                1..40
                      mol_type = other RNA
                      organism = synthetic construct
SEQUENCE: 96
aagatctgct aagtgcacgc acaatcacca tcgagcgtct                    40

SEQ ID NO: 97         moltype = RNA  length = 40
FEATURE               Location/Qualifiers
misc_feature          1..40
                      note = Synthetic
source                1..40
                      mol_type = other RNA
                      organism = synthetic construct
SEQUENCE: 97
aagatctgct aagtgcacgc acaatcacca tcgagcgtcc                    40

SEQ ID NO: 98         moltype = RNA  length = 40
```

```
FEATURE              Location/Qualifiers
misc_feature         1..40
                     note = Synthetic
source               1..40
                     mol_type = other RNA
                     organism = synthetic construct
SEQUENCE: 98
aagatctgct aagtgcacgc acaatcacca tcgagcgcct                              40

SEQ ID NO: 99        moltype = RNA   length = 39
FEATURE              Location/Qualifiers
misc_feature         1..39
                     note = Synthetic
source               1..39
                     mol_type = other RNA
                     organism = synthetic construct
SEQUENCE: 99
aagatctgct aagtgcacgc acaatcacca tcgagcgtc                               39

SEQ ID NO: 100       moltype = RNA   length = 40
FEATURE              Location/Qualifiers
misc_feature         1..40
                     note = Synthetic
source               1..40
                     mol_type = other RNA
                     organism = synthetic construct
SEQUENCE: 100
aagatctgct aagtgcacgc acaatcacca tcgagcgact                              40

SEQ ID NO: 101       moltype = RNA   length = 38
FEATURE              Location/Qualifiers
misc_feature         1..38
                     note = Synthetic
source               1..38
                     mol_type = other RNA
                     organism = synthetic construct
SEQUENCE: 101
cacatggtac gcccaaagcg aggcccgctg cgtagtgc                                38

SEQ ID NO: 102       moltype = RNA   length = 38
FEATURE              Location/Qualifiers
misc_feature         1..38
                     note = Synthetic
source               1..38
                     mol_type = other RNA
                     organism = synthetic construct
SEQUENCE: 102
cacacggtac gcccaaagcg aggcccgctg cgtagtgc                                38

SEQ ID NO: 103       moltype = RNA   length = 40
FEATURE              Location/Qualifiers
misc_feature         1..40
                     note = Synthetic
source               1..40
                     mol_type = other RNA
                     organism = synthetic construct
SEQUENCE: 103
cacggtccag cgctaactgt acctgctgtg ccacccaccg                              40

SEQ ID NO: 104       moltype = RNA   length = 40
FEATURE              Location/Qualifiers
misc_feature         1..40
                     note = Synthetic
source               1..40
                     mol_type = other RNA
                     organism = synthetic construct
SEQUENCE: 104
cacggtccag cgctaactgt acctgctgtg ccacccacca                              40

SEQ ID NO: 105       moltype = RNA   length = 40
FEATURE              Location/Qualifiers
misc_feature         1..40
                     note = Synthetic
source               1..40
                     mol_type = other RNA
                     organism = synthetic construct
SEQUENCE: 105
cacggtccag cgctaactgt acctgctgtg ccacccactg                              40
```

| | | |
|---|---|---|
| SEQ ID NO: 106<br>FEATURE<br>misc_feature<br><br>source | moltype = RNA   length = 40<br>Location/Qualifiers<br>1..40<br>note = Synthetic<br>1..40<br>mol_type = other RNA<br>organism = synthetic construct | |
| SEQUENCE: 106<br>cacggtccag cgctaactgt acctgctgtg ccacccacct | | 40 |
| SEQ ID NO: 107<br>FEATURE<br>misc_feature<br><br>source | moltype = RNA   length = 40<br>Location/Qualifiers<br>1..40<br>note = Synthetic<br>1..40<br>mol_type = other RNA<br>organism = synthetic construct | |
| SEQUENCE: 107<br>cacggtccag cgctaactgt acctgctgtg ccacccgccg | | 40 |
| SEQ ID NO: 108<br>FEATURE<br>misc_feature<br><br>source | moltype = RNA   length = 40<br>Location/Qualifiers<br>1..40<br>note = Synthetic<br>1..40<br>mol_type = other RNA<br>organism = synthetic construct | |
| SEQUENCE: 108<br>accacgcgcc aacgtgtcag ctacacgccg tgttccccgg | | 40 |
| SEQ ID NO: 109<br>FEATURE<br>misc_feature<br><br>source | moltype = RNA   length = 40<br>Location/Qualifiers<br>1..40<br>note = Synthetic<br>1..40<br>mol_type = other RNA<br>organism = synthetic construct | |
| SEQUENCE: 109<br>accacgcgcc aacgtgtcag ctacacgccg tgttccccga | | 40 |
| SEQ ID NO: 110<br>FEATURE<br>misc_feature<br><br>source | moltype = RNA   length = 39<br>Location/Qualifiers<br>1..39<br>note = Synthetic<br>1..39<br>mol_type = other RNA<br>organism = synthetic construct | |
| SEQUENCE: 110<br>accacgcgcc aacgtgtcag ctacacgccg tgttccccg | | 39 |
| SEQ ID NO: 111<br>FEATURE<br>misc_feature<br><br>source | moltype = RNA   length = 39<br>Location/Qualifiers<br>1..39<br>note = Synthetic<br>1..39<br>mol_type = other RNA<br>organism = synthetic construct | |
| SEQUENCE: 111<br>ccacgcgcca acgtgtcagc tacacgccgt gttccccgg | | 39 |
| SEQ ID NO: 112<br>FEATURE<br>misc_feature<br><br>source | moltype = RNA   length = 39<br>Location/Qualifiers<br>1..39<br>note = Synthetic<br>1..39<br>mol_type = other RNA<br>organism = synthetic construct | |
| SEQUENCE: 112<br>aagatcctcg cgcatctgcc gagcaatcac catcggacg | | 39 |
| SEQ ID NO: 113<br>FEATURE<br>misc_feature<br><br>source | moltype = RNA   length = 39<br>Location/Qualifiers<br>1..39<br>note = Synthetic<br>1..39<br>mol_type = other RNA<br>organism = synthetic construct | |
| SEQUENCE: 113<br>aagatcctcg cgcatctgcc gagcaatcac catcggacc | | 39 |

```
SEQ ID NO: 114          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 114
aagatcctcg cgcatctgcc gagcaatcac catcggaca                              39

SEQ ID NO: 115          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 115
aagatcctcg cgcatctgcc gagcaatcac catcggact                              39

SEQ ID NO: 116          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 116
aaagatcctc gcgcatctgc cgagcaatca ccatcggacg                             40

SEQ ID NO: 117          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 117
aagatcctcg cgcacctgcc gagcaatcac catcggacg                              39

SEQ ID NO: 118          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 118
ccaaatgcca agccgtagcc cggccagtag cccacacgtc                             40

SEQ ID NO: 119          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 119
ccaaaatgcc aagccgtagc ccggccagta gcccacacgt c                           41

SEQ ID NO: 120          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 120
ccaaatgcca agccgtagcc cggccagtag cccacacgac                             40

SEQ ID NO: 121          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 121
```

```
ccaaatgcca agccgtagcc cggccagtag cccacacgta                               40

SEQ ID NO: 122          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 122
tgccaagccg aggcccggcc accatccact gatagtgggc                               40

SEQ ID NO: 123          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 123
tgccaagccg aggcccggcc accatccact gatagtggga                               40

SEQ ID NO: 124          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 124
tgccaagccg aggcccggcc accatccact gatagtggg                                39

SEQ ID NO: 125          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 125
tgccaagccg aggcccggcc accatccact gatagtgggt                               40

SEQ ID NO: 126          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 126
aagatcctga cgcgacacag caatcaccat cgaaccagct                               40

SEQ ID NO: 127          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 127
aagatcctga cgcgacacag caatcaccat cgaaccagcc                               40

SEQ ID NO: 128          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 128
aagatctgcg gcaacgcaca atcaccatcg attccgaatt                               40

SEQ ID NO: 129          moltype = RNA   length = 40
FEATURE                 Location/Qualifiers
misc_feature            1..40
                        note = Synthetic
source                  1..40
                        mol_type = other RNA
                        organism = synthetic construct
```

```
SEQUENCE: 129
aagatctgcg gcaacgcaca atcaccatcg attccgaatg                          40

SEQ ID NO: 130          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 130
aagatctgcg gcaacgcaca atcaccatcg attccgaatc                          40

SEQ ID NO: 131          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 131
aagatctgcg gcaacgcaca atcaccatcg attccgaact                          40

SEQ ID NO: 132          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 132
aagatctgcg gcaacgtaca atcaccatcg attccgaatt                          40

SEQ ID NO: 133          moltype = RNA  length = 39
FEATURE                 Location/Qualifiers
misc_feature            1..39
                        note = Synthetic
source                  1..39
                        mol_type = other RNA
                        organism = synthetic construct
SEQUENCE: 133
gagctctcga tttcctccgc gacacccatc caaacctca                           39

SEQ ID NO: 134          moltype = RNA  length = 38
FEATURE                 Location/Qualifiers
misc_feature            1..38
                        note = Synthetic
source                  1..38
                        mol_type = other RNA
                        organism = synthetic construct
SEQUENCE: 134
agctctcgat ttcctccgcg acacccatcc aaacctca                            38

SEQ ID NO: 135          moltype = RNA  length = 39
FEATURE                 Location/Qualifiers
misc_feature            1..39
                        note = Synthetic
source                  1..39
                        mol_type = other RNA
                        organism = synthetic construct
SEQUENCE: 135
gagctctcga tttcctccgc gacacccatc caaacctcg                           39

SEQ ID NO: 136          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 136
ctctccggtc taccatccgg accggcgaca aagtcaactt                          40

SEQ ID NO: 137          moltype = RNA  length = 40
FEATURE                 Location/Qualifiers
misc_feature            1..40
                        note = Synthetic
source                  1..40
                        mol_type = other RNA
```

```
                        organism = synthetic construct
SEQUENCE: 137
ctctccggtc taccacccgg accggcgaca aagtcaactt                                40

SEQ ID NO: 138          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 138
aagatctgct atgcacaatc accatcgggc gctccgggga a                              41

SEQ ID NO: 139          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 139
aagatctgct atgcacaatc accatcgggc gctccgggaa                                40

SEQ ID NO: 140          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 140
aagatctgct acgcacaatc accatcgggc gctccgggga a                              41

SEQ ID NO: 141          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 141
ttgactctgc tgcgtagttc gcaccaagat caaccacttc                                40

SEQ ID NO: 142          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 142
ttgactctgc tgcgtagttc gcaccaagat caaccacttc c                              41

SEQ ID NO: 143          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 143
ttgactctgc tgcgtagctc gcaccaagat caaccacttc                                40

SEQ ID NO: 144          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 144
ttgactctgc tgcgcagttc gcaccaagat caaccacttc                                40

SEQ ID NO: 145          moltype = RNA   length = 40
FEATURE                 Location/Qualifiers
misc_feature            1..40
                        note = Synthetic
source                  1..40
```

```
                        mol_type = other RNA
                        organism = synthetic construct
SEQUENCE: 145
ttgactctgc tgcgtagtcc gcaccaagat caaccacttc                              40

SEQ ID NO: 146          moltype = RNA   length = 38
FEATURE                 Location/Qualifiers
misc_feature            1..38
                        note = Synthetic
source                  1..38
                        mol_type = other RNA
                        organism = synthetic construct
SEQUENCE: 146
taccaagtcg tggcccgact acccagcacg atgcgcaa                                38

SEQ ID NO: 147          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 147
taccaaagtc gtggcccgac tacccagcac gatgcgcaa                               39

SEQ ID NO: 148          moltype = RNA   length = 38
FEATURE                 Location/Qualifiers
misc_feature            1..38
                        note = Synthetic
source                  1..38
                        mol_type = other RNA
                        organism = synthetic construct
SEQUENCE: 148
taccaagtcg tggcccgact acccagcacg gtgcgcaa                                38

SEQ ID NO: 149          moltype = RNA   length = 38
FEATURE                 Location/Qualifiers
misc_feature            1..38
                        note = Synthetic
source                  1..38
                        mol_type = other RNA
                        organism = synthetic construct
SEQUENCE: 149
taccaagtcg tggcccgact acccagcacg atgcgcag                                38

SEQ ID NO: 150          moltype = RNA   length = 38
FEATURE                 Location/Qualifiers
misc_feature            1..38
                        note = Synthetic
source                  1..38
                        mol_type = other RNA
                        organism = synthetic construct
SEQUENCE: 150
taccaagtcg tggcccgact acccagcaca atgcgcaa                                38

SEQ ID NO: 151          moltype = RNA   length = 38
FEATURE                 Location/Qualifiers
misc_feature            1..38
                        note = Synthetic
source                  1..38
                        mol_type = other RNA
                        organism = synthetic construct
SEQUENCE: 151
taccaagtcg cggcccgact acccagcacg atgcgcaa                                38

SEQ ID NO: 152          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 152
ctattcgagt tcccacgaat cccccatcg agaacctac                                39

SEQ ID NO: 153          moltype = RNA   length = 38
FEATURE                 Location/Qualifiers
misc_feature            1..38
                        note = Synthetic
```

```
source                      1..38
                            mol_type = other RNA
                            organism = synthetic construct
SEQUENCE: 153
ctattcgagt tcccacgaat ccccccatcg agaaccta                               38

SEQ ID NO: 154              moltype = RNA   length = 39
FEATURE                     Location/Qualifiers
misc_feature                1..39
                            note = Synthetic
source                      1..39
                            mol_type = other RNA
                            organism = synthetic construct
SEQUENCE: 154
ctattcgagt tcccacgaat ccccccatcg agaacctat                              39

SEQ ID NO: 155              moltype = RNA   length = 39
FEATURE                     Location/Qualifiers
misc_feature                1..39
                            note = Synthetic
source                      1..39
                            mol_type = other RNA
                            organism = synthetic construct
SEQUENCE: 155
ctattcgagt tcccacgaat ccccccatcg agaacctaa                              39

SEQ ID NO: 156              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 156
tgccaagccg aggcccggcc accgtccccg cggctgatga                             40

SEQ ID NO: 157              moltype = RNA   length = 41
FEATURE                     Location/Qualifiers
misc_feature                1..41
                            note = Synthetic
source                      1..41
                            mol_type = other RNA
                            organism = synthetic construct
SEQUENCE: 157
tgccaaagcc gaggcccggc caccgtcccc gcggctgatg a                           41

SEQ ID NO: 158              moltype = RNA   length = 41
FEATURE                     Location/Qualifiers
misc_feature                1..41
                            note = Synthetic
source                      1..41
                            mol_type = other RNA
                            organism = synthetic construct
SEQUENCE: 158
tgccaagccg aggcccggcc accgtccccg cggctgatcg a                           41

SEQ ID NO: 159              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 159
tgccaagccg aggcccggcc accgtccccg cggctgatgg                             40

SEQ ID NO: 160              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 160
tgccaagccg aggcccggcc accgtccccg cggctgacga                             40

SEQ ID NO: 161              moltype = RNA   length = 40
FEATURE                     Location/Qualifiers
misc_feature                1..40
```

```
                    note = Synthetic
source              1..40
                    mol_type = other RNA
                    organism = synthetic construct
SEQUENCE: 161
aatgatctcg ccaatgggcg acaatcacca tgtcttcaca                              40

SEQ ID NO: 162      moltype = RNA  length = 40
FEATURE             Location/Qualifiers
misc_feature        1..40
                    note = Synthetic
source              1..40
                    mol_type = other RNA
                    organism = synthetic construct
SEQUENCE: 162
aacgatctcg ccaatgggcg acaatcacca tgtcttcaca                              40

SEQ ID NO: 163      moltype = RNA  length = 40
FEATURE             Location/Qualifiers
misc_feature        1..40
                    note = Synthetic
source              1..40
                    mol_type = other RNA
                    organism = synthetic construct
SEQUENCE: 163
aatgatctcg ccaatgggcg acaatcacca tgtcttcacg                              40

SEQ ID NO: 164      moltype = RNA  length = 40
FEATURE             Location/Qualifiers
misc_feature        1..40
                    note = Synthetic
source              1..40
                    mol_type = other RNA
                    organism = synthetic construct
SEQUENCE: 164
aatgatctcg ccaatgtgcg acaatcacca tgtcttcaca                              40

SEQ ID NO: 165      moltype = RNA  length = 38
FEATURE             Location/Qualifiers
misc_feature        1..38
                    note = Synthetic
source              1..38
                    mol_type = other RNA
                    organism = synthetic construct
SEQUENCE: 165
tcagtgcgcc aagtggaggc cccaccgcag cccatcaa                                38

SEQ ID NO: 166      moltype = RNA  length = 38
FEATURE             Location/Qualifiers
misc_feature        1..38
                    note = Synthetic
source              1..38
                    mol_type = other RNA
                    organism = synthetic construct
SEQUENCE: 166
tcagtgcgcc aagtggaggc cccaccgcag cccatcga                                38

SEQ ID NO: 167      moltype = RNA  length = 38
FEATURE             Location/Qualifiers
misc_feature        1..38
                    note = Synthetic
source              1..38
                    mol_type = other RNA
                    organism = synthetic construct
SEQUENCE: 167
tcagtgcgcc aagtggaggc cccaccgcag cccatcag                                38

SEQ ID NO: 168      moltype = RNA  length = 40
FEATURE             Location/Qualifiers
misc_feature        1..40
                    note = Synthetic
source              1..40
                    mol_type = other RNA
                    organism = synthetic construct
SEQUENCE: 168
tgtatgccag ctttgacgat aactgtcgcg cgtcaattca                              40

SEQ ID NO: 169      moltype = RNA  length = 40
FEATURE             Location/Qualifiers
```

-continued

```
misc_feature            1..40
                        note = Synthetic
source                  1..40
                        mol_type = other RNA
                        organism = synthetic construct
SEQUENCE: 169
tacgccaaag tggagcccac tcgtacccca tcatgagctg                              40

SEQ ID NO: 170          moltype = RNA  length = 41
FEATURE                 Location/Qualifiers
misc_feature            1..41
                        note = Synthetic
source                  1..41
                        mol_type = other RNA
                        organism = synthetic construct
SEQUENCE: 170
tacgccaaag tggagcccac tcgtacccca tcatgagcct g                            41

SEQ ID NO: 171          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 171
tacgccaaag tggagcccac tcgtacccca tcatgagctc                              40

SEQ ID NO: 172          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 172
tacgccaaag tggagcccac tcgtacccca tcatgggctg                              40

SEQ ID NO: 173          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 173
tacgccaaag tggagcccac tcgtatccca tcatgagctg                              40

SEQ ID NO: 174          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 174
tacgccaaag tggagcccac tcgtacccca tcgtgagctg                              40

SEQ ID NO: 175          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 175
tacgccaaag tggagcccac tcgtactcca tcatgagctg                              40

SEQ ID NO: 176          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 176
cacgccaaag tggagcccac tcgtacccca tcatgagctg                              40

SEQ ID NO: 177          moltype = RNA  length = 40
```

-continued

```
FEATURE                 Location/Qualifiers
misc_feature            1..40
                        note = Synthetic
source                  1..40
                        mol_type = other RNA
                        organism = synthetic construct
SEQUENCE: 177
tacgccaaag tggagcccac tcgcacccca tcatgagctg                              40

SEQ ID NO: 178          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 178
tacgccaaag tggagcccac tcgtacccca tcatgagcta                              40

SEQ ID NO: 179          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 179
ccgccagctt tgggtaccct gaccaattca cggccatcca                              40

SEQ ID NO: 180          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 180
ccgccagctt tgggtaccct gaccaattca cggccatccg                              40

SEQ ID NO: 181          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 181
ccgcccagct ttgggtaccc tgaccaattc acggccatcc a                            41

SEQ ID NO: 182          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 182
gtaattgtct gagaccaccg gacaatcaac aagaaatcct                              40

SEQ ID NO: 183          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 183
gtaattgtct gagaccaccg gacaatcaac aagaaaatcc t                            41

SEQ ID NO: 184          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 184
taattgtctg agaccaccgg acaatcaaca agaaatcct                               39
```

```
SEQ ID NO: 185            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 185
tcaggccaaa gtgtgatagc cacacccgca cccatcagga                              40

SEQ ID NO: 186            moltype = RNA   length = 39
FEATURE                   Location/Qualifiers
misc_feature              1..39
                          note = Synthetic
source                    1..39
                          mol_type = other RNA
                          organism = synthetic construct
SEQUENCE: 186
tcaggccaaa gtgtgatagc cacacccgca cccatcaga                               39

SEQ ID NO: 187            moltype = RNA   length = 39
FEATURE                   Location/Qualifiers
misc_feature              1..39
                          note = Synthetic
source                    1..39
                          mol_type = other RNA
                          organism = synthetic construct
SEQUENCE: 187
tcaggccaaa gtgtgatagc cacacccgca cccatcagg                               39

SEQ ID NO: 188            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 188
ccgaccgccg accagggtgc cactcgtacc cctgtccgcc                              40

SEQ ID NO: 189            moltype = RNA   length = 41
FEATURE                   Location/Qualifiers
misc_feature              1..41
                          note = Synthetic
source                    1..41
                          mol_type = other RNA
                          organism = synthetic construct
SEQUENCE: 189
ccgaccgccg accagggtgc cactcgtacc cctgtccgcc c                            41

SEQ ID NO: 190            moltype = RNA   length = 41
FEATURE                   Location/Qualifiers
misc_feature              1..41
                          note = Synthetic
source                    1..41
                          mol_type = other RNA
                          organism = synthetic construct
SEQUENCE: 190
ccgaccgccg accagggtgc cactcgtacc cctgtcccgc c                            41

SEQ ID NO: 191            moltype = RNA   length = 39
FEATURE                   Location/Qualifiers
misc_feature              1..39
                          note = Synthetic
source                    1..39
                          mol_type = other RNA
                          organism = synthetic construct
SEQUENCE: 191
ccgaccgccg accagggtgc cactcgtacc cctgtccgc                               39

SEQ ID NO: 192            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 192
tgccaagtcg aagcccgacc acgccatccc taacagtgcc                              40
```

```
SEQ ID NO: 193         moltype = RNA   length = 41
FEATURE                Location/Qualifiers
misc_feature           1..41
                       note = Synthetic
source                 1..41
                       mol_type = other RNA
                       organism = synthetic construct
SEQUENCE: 193
tgccaaagtc gaagcccgac cacgccatcc ctaacagtgc c                    41

SEQ ID NO: 194         moltype = RNA   length = 39
FEATURE                Location/Qualifiers
misc_feature           1..39
                       note = Synthetic
source                 1..39
                       mol_type = other RNA
                       organism = synthetic construct
SEQUENCE: 194
tgccaagtcg aagcccgacc acgccatccc taacagtgc                       39

SEQ ID NO: 195         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 195
tgccaagtcg aagcccgacc acgccatccc taacggtgcc                      40

SEQ ID NO: 196         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 196
tgccaagtcg aagcccgacc acgccatccc taacagtgca                      40

SEQ ID NO: 197         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 197
tgccaagtcg aggcccgacc acgccatccc taacagtgcc                      40

SEQ ID NO: 198         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 198
tgccaagccg aagcccgacc acgccatccc taacagtgcc                      40

SEQ ID NO: 199         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 199
acttgtgctg agtcgccaaa gtgaggccca ctcgccagca                      40

SEQ ID NO: 200         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 200
```

```
gcttgtgctg agtcgccaaa gtgaggccca ctcgccagca                              40

SEQ ID NO: 201           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 201
acctgtgctg agtcgccaaa gtgaggccca ctcgccagca                              40

SEQ ID NO: 202           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 202
ccgccagctc ctctgaggca caagaggttc acggtgatcc                              40

SEQ ID NO: 203           moltype = RNA   length = 41
FEATURE                  Location/Qualifiers
misc_feature             1..41
                         note = Synthetic
source                   1..41
                         mol_type = other RNA
                         organism = synthetic construct
SEQUENCE: 203
ccgccagctc ctctgaggca caagaggttc acggtgatcc c                            41

SEQ ID NO: 204           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 204
caccaggttc tgctgtcccc aagcgctgac ccatccttcc                              40

SEQ ID NO: 205           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 205
caccaggttc tgctatcccc aagcgctgac ccatccttcc                              40

SEQ ID NO: 206           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 206
caccaggttc tgctgtctcc aagcgctgac ccatccttcc                              40

SEQ ID NO: 207           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 207
caccaggttc tgctgttccc aagcgctgac ccatccttcc                              40

SEQ ID NO: 208           moltype = RNA   length = 40
FEATURE                  Location/Qualifiers
misc_feature             1..40
                         note = Synthetic
source                   1..40
                         mol_type = other RNA
                         organism = synthetic construct
```

```
SEQUENCE: 208
caccaggtcc tgctgtcccc aagcgctgac ccatccttcc                                40

SEQ ID NO: 209          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 209
caccaggctc tgctgtcccc aagcgctgac ccatccttcc                                40

SEQ ID NO: 210          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 210
caccaggttc tgctgtcctc aagcgctgac ccatccttcc                                40

SEQ ID NO: 211          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 211
aagatccggt aactccccac cgcaatcacc gtcgactact                                 40

SEQ ID NO: 212          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 212
aagatccggt gactccccac cgcaatcacc gtcgactact                                 40

SEQ ID NO: 213          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 213
aagatccggt aactccctac cgcaatcacc gtcgactact                                 40

SEQ ID NO: 214          moltype = RNA  length = 41
FEATURE                 Location/Qualifiers
misc_feature            1..41
                        note = Synthetic
source                  1..41
                        mol_type = other RNA
                        organism = synthetic construct
SEQUENCE: 214
aaagatccgg taactcccca ccgcaatcac cgtcgactac t                              41

SEQ ID NO: 215          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 215
ccatctagat ctccgtagat tccccccggc tctttctcgc                                 40

SEQ ID NO: 216          moltype = RNA  length = 40
FEATURE                 Location/Qualifiers
misc_feature            1..40
                        note = Synthetic
source                  1..40
                        mol_type = other RNA
```

```
                              organism = synthetic construct
SEQUENCE: 216
ccatctagat ctccgtagat tcccccgggc tctttctcgt                     40

SEQ ID NO: 217         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 217
ccatctagat ctccgtagat tcccccgggc tctttctcga                     40

SEQ ID NO: 218         moltype = RNA   length = 39
FEATURE                Location/Qualifiers
misc_feature           1..39
                       note = Synthetic
source                 1..39
                       mol_type = other RNA
                       organism = synthetic construct
SEQUENCE: 218
ccatctagat ctccgtagat tcccccgggc tctttctcg                      39

SEQ ID NO: 219         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 219
ccatctagat ctccgtagat tcccccgggc tctttctcgc                     40

SEQ ID NO: 220         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 220
ccatctagat ctccgtagat tcccccgggc tctttctcac                     40

SEQ ID NO: 221         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 221
ccatctagat ctccgtagat ttcccccggc tctttctcgc                     40

SEQ ID NO: 222         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 222
ccatctagat ctccgtagat tcccccgggc tcttcctcgc                     40

SEQ ID NO: 223         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 223
ccatctagat ctccgtagat tcccccgggc tctctctcgc                     40

SEQ ID NO: 224         moltype = RNA   length = 40
FEATURE                Location/Qualifiers
misc_feature           1..40
                       note = Synthetic
source                 1..40
```

```
                        mol_type = other RNA
                        organism = synthetic construct
SEQUENCE: 224
ccatctagat ctccgtagat tcccccgggc tctttcttgc                            40

SEQ ID NO: 225          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 225
ccatctagat ctccgtagat tcccccgggc cctttctcgc                            40

SEQ ID NO: 226          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 226
ccatctagat ctccgtagat tcccccgggc tctttctctc                            40

SEQ ID NO: 227          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 227
ccatctagat ctccgtagat tcccccggcc tctttctcgc                            40

SEQ ID NO: 228          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 228
ccatctagat ctccgtagat tcccccgggc tctttctccc                            40

SEQ ID NO: 229          moltype = RNA  length = 41
FEATURE                 Location/Qualifiers
misc_feature            1..41
                        note = Synthetic
source                  1..41
                        mol_type = other RNA
                        organism = synthetic construct
SEQUENCE: 229
ccatctagat ctccgtagat tcccccgggc tctttctcgt c                          41

SEQ ID NO: 230          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 230
ccatctgaac ccacagattc ccccatcatc agccacagtg                            40

SEQ ID NO: 231          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 231
ccatctgaac ccacagattc ccccatcatc agccacagta                            40

SEQ ID NO: 232          moltype = RNA  length = 40
FEATURE                 Location/Qualifiers
misc_feature            1..40
                        note = Synthetic
```

```
source                      1..40
                            mol_type = other RNA
                            organism = synthetic construct
SEQUENCE: 232
ccatctgaac ccacagattc ccccatcatc agccacagcg                              40

SEQ ID NO: 233              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 233
ccatctgaac ccacagattc ccccatcatc agccacagtc                              40

SEQ ID NO: 234              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 234
ccatctgaac ccacagattc ccccatcatc agccacggtg                              40

SEQ ID NO: 235              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 235
cactaagttg gtagccccaa ctgccccgac acgaggatgt                              40

SEQ ID NO: 236              moltype = RNA   length = 41
FEATURE                     Location/Qualifiers
misc_feature                1..41
                            note = Synthetic
source                      1..41
                            mol_type = other RNA
                            organism = synthetic construct
SEQUENCE: 236
cactaagttg gtagccccaa ctgccccgac acgaggatgt c                            41

SEQ ID NO: 237              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 237
cactaagttg gtagccccaa ctgccccgac acgaggatgc                              40

SEQ ID NO: 238              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 238
ttgtgctccg tggctccccg gaccaaccgc ttccagcagt                              40

SEQ ID NO: 239              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 239
ttgtgttccg tggctccccg gaccaaccgc ttccagcagt                              40

SEQ ID NO: 240              moltype = RNA   length = 40
FEATURE                     Location/Qualifiers
misc_feature                1..40
```

```
                        note = Synthetic
source                  1..40
                        mol_type = other RNA
                        organism = synthetic construct
SEQUENCE: 240
ttgtgctccg tggctccccg gaccaaccgc ttccagcagc                              40

SEQ ID NO: 241          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 241
ttgcgctccg tggctccccg gaccaaccgc ttccagcagt                              40

SEQ ID NO: 242          moltype = RNA  length = 39
FEATURE                 Location/Qualifiers
misc_feature            1..39
                        note = Synthetic
source                  1..39
                        mol_type = other RNA
                        organism = synthetic construct
SEQUENCE: 242
caatcacgcg tagtacgtcg cggaagatcc ccatgccga                               39

SEQ ID NO: 243          moltype = RNA  length = 39
FEATURE                 Location/Qualifiers
misc_feature            1..39
                        note = Synthetic
source                  1..39
                        mol_type = other RNA
                        organism = synthetic construct
SEQUENCE: 243
caatcacgcg tagtacgtcg cggaagatcc ccatgccgg                               39

SEQ ID NO: 244          moltype = RNA  length = 39
FEATURE                 Location/Qualifiers
misc_feature            1..39
                        note = Synthetic
source                  1..39
                        mol_type = other RNA
                        organism = synthetic construct
SEQUENCE: 244
caatcacgcg tagtacgtcg cggaagatcc ccatgccaa                               39

SEQ ID NO: 245          moltype = RNA  length = 39
FEATURE                 Location/Qualifiers
misc_feature            1..39
                        note = Synthetic
source                  1..39
                        mol_type = other RNA
                        organism = synthetic construct
SEQUENCE: 245
caatcacgcg tagtacgtcg cggaagatcc ccatgccgt                               39

SEQ ID NO: 246          moltype = RNA  length = 39
FEATURE                 Location/Qualifiers
misc_feature            1..39
                        note = Synthetic
source                  1..39
                        mol_type = other RNA
                        organism = synthetic construct
SEQUENCE: 246
caatcacgcg tagcacgtcg cggaagatcc ccatgccga                               39

SEQ ID NO: 247          moltype = RNA  length = 39
FEATURE                 Location/Qualifiers
misc_feature            1..39
                        note = Synthetic
source                  1..39
                        mol_type = other RNA
                        organism = synthetic construct
SEQUENCE: 247
caatcacgcg tagtacgtcg cggaggatcc ccatgccga                               39

SEQ ID NO: 248          moltype = RNA  length = 39
FEATURE                 Location/Qualifiers
```

```
                        misc_feature            1..39
                                                note = Synthetic
                        source                  1..39
                                                mol_type = other RNA
                                                organism = synthetic construct
                        SEQUENCE: 248
                        cacatggtac gcccaaaagc gaggcccgct gcgtagtgc                              39

SEQ ID NO: 249          moltype = RNA   length = 39
                        FEATURE                 Location/Qualifiers
                        misc_feature            1..39
                                                note = Synthetic
                        source                  1..39
                                                mol_type = other RNA
                                                organism = synthetic construct
                        SEQUENCE: 249
                        cacatggtac gccccaaagc gaggcccgct gcgtagtgc                              39

SEQ ID NO: 250          moltype = RNA   length = 39
                        FEATURE                 Location/Qualifiers
                        misc_feature            1..39
                                                note = Synthetic
                        source                  1..39
                                                mol_type = other RNA
                                                organism = synthetic construct
                        SEQUENCE: 250
                        cacatggtac gcccaaagcc gaggcccgct gcgtagtgc                              39

SEQ ID NO: 251          moltype = RNA   length = 38
                        FEATURE                 Location/Qualifiers
                        misc_feature            1..38
                                                note = Synthetic
                        source                  1..38
                                                mol_type = other RNA
                                                organism = synthetic construct
                        SEQUENCE: 251
                        cacatggtac gcccaaaagc gaggcccgct gcgtagtg                               38

SEQ ID NO: 252          moltype = RNA   length = 40
                        FEATURE                 Location/Qualifiers
                        misc_feature            1..40
                                                note = Synthetic
                        source                  1..40
                                                mol_type = other RNA
                                                organism = synthetic construct
                        SEQUENCE: 252
                        tgccatacgc ggttcgaagt cgaagcccga caacccggca                             40

SEQ ID NO: 253          moltype = RNA   length = 41
                        FEATURE                 Location/Qualifiers
                        misc_feature            1..41
                                                note = Synthetic
                        source                  1..41
                                                mol_type = other RNA
                                                organism = synthetic construct
                        SEQUENCE: 253
                        tgccatacgc ggttcgaagt cgaagcccga caacccggc a                            41

SEQ ID NO: 254          moltype = RNA   length = 40
                        FEATURE                 Location/Qualifiers
                        misc_feature            1..40
                                                note = Synthetic
                        source                  1..40
                                                mol_type = other RNA
                                                organism = synthetic construct
                        SEQUENCE: 254
                        tgccatacgc ggttcgaagt cgaggcccga caacccggca                             40

SEQ ID NO: 255          moltype = RNA   length = 40
                        FEATURE                 Location/Qualifiers
                        misc_feature            1..40
                                                note = Synthetic
                        source                  1..40
                                                mol_type = other RNA
                                                organism = synthetic construct
                        SEQUENCE: 255
                        gttattcaca tgcctcccgt gaatcaacaa gaattccttg                             40

SEQ ID NO: 256          moltype = RNA   length = 39
```

```
FEATURE              Location/Qualifiers
misc_feature         1..39
                     note = Synthetic
source               1..39
                     mol_type = other RNA
                     organism = synthetic construct
SEQUENCE: 256
ttattcacat gcctcccgtg aatcaacaag aattccttg                              39

SEQ ID NO: 257       moltype = RNA   length = 40
FEATURE              Location/Qualifiers
misc_feature         1..40
                     note = Synthetic
source               1..40
                     mol_type = other RNA
                     organism = synthetic construct
SEQUENCE: 257
gttattcaca tgcctcccgt gaatcaacaa gaattcctcg                             40

SEQ ID NO: 258       moltype = RNA   length = 40
FEATURE              Location/Qualifiers
misc_feature         1..40
                     note = Synthetic
source               1..40
                     mol_type = other RNA
                     organism = synthetic construct
SEQUENCE: 258
gttattcaca tgcctctcgt gaatcaacaa gaattccttg                             40

SEQ ID NO: 259       moltype =    length =
SEQUENCE: 259
000

SEQ ID NO: 260       moltype = RNA   length = 40
FEATURE              Location/Qualifiers
misc_feature         1..40
                     note = Synthetic
source               1..40
                     mol_type = other RNA
                     organism = synthetic construct
SEQUENCE: 260
aaagatctag actgtaagtc tccaatcgcc cagttaattc                             40

SEQ ID NO: 261       moltype = RNA   length = 41
FEATURE              Location/Qualifiers
misc_feature         1..41
                     note = Synthetic
source               1..41
                     mol_type = other RNA
                     organism = synthetic construct
SEQUENCE: 261
aaaagatcta gactgtaagt ctccaatcgc ccagttaatt c                           41

SEQ ID NO: 262       moltype = RNA   length = 39
FEATURE              Location/Qualifiers
misc_feature         1..39
                     note = Synthetic
source               1..39
                     mol_type = other RNA
                     organism = synthetic construct
SEQUENCE: 262
aaagatctag actgtaagtc tccaatcgcc cagtaattc                              39

SEQ ID NO: 263       moltype = RNA   length = 39
FEATURE              Location/Qualifiers
misc_feature         1..39
                     note = Synthetic
source               1..39
                     mol_type = other RNA
                     organism = synthetic construct
SEQUENCE: 263
gcccaatcgc cagtggaacg cgctgaagga tctgcaccc                              39

SEQ ID NO: 264       moltype = RNA   length = 38
FEATURE              Location/Qualifiers
misc_feature         1..38
                     note = Synthetic
source               1..38
                     mol_type = other RNA
```

```
                         organism = synthetic construct
SEQUENCE: 264
gcccaatcgc cagtggaacg cgctgaagga tctgcacc                              38

SEQ ID NO: 265           moltype = RNA   length = 39
FEATURE                  Location/Qualifiers
misc_feature             1..39
                         note = Synthetic
source                   1..39
                         mol_type = other RNA
                         organism = synthetic construct
SEQUENCE: 265
gcccaatcgc cagtggaacg cactgaagga tctgcaccc                             39

SEQ ID NO: 266           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 266
gcccaatcgc cagtggaacg cgctgaagga tctgcacccc                            40

SEQ ID NO: 267           moltype = RNA   length = 38
FEATURE                  Location/Qualifiers
misc_feature             1..38
                         note = Synthetic
source                   1..38
                         mol_type = other RNA
                         organism = synthetic construct
SEQUENCE: 267
cccaatcgcc agtggaacgc gctgaaggat ctgcaccc                              38

SEQ ID NO: 268           moltype = RNA   length = 39
FEATURE                  Location/Qualifiers
misc_feature             1..39
                         note = Synthetic
source                   1..39
                         mol_type = other RNA
                         organism = synthetic construct
SEQUENCE: 268
gcccaatcgc cagcggaacg cgctgaagga tctgcaccc                             39

SEQ ID NO: 269           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 269
tgcaacgtaa aagagagtca tctcaggcta gtcgtctacc                            40

SEQ ID NO: 270           moltype = RNA   length = 39
FEATURE                  Location/Qualifiers
misc_feature             1..39
                         note = Synthetic
source                   1..39
                         mol_type = other RNA
                         organism = synthetic construct
SEQUENCE: 270
tgcaacgtaa aagagagtca tctcaggcta gtcgtctac                             39

SEQ ID NO: 271           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 271
gtgtacgcca agtcgaggcc cgaccgtacc catacgcgac                            40

SEQ ID NO: 272           moltype = RNA   length = 39
FEATURE                  Location/Qualifiers
misc_feature             1..39
                         note = Synthetic
source                   1..39
```

```
                        mol_type = other RNA
                        organism = synthetic construct
SEQUENCE: 272
tgtacgccaa gtcgaggccc gaccgtaccc atacgcgac                          39

SEQ ID NO: 273          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 273
gtgtacgcca agtcgaggcc cgaccgtacc catacgcggc                         40

SEQ ID NO: 274          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 274
gtgtacgcca agtcgaggcc cgaccgtacc catacgcgat                         40

SEQ ID NO: 275          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 275
ttagctctac tttcctcttc agtaagacta accgcttctt                         40

SEQ ID NO: 276          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 276
ttagctctac tttcctcttc agtaagacta accgcttcct                         40

SEQ ID NO: 277          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 277
ttagctctac tttcctcttc agtaagacta accgcttctc                         40

SEQ ID NO: 278          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 278
ttagctctac tttcctcttc agtaagacta accgctcctt                         40

SEQ ID NO: 279          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 279
tccaagcgga ggccccgcac ccaccctcca acgggcacgg                         40

SEQ ID NO: 280          moltype = RNA  length = 40
FEATURE                 Location/Qualifiers
misc_feature            1..40
                        note = Synthetic
```

```
source                    1..40
                          mol_type = other RNA
                          organism = synthetic construct
SEQUENCE: 280
tccaagcgga ggccccgcac ccaccctcca acgggcacgc                         40

SEQ ID NO: 281            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 281
tccaagcgga ggccccgtac ccaccctcca acgggcacgg                         40

SEQ ID NO: 282            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 282
tccaagcgga ggccccgcac ccaccccca acgggcacgg                          40

SEQ ID NO: 283            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 283
tccaagcgga ggccccgcac ccaccctcca acgggcacga                         40

SEQ ID NO: 284            moltype = RNA   length = 41
FEATURE                   Location/Qualifiers
misc_feature              1..41
                          note = Synthetic
source                    1..41
                          mol_type = other RNA
                          organism = synthetic construct
SEQUENCE: 284
tccaaagcgg aggccccgca cccaccctcc aacgggcacg g                       41

SEQ ID NO: 285            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 285
tccaagcgga ggccccgcac ccaccctcca acgggcacag                         40

SEQ ID NO: 286            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 286
tatcgctcca caacgactcc cgtggactac ccaattccaa                         40

SEQ ID NO: 287            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 287
tatcgctcca caacgactcc cgtggactac ccaattccag                         40

SEQ ID NO: 288            moltype = RNA   length = 41
FEATURE                   Location/Qualifiers
misc_feature              1..41
```

```
                              note = Synthetic
source                        1..41
                              mol_type = other RNA
                              organism = synthetic construct
SEQUENCE: 288
tatcgctcca caacgactcc cgtggactac ccaattccaa a                    41

SEQ ID NO: 289           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 289
tatcgctcca caacgactcc cgtggactac ccaattccat                      40

SEQ ID NO: 290           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 290
gtcgtgccca agtgaaggcc tcacgcacgc atcctaacct                      40

SEQ ID NO: 291           moltype = RNA   length = 39
FEATURE                  Location/Qualifiers
misc_feature             1..39
                         note = Synthetic
source                   1..39
                         mol_type = other RNA
                         organism = synthetic construct
SEQUENCE: 291
tcgtgcccaa gtgaaggcct cacgcacgca tcctaacct                       39

SEQ ID NO: 292           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 292
gtcgtgccca agtgaaggcc tcacgcacgc atcctaaccc                      40

SEQ ID NO: 293           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 293
aagatctgcg ccagcacaat caccatcgtc ctgagaatgg                      40

SEQ ID NO: 294           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 294
aagatctgcg ccagcacaat caccatcgtc ctgagaatgc                      40

SEQ ID NO: 295           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 295
aagatctgcg ccagcacaat caccatcgtc ctgagaatga                      40

SEQ ID NO: 296           moltype = RNA   length = 40
FEATURE                  Location/Qualifiers
```

```
misc_feature            1..40
                        note = Synthetic
source                  1..40
                        mol_type = other RNA
                        organism = synthetic construct
SEQUENCE: 296
aagatctgcg ccagcacaat caccatcgtc ctgagagtgg                              40

SEQ ID NO: 297          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 297
aagatctgcg ccagcacaat caccatcgtc ctgggaatgg                              40

SEQ ID NO: 298          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 298
atgccaagca gtggccctgc cacccaccta tcactgtcga                              40

SEQ ID NO: 299          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 299
atgccaagca gtcggcctgc cacccaccta tcactgtcga                              40

SEQ ID NO: 300          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 300
atgccaagca gtggccctgc cacccaccta tcactatcga                              40

SEQ ID NO: 301          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 301
atgccaagca gtggccctgc cacccaccta ccactgtcga                              40

SEQ ID NO: 302          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 302
atgccaagca gcggccctgc cacccaccta tcactgtcga                              40

SEQ ID NO: 303          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 303
aacagaccaa gcagcggccc tgctctgcca tcatacgcct                              40

SEQ ID NO: 304          moltype = RNA  length = 40
```

```
FEATURE                 Location/Qualifiers
misc_feature            1..40
                        note = Synthetic
source                  1..40
                        mol_type = other RNA
                        organism = synthetic construct
SEQUENCE: 304
gacagaccaa gcagcggccc tgctctgcca tcatacgcct                          40

SEQ ID NO: 305          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 305
aacagaccaa gcagtggccc tgctctgcca tcatacgcct                          40

SEQ ID NO: 306          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 306
aacagaccaa gcagcggccc tgctctgcca tcatacgccc                          40

SEQ ID NO: 307          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 307
aacagaccaa gcagcggccc tgctctgcca tcatacacct                          40

SEQ ID NO: 308          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 308
acagaccaag cagcggccct gctctgccat catacgcct                           39

SEQ ID NO: 309          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 309
aacagaccaa gcagcggccc tgctctgcca tcatacgccc t                        41

SEQ ID NO: 310          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 310
gtcattcgct gacgaatcaa catgaattcc taactgctga                          40

SEQ ID NO: 311          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 311
tcattcgctg acgaatcaac atgaattcct aactgctga                           39
```

-continued

```
SEQ ID NO: 312            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 312
gtcattcgct gacgaatcaa catgaattcc taactgccga                              40

SEQ ID NO: 313            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 313
gtcattcgct gacgaatcaa catgaattcc taactgctgg                              40

SEQ ID NO: 314            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 314
acacgccaag ctggtagccc cagccgtgcc cattacggcc                              40

SEQ ID NO: 315            moltype = RNA   length = 39
FEATURE                   Location/Qualifiers
misc_feature              1..39
                          note = Synthetic
source                    1..39
                          mol_type = other RNA
                          organism = synthetic construct
SEQUENCE: 315
acacgccaag ctggtagccc cagccgtgcc cattacggc                               39

SEQ ID NO: 316            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 316
acacgccaag ctggtagccc cagccgtgcc cattacggtc                              40

SEQ ID NO: 317            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 317
acacgccaag ctggtagccc cagccgtacc cattacggcc                              40

SEQ ID NO: 318            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 318
tagccaagca gcagccctgc caacccatcc tacccgggcg                              40

SEQ ID NO: 319            moltype = RNA   length = 39
FEATURE                   Location/Qualifiers
misc_feature              1..39
                          note = Synthetic
source                    1..39
                          mol_type = other RNA
                          organism = synthetic construct
SEQUENCE: 319
tagccaagca gcagccctgc caacccatcc tacccggcg                               39
```

```
SEQ ID NO: 320          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 320
tagccaagca gcagccctgc caacccatcc tacccgggca                              40

SEQ ID NO: 321          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 321
tagccaagca gcagccctgc caacccatcc tacccgggtg                              40

SEQ ID NO: 322          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 322
tagccaagca gcggccctgc caacccatcc tacccgggcg                              40

SEQ ID NO: 323          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 323
gcccaaggcg aggcccgccg ctccatccag acgctgaggg                              40

SEQ ID NO: 324          moltype = RNA    length = 39
FEATURE                 Location/Qualifiers
misc_feature            1..39
                        note = Synthetic
source                  1..39
                        mol_type = other RNA
                        organism = synthetic construct
SEQUENCE: 324
gcccaaggcg aggcccgccg ctccatccag acgctgagg                               39

SEQ ID NO: 325          moltype = RNA    length = 39
FEATURE                 Location/Qualifiers
misc_feature            1..39
                        note = Synthetic
source                  1..39
                        mol_type = other RNA
                        organism = synthetic construct
SEQUENCE: 325
cccaaggcga ggcccgccgc tccatccaga cgctgaggg                               39

SEQ ID NO: 326          moltype = RNA    length = 38
FEATURE                 Location/Qualifiers
misc_feature            1..38
                        note = Synthetic
source                  1..38
                        mol_type = other RNA
                        organism = synthetic construct
SEQUENCE: 326
cccaaggcga ggcccgccgc tccatccaga cgctgagg                                38

SEQ ID NO: 327          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 327
```

```
gcccaaggcg aggcccgccg ctccatccag acgctgaggc                                 40

SEQ ID NO: 328          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 328
gcccaaggc gaggcccgcc gctccatcca gacgctgagg g                                 41

SEQ ID NO: 329          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 329
gcccaaggcg aggcccgccg ctccatccag acgctgagga                                 40

SEQ ID NO: 330          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 330
gccccaaggc gaggcccgcc gctccatcca gacgctgagg g                               41

SEQ ID NO: 331          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 331
aagatctcgt catgctttga cgtcaatcac cattgttccc                                 40

SEQ ID NO: 332          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 332
aagatctcgt catgctttga cgtcaatcac cattgttcc                                  39

SEQ ID NO: 333          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 333
aagatctcgt catgctttga cgccaatcac cattgttccc                                 40

SEQ ID NO: 334          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 334
aagatctcgt catgctttga cgtcaatcac cattgttcca                                 40

SEQ ID NO: 335          moltype = RNA   length = 40
FEATURE                 Location/Qualifiers
misc_feature            1..40
                        note = Synthetic
source                  1..40
                        mol_type = other RNA
                        organism = synthetic construct
```

```
SEQUENCE: 335
aagatctcgt catgctttga cgtcaatcac cattgttcct                    40

SEQ ID NO: 336         moltype = RNA  length = 41
FEATURE                Location/Qualifiers
misc_feature           1..41
                       note = Synthetic
source                 1..41
                       mol_type = other RNA
                       organism = synthetic construct
SEQUENCE: 336
aagatctcgt catgctttga cgtcaatcac cattgttccc c                  41

SEQ ID NO: 337         moltype = RNA  length = 41
FEATURE                Location/Qualifiers
misc_feature           1..41
                       note = Synthetic
source                 1..41
                       mol_type = other RNA
                       organism = synthetic construct
SEQUENCE: 337
aaagatctcg tcatgctttg acgtcaatca ccattgttcc c                  41

SEQ ID NO: 338         moltype = RNA  length = 40
FEATURE                Location/Qualifiers
misc_feature           1..40
                       note = Synthetic
source                 1..40
                       mol_type = other RNA
                       organism = synthetic construct
SEQUENCE: 338
aagatctcgt catgccttga cgtcaatcac cattgttccc                    40

SEQ ID NO: 339         moltype = RNA  length = 39
FEATURE                Location/Qualifiers
misc_feature           1..39
                       note = Synthetic
source                 1..39
                       mol_type = other RNA
                       organism = synthetic construct
SEQUENCE: 339
atcccccagg atgagcacgt tgccatggac tggctatcc                     39

SEQ ID NO: 340         moltype = RNA  length = 38
FEATURE                Location/Qualifiers
misc_feature           1..38
                       note = Synthetic
source                 1..38
                       mol_type = other RNA
                       organism = synthetic construct
SEQUENCE: 340
atccccagga tgagcacgtt gccatggact ggctatcc                      38

SEQ ID NO: 341         moltype = RNA  length = 40
FEATURE                Location/Qualifiers
misc_feature           1..40
                       note = Synthetic
source                 1..40
                       mol_type = other RNA
                       organism = synthetic construct
SEQUENCE: 341
ctgttacagt ctcgcgtaac cccccatcg atgtcctcga                     40

SEQ ID NO: 342         moltype = RNA  length = 40
FEATURE                Location/Qualifiers
misc_feature           1..40
                       note = Synthetic
source                 1..40
                       mol_type = other RNA
                       organism = synthetic construct
SEQUENCE: 342
ctgttacagt ctcgcgtaac cccccatcg atgtcctcgg                     40

SEQ ID NO: 343         moltype = RNA  length = 40
FEATURE                Location/Qualifiers
misc_feature           1..40
                       note = Synthetic
source                 1..40
                       mol_type = other RNA
```

```
                        organism = synthetic construct
SEQUENCE: 343
ctgttacagt ctcgagtaac cccccatcg atgtcctcga                              40

SEQ ID NO: 344          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 344
ctgttacagt ctcgcgtaac ccctccatcg atgtcctcga                             40

SEQ ID NO: 345          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 345
ctgttacagc ctcgcgtaac cccccatcg atgtcctcga                              40

SEQ ID NO: 346          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 346
ctgttacagt ctcccgtaac cccccatcg atgtcctcga                              40

SEQ ID NO: 347          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 347
agccagcttt cggcaaaccg aattcactcc accctgctca                             40

SEQ ID NO: 348          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 348
agccagcttt cggcaaaccg aattcactcc accctcctca                             40

SEQ ID NO: 349          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 349
agccagcttt cggcaaaccg aattcactcc gccctgctca                             40

SEQ ID NO: 350          moltype = RNA   length = 38
FEATURE                 Location/Qualifiers
misc_feature            1..38
                        note = Synthetic
source                  1..38
                        mol_type = other RNA
                        organism = synthetic construct
SEQUENCE: 350
agccagcttt cggcaaaccg aattcactcc accctgct                               38

SEQ ID NO: 351          moltype = RNA   length = 40
FEATURE                 Location/Qualifiers
misc_feature            1..40
                        note = Synthetic
source                  1..40
```

```
                            mol_type = other RNA
                            organism = synthetic construct
SEQUENCE: 351
agccagcttt cggcgaaccg aattcactcc accctgctca                         40

SEQ ID NO: 352          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 352
agccagcttt cggcaaaccg aattcactcc accctgctcg                         40

SEQ ID NO: 353          moltype = RNA   length = 39
FEATURE                 Location/Qualifiers
misc_feature            1..39
                        note = Synthetic
source                  1..39
                        mol_type = other RNA
                        organism = synthetic construct
SEQUENCE: 353
agccagcttt cggcaaaccg aattcactcc accctgctc                          39

SEQ ID NO: 354          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 354
agccagcttt cggcaaaccg aattcactcc accctgcaca                         40

SEQ ID NO: 355          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 355
cacggtataa cctcctcata tacctgctgt gccacccgcg                         40

SEQ ID NO: 356          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 356
cacggtataa cctcctcata tacctgctgt gccacccgca                         40

SEQ ID NO: 357          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 357
cacggtataa cctcctcata tacctgctgt gccacccacc g                       41

SEQ ID NO: 358          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 358
cacggtataa cctcctcata tacctgctgt gccacccgct                         40

SEQ ID NO: 359          moltype = RNA   length = 40
FEATURE                 Location/Qualifiers
misc_feature            1..40
                        note = Synthetic
```

```
                          -continued source                    1..40
                          mol_type = other RNA
                          organism = synthetic construct
SEQUENCE: 359
cacggtataa cctcctcata tacctgctgt gccacccacg              40

SEQ ID NO: 360            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 360
cacggtataa cctcctcata tacctgctgt gccacccgtg              40

SEQ ID NO: 361            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 361
cacggtataa cctcctcata tacctgctgt gccgcccgcg              40

SEQ ID NO: 362            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 362
ccggaagatc tgctcgcact agccggagcc caatcacggc              40

SEQ ID NO: 363            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 363
ccggaagatc tgctcgcact agtcggagcc caatcacggc              40

SEQ ID NO: 364            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 364
ccggaggatc tgctcgcact agccggagcc caatcacggc              40

SEQ ID NO: 365            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 365
ccggaagatc tgctcgcatt agccggagcc caatcacggc              40

SEQ ID NO: 366            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 366
cctgccgaac ggctaagtcg cagcccgacc cgcggcaggg              40

SEQ ID NO: 367            moltype = RNA   length = 39
FEATURE                   Location/Qualifiers
misc_feature              1..39
```

```
                        note = Synthetic
source                  1..39
                        mol_type = other RNA
                        organism = synthetic construct
SEQUENCE: 367
cctgccgaac ggctaagtcg cagcccgacc cgcggcagg                          39

SEQ ID NO: 368          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 368
cctgccgaac ggctaagtcg cagcccgacc cgcggcagga                         40

SEQ ID NO: 369          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 369
cctgccgaac ggccaagtcg cagcccgacc cgcggcaggg                         40

SEQ ID NO: 370          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 370
cctgccgaac ggctaagtcg cggcccgacc cgcggcaggg                         40

SEQ ID NO: 371          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 371
ctccgacccg cggacgaagt caacttccac agtcccacac                         40

SEQ ID NO: 372          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 372
ctccgacccg cggacgaagt caacttccac agtcccacaa                         40

SEQ ID NO: 373          moltype = RNA  length = 42
FEATURE                 Location/Qualifiers
misc_feature            1..42
                        note = Synthetic
source                  1..42
                        mol_type = other RNA
                        organism = synthetic construct
SEQUENCE: 373
ctccgacccg cggacgaagt caacttccac agtcccacac ac                      42

SEQ ID NO: 374          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 374
ctccgacccg cggacgaagt caacttccac agtctcacac                         40

SEQ ID NO: 375          moltype = RNA  length = 40
FEATURE                 Location/Qualifiers
```

```
                        misc_feature         1..40
                                             note = Synthetic
                        source               1..40
                                             mol_type = other RNA
                                             organism = synthetic construct
                        SEQUENCE: 375
                        ctccgacccg cggacgaagt caacttccac agtcccacat                    40

SEQ ID NO: 376       moltype = RNA  length = 40
                        FEATURE              Location/Qualifiers
                        misc_feature         1..40
                                             note = Synthetic
                        source               1..40
                                             mol_type = other RNA
                                             organism = synthetic construct
                        SEQUENCE: 376
                        ctccgacccg cggacgaagt caacttccac agtcccgcac                    40

SEQ ID NO: 377       moltype = RNA  length = 40
                        FEATURE              Location/Qualifiers
                        misc_feature         1..40
                                             note = Synthetic
                        source               1..40
                                             mol_type = other RNA
                                             organism = synthetic construct
                        SEQUENCE: 377
                        ctccgacccg cggacgaagt caacttccac ggtcccacac                    40

SEQ ID NO: 378       moltype = RNA  length = 40
                        FEATURE              Location/Qualifiers
                        misc_feature         1..40
                                             note = Synthetic
                        source               1..40
                                             mol_type = other RNA
                                             organism = synthetic construct
                        SEQUENCE: 378
                        ctccgacccg cggacgaagt caacttccac agtcccatac                    40

SEQ ID NO: 379       moltype = RNA  length = 40
                        FEATURE              Location/Qualifiers
                        misc_feature         1..40
                                             note = Synthetic
                        source               1..40
                                             mol_type = other RNA
                                             organism = synthetic construct
                        SEQUENCE: 379
                        acattaggat ctgcgtgatg gggatcaccc gctacatgtc                    40

SEQ ID NO: 380       moltype = RNA  length = 41
                        FEATURE              Location/Qualifiers
                        misc_feature         1..41
                                             note = Synthetic
                        source               1..41
                                             mol_type = other RNA
                                             organism = synthetic construct
                        SEQUENCE: 380
                        acatttagga tctgcgtgat ggggatcacc cgctacatgt c                  41

SEQ ID NO: 381       moltype = RNA  length = 40
                        FEATURE              Location/Qualifiers
                        misc_feature         1..40
                                             note = Synthetic
                        source               1..40
                                             mol_type = other RNA
                                             organism = synthetic construct
                        SEQUENCE: 381
                        gcattaggat ctgcgtgatg gggatcaccc gctacatgtc                    40

SEQ ID NO: 382       moltype = RNA  length = 40
                        FEATURE              Location/Qualifiers
                        misc_feature         1..40
                                             note = Synthetic
                        source               1..40
                                             mol_type = other RNA
                                             organism = synthetic construct
                        SEQUENCE: 382
                        acattaggat ctgcgcgatg gggatcaccc gctacatgtc                    40

SEQ ID NO: 383       moltype = RNA  length = 40
```

```
FEATURE                 Location/Qualifiers
misc_feature            1..40
                        note = Synthetic
source                  1..40
                        mol_type = other RNA
                        organism = synthetic construct
SEQUENCE: 383
tctaagatgg ggaagatctc cggagcaccg ggcaatcacc                           40

SEQ ID NO: 384          moltype = RNA  length = 41
FEATURE                 Location/Qualifiers
misc_feature            1..41
                        note = Synthetic
source                  1..41
                        mol_type = other RNA
                        organism = synthetic construct
SEQUENCE: 384
tctaagatgg ggaagatctc cggagcaccg ggcaatcacc c                         41

SEQ ID NO: 385          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 385
cctaagatgg ggaagatctc cggagcaccg ggcaatcacc                           40

SEQ ID NO: 386          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 386
tctaaggtgg ggaagatctc cggagcaccg ggcaatcacc                           40

SEQ ID NO: 387          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 387
tctaagatgg ggaagatctc cggagcgccg ggcaatcacc                           40

SEQ ID NO: 388          moltype = RNA  length = 38
FEATURE                 Location/Qualifiers
misc_feature            1..38
                        note = Synthetic
source                  1..38
                        mol_type = other RNA
                        organism = synthetic construct
SEQUENCE: 388
ctattcgagt tcccacgaat cccccatcga gaacctac                             38

SEQ ID NO: 389          moltype = RNA  length = 38
FEATURE                 Location/Qualifiers
misc_feature            1..38
                        note = Synthetic
source                  1..38
                        mol_type = other RNA
                        organism = synthetic construct
SEQUENCE: 389
ctattcgagt tcccacgaat cccccatca gaacctac                              38

SEQ ID NO: 390          moltype = RNA  length = 38
FEATURE                 Location/Qualifiers
misc_feature            1..38
                        note = Synthetic
source                  1..38
                        mol_type = other RNA
                        organism = synthetic construct
SEQUENCE: 390
ctactcgagt tcccacgaat cccccatcga gaacctac                             38
```

-continued

```
SEQ ID NO: 391              moltype = RNA   length = 38
FEATURE                     Location/Qualifiers
misc_feature                1..38
                            note = Synthetic
source                      1..38
                            mol_type = other RNA
                            organism = synthetic construct
SEQUENCE: 391
ctattcgagt tcccacgaat ccccatcaa gaacctac                                    38

SEQ ID NO: 392              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 392
tgccaagccg aggcccggcc agcatccctc acgagagagg                                 40

SEQ ID NO: 393              moltype = RNA   length = 41
FEATURE                     Location/Qualifiers
misc_feature                1..41
                            note = Synthetic
source                      1..41
                            mol_type = other RNA
                            organism = synthetic construct
SEQUENCE: 393
tgccaaagcc gaggcccggc cagcatccct cacgagagag g                               41

SEQ ID NO: 394              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 394
tgccaagccg aggcccggcc agcatccctc acgagagagc                                 40

SEQ ID NO: 395              moltype = RNA   length = 39
FEATURE                     Location/Qualifiers
misc_feature                1..39
                            note = Synthetic
source                      1..39
                            mol_type = other RNA
                            organism = synthetic construct
SEQUENCE: 395
tgccaagccg aggcccggcc agcatccctc acgagagag                                  39

SEQ ID NO: 396              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 396
tgccaagccg aggcccggcc agcatccccc acgagagagg                                 40

SEQ ID NO: 397              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 397
tgccaagccg aggcccggcc agcatccctc acgagagaga                                 40

SEQ ID NO: 398              moltype = RNA   length = 40
FEATURE                     Location/Qualifiers
misc_feature                1..40
                            note = Synthetic
source                      1..40
                            mol_type = other RNA
                            organism = synthetic construct
SEQUENCE: 398
tgccaagccg gggcccggcc agcatccctc acgagagagg                                 40
```

```
SEQ ID NO: 399         moltype = RNA   length = 39
FEATURE                Location/Qualifiers
misc_feature           1..39
                       note = Synthetic
source                 1..39
                       mol_type = other RNA
                       organism = synthetic construct
SEQUENCE: 399
tgccaagccg aggcccggcc agcatccctc acgagaggg                                39

SEQ ID NO: 400         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 400
gccaagcacg tagcccgtgc ccccacccgc ctgtgtgctg                               40

SEQ ID NO: 401         moltype = RNA   length = 39
FEATURE                Location/Qualifiers
misc_feature           1..39
                       note = Synthetic
source                 1..39
                       mol_type = other RNA
                       organism = synthetic construct
SEQUENCE: 401
ccaagcacgt agcccgtgcc cccacccgcc tgtgtgctg                                39

SEQ ID NO: 402         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 402
gccaagcacg tagcccgtgc ccccacccgc ctgtgtgcgg                               40

SEQ ID NO: 403         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 403
gccaagcacg tagcccgtgc ccccacccac ctgtgtgctg                               40

SEQ ID NO: 404         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 404
gccaagcacg tagcccgtgc ccccacccgc ctgtgtgctc                               40

SEQ ID NO: 405         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 405
gccaagcacg tagcccgtgc ccccacccgc ctgtgtgccg                               40

SEQ ID NO: 406         moltype = RNA   length = 41
FEATURE                Location/Qualifiers
misc_feature           1..41
                       note = Synthetic
source                 1..41
                       mol_type = other RNA
                       organism = synthetic construct
SEQUENCE: 406
```

```
                                     -continued gccaaagcac gtagcccgtg cccccacccg cctgtgtgct g                          41

SEQ ID NO: 407          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 407
gccaagcacg tagcccgtgc ccccacccgc ctgtgtgcta                            40

SEQ ID NO: 408          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 408
tgccaagcac gaagcccgtg cccccatcca gagtgtgaga                            40

SEQ ID NO: 409          moltype = RNA    length = 41
FEATURE                 Location/Qualifiers
misc_feature            1..41
                        note = Synthetic
source                  1..41
                        mol_type = other RNA
                        organism = synthetic construct
SEQUENCE: 409
tgccaaagca cgaagcccgt gcccccatcc agagtgtgag a                          41

SEQ ID NO: 410          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 410
tgccaagcac gaagcccgtg cccccatcca gagtgtggga                            40

SEQ ID NO: 411          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 411
tgccaagcac gaggcccgtg cccccatcca gagtgtgaga                            40

SEQ ID NO: 412          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 412
tgccaagcac gaagcccgtg cccccattca gagtgtgaga                            40

SEQ ID NO: 413          moltype = RNA    length = 40
FEATURE                 Location/Qualifiers
misc_feature            1..40
                        note = Synthetic
source                  1..40
                        mol_type = other RNA
                        organism = synthetic construct
SEQUENCE: 413
tgccaagcac gaagcccgtg cccccatcca gagtgcgaga                            40

SEQ ID NO: 414          moltype = RNA    length = 40
FEATURE                 Location/Qualifiers
misc_feature            1..40
                        note = Synthetic
source                  1..40
                        mol_type = other RNA
                        organism = synthetic construct
```

```
SEQUENCE: 414
tgccaagcac gaagcccgtg cccccatcca gagcgtgaga                              40

SEQ ID NO: 415           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 415
tgccaagcac gaagcccgtg cccccatcca gagtgtgagg                              40

SEQ ID NO: 416           moltype = RNA   length = 40
FEATURE                  Location/Qualifiers
misc_feature             1..40
                         note = Synthetic
source                   1..40
                         mol_type = other RNA
                         organism = synthetic construct
SEQUENCE: 416
tgccaagcac gaagcccgtg cccccatcca gggtgtgaga                              40

SEQ ID NO: 417           moltype = RNA   length = 42
FEATURE                  Location/Qualifiers
misc_feature             1..42
                         note = Synthetic
source                   1..42
                         mol_type = other RNA
                         organism = synthetic construct
SEQUENCE: 417
agccagcttt tgcataccac gtgcaattca ctccacccgt ca                           42

SEQ ID NO: 418           moltype = RNA   length = 42
FEATURE                  Location/Qualifiers
misc_feature             1..42
                         note = Synthetic
source                   1..42
                         mol_type = other RNA
                         organism = synthetic construct
SEQUENCE: 418
agccagcttt gccataccac gtgcaattca ctccacccgt ca                           42

SEQ ID NO: 419           moltype = RNA   length = 42
FEATURE                  Location/Qualifiers
misc_feature             1..42
                         note = Synthetic
source                   1..42
                         mol_type = other RNA
                         organism = synthetic construct
SEQUENCE: 419
agccagcctt tgcataccac gtgcaattca ctccacccgt ca                           42

SEQ ID NO: 420           moltype = RNA   length = 42
FEATURE                  Location/Qualifiers
misc_feature             1..42
                         note = Synthetic
source                   1..42
                         mol_type = other RNA
                         organism = synthetic construct
SEQUENCE: 420
agccagcttt tgcataccac gtgcaattca ctccacccgt cg                           42

SEQ ID NO: 421           moltype = RNA   length = 42
FEATURE                  Location/Qualifiers
misc_feature             1..42
                         note = Synthetic
source                   1..42
                         mol_type = other RNA
                         organism = synthetic construct
SEQUENCE: 421
agccagcttt tgcacaccac gtgcaattca ctccacccgt ca                           42

SEQ ID NO: 422           moltype = RNA   length = 42
FEATURE                  Location/Qualifiers
misc_feature             1..42
                         note = Synthetic
source                   1..42
                         mol_type = other RNA
```

```
                          organism = synthetic construct
SEQUENCE: 422
agccaagctt tgcataccac gtgcaattca ctccacccgt ca                              42

SEQ ID NO: 423            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 423
ctttgtaaac ccggcaaaca aaatcaactt ccatcatcaa                                 40

SEQ ID NO: 424            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 424
ctttgtaaac ccggcaaaca aaatcaactt ccatcaccaa                                 40

SEQ ID NO: 425            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 425
ccattgtagc gaccacacaa ttccccatcg gacagcatgg                                 40

SEQ ID NO: 426            moltype = RNA   length = 39
FEATURE                   Location/Qualifiers
misc_feature              1..39
                          note = Synthetic
source                    1..39
                          mol_type = other RNA
                          organism = synthetic construct
SEQUENCE: 426
ccattgtagc gaccacacaa ttccccatcg gacagcatg                                  39

SEQ ID NO: 427            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 427
ccattgtagc gaccacacaa ttccccatcg gacagcgtgg                                 40

SEQ ID NO: 428            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 428
ccattgtagc gaccacacaa ttccccatcg gacagcacgg                                 40

SEQ ID NO: 429            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 429
ccattgtagc gaccacacaa ttccccatcg gacagcatgc                                 40

SEQ ID NO: 430            moltype = RNA   length = 40
FEATURE                   Location/Qualifiers
misc_feature              1..40
                          note = Synthetic
source                    1..40
```

```
                        mol_type = other RNA
                        organism = synthetic construct
SEQUENCE: 430
ccattgtagc gaccacacaa tcccccatcg gacagcatgg                              40

SEQ ID NO: 431          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 431
ccattgtagc gaccacacaa ttcccatcg gacagcatgt                               40

SEQ ID NO: 432          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 432
ctctcgccgt tcccaggcac gacaaaatca acttcccgct                              40

SEQ ID NO: 433          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 433
ctctcgccgt tcccaggcgc gacaaaatca acttcccgct                              40

SEQ ID NO: 434          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 434
ctctcgccgt tcccgggcac gacaaaatca acttcccgct                              40

SEQ ID NO: 435          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 435
ctctcgccgt tcccaggcac gacaaaatca acttcccgca                              40

SEQ ID NO: 436          moltype = RNA   length = 40
FEATURE                 Location/Qualifiers
misc_feature            1..40
                        note = Synthetic
source                  1..40
                        mol_type = other RNA
                        organism = synthetic construct
SEQUENCE: 436
aagccaagcc gcggcccggc cttcccatgt gctactagag                              40

SEQ ID NO: 437          moltype = RNA   length = 41
FEATURE                 Location/Qualifiers
misc_feature            1..41
                        note = Synthetic
source                  1..41
                        mol_type = other RNA
                        organism = synthetic construct
SEQUENCE: 437
aaagccaagc cgcggcccgg ccttcccatg tgctactaga g                            41

SEQ ID NO: 438          moltype = RNA   length = 41
FEATURE                 Location/Qualifiers
misc_feature            1..41
                        note = Synthetic
```

```
                              -continued source              1..41
                    mol_type = other RNA
                    organism = synthetic construct
SEQUENCE: 438
aagccaaagc cgcggcccgg ccttcccatg tgctactaga g                41

SEQ ID NO: 439         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 439
gagccaagcc gcggcccggc cttcccatgt gctactagag                  40

SEQ ID NO: 440         moltype = RNA   length = 39
FEATURE                Location/Qualifiers
misc_feature           1..39
                       note = Synthetic
source                 1..39
                       mol_type = other RNA
                       organism = synthetic construct
SEQUENCE: 440
agccaagccg cggcccggcc ttcccatgtg ctactagag                   39

SEQ ID NO: 441         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 441
aagccaagcc gtggcccggc cttcccatgt gctactagag                  40

SEQ ID NO: 442         moltype = RNA   length = 39
FEATURE                Location/Qualifiers
misc_feature           1..39
                       note = Synthetic
source                 1..39
                       mol_type = other RNA
                       organism = synthetic construct
SEQUENCE: 442
tgccaagccg cggcccggcc ttcccatgtg ctactagag                   39

SEQ ID NO: 443         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 443
aagccaagcc gaggcccggc cttcccatgt gctactagag                  40

SEQ ID NO: 444         moltype = RNA   length = 41
FEATURE                Location/Qualifiers
misc_feature           1..41
                       note = Synthetic
source                 1..41
                       mol_type = other RNA
                       organism = synthetic construct
SEQUENCE: 444
ccaaatgcca agccgtagc ccggccagta gcccacacgt c                 41

SEQ ID NO: 445         moltype = RNA   length = 42
FEATURE                Location/Qualifiers
misc_feature           1..42
                       note = Synthetic
source                 1..42
                       mol_type = other RNA
                       organism = synthetic construct
SEQUENCE: 445
ccaaaatgcc aagccgtag cccggccagt agcccacacg tc                42

SEQ ID NO: 446         moltype = RNA   length = 41
FEATURE                Location/Qualifiers
misc_feature           1..41
```

```
                       note = Synthetic
source                 1..41
                       mol_type = other RNA
                       organism = synthetic construct
SEQUENCE: 446
ccaaatgcca agcccgtagc ccggccagta gcccacacgt c                   41

SEQ ID NO: 447         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 447
ccattacgcg acgtaattcc cccatcgttt cctcgttaag                     40

SEQ ID NO: 448         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 448
ccattacgcg acgtaattcc cccatcgtct cctcgttaag                     40

SEQ ID NO: 449         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 449
ccattacgcg acgtaattcc cccatcgctt cctcgttaag                     40

SEQ ID NO: 450         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 450
ccattacgcg gcgtaattcc cccatcgttt cctcgttaag                     40

SEQ ID NO: 451         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 451
ccattacgcg acgtaattcc cccatcgttt cctcgttagg                     40

SEQ ID NO: 452         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 452
ccattacgcg acgtaattcc cccatcgttt cctcgctaag                     40

SEQ ID NO: 453         moltype = RNA   length = 40
FEATURE                Location/Qualifiers
misc_feature           1..40
                       note = Synthetic
source                 1..40
                       mol_type = other RNA
                       organism = synthetic construct
SEQUENCE: 453
ccattacgcg acgtaattcc cccatcgttt cctcgttatg                     40

SEQ ID NO: 454         moltype = RNA   length = 40
FEATURE                Location/Qualifiers
```

```
misc_feature               1..40
                           note = Synthetic
source                     1..40
                           mol_type = other RNA
                           organism = synthetic construct
SEQUENCE: 454
ccattacgcg acgtaattcc cccatcgttt cctcgttaaa                              40

SEQ ID NO: 455             moltype = RNA   length = 38
FEATURE                    Location/Qualifiers
misc_feature               1..38
                           note = Synthetic
source                     1..38
                           mol_type = other RNA
                           organism = synthetic construct
SEQUENCE: 455
ccatctagat ctccgtagat tccccggctc tttctcgc                                38

SEQ ID NO: 456             moltype = RNA   length = 38
FEATURE                    Location/Qualifiers
misc_feature               1..38
                           note = Synthetic
source                     1..38
                           mol_type = other RNA
                           organism = synthetic construct
SEQUENCE: 456
ccatctagat ctccgtagat tccccagctc tttctcgc                                38

SEQ ID NO: 457             moltype = RNA   length = 38
FEATURE                    Location/Qualifiers
misc_feature               1..38
                           note = Synthetic
source                     1..38
                           mol_type = other RNA
                           organism = synthetic construct
SEQUENCE: 457
ccatctagat ctccgtagat cccccggctc tttctcgc                                38

SEQ ID NO: 458             moltype = RNA   length = 38
FEATURE                    Location/Qualifiers
misc_feature               1..38
                           note = Synthetic
source                     1..38
                           mol_type = other RNA
                           organism = synthetic construct
SEQUENCE: 458
ccatctagat ctccgtagat tcccccgctc tttctcgc                                38

SEQ ID NO: 459             moltype = RNA   length = 38
FEATURE                    Location/Qualifiers
misc_feature               1..38
                           note = Synthetic
source                     1..38
                           mol_type = other RNA
                           organism = synthetic construct
SEQUENCE: 459
ccatctagat ctccgtagat tccccggctc ttcctcgc                                38

SEQ ID NO: 460             moltype = RNA   length = 38
FEATURE                    Location/Qualifiers
misc_feature               1..38
                           note = Synthetic
source                     1..38
                           mol_type = other RNA
                           organism = synthetic construct
SEQUENCE: 460
ccatctagat ctccgtgatt cccccggctc tttctcgc                                38

SEQ ID NO: 461             moltype = RNA   length = 38
FEATURE                    Location/Qualifiers
misc_feature               1..38
                           note = Synthetic
source                     1..38
                           mol_type = other RNA
                           organism = synthetic construct
SEQUENCE: 461
ccatctagat ctccgtagtt cccccggctc tttctcgc                                38

SEQ ID NO: 462             moltype = RNA   length = 38
```

```
FEATURE                 Location/Qualifiers
misc_feature            1..38
                        note = Synthetic
source                  1..38
                        mol_type = other RNA
                        organism = synthetic construct
SEQUENCE: 462
ccatctagat ccccgtagat tccccggctc tttctcgc                              38

SEQ ID NO: 463          moltype = RNA  length = 38
FEATURE                 Location/Qualifiers
misc_feature            1..38
                        note = Synthetic
source                  1..38
                        mol_type = other RNA
                        organism = synthetic construct
SEQUENCE: 463
ccatctagat ctccgtagat tccccggctc cttctcgc                              38

SEQ ID NO: 464          moltype = RNA  length = 38
FEATURE                 Location/Qualifiers
misc_feature            1..38
                        note = Synthetic
source                  1..38
                        mol_type = other RNA
                        organism = synthetic construct
SEQUENCE: 464
ccatctatat ctccgtagat tccccggctc tttctcgc                              38

SEQ ID NO: 465          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 465
actgtctgca tacacggtat gcccaacgcc atccaaaccg                            40

SEQ ID NO: 466          moltype = RNA  length = 41
FEATURE                 Location/Qualifiers
misc_feature            1..41
                        note = Synthetic
source                  1..41
                        mol_type = other RNA
                        organism = synthetic construct
SEQUENCE: 466
actgtctgca tacacggtat gcccaacgcc atccaaaccg c                          41

SEQ ID NO: 467          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 467
actgtctgca tacatggtat gcccaacgcc atccaaaccg                            40

SEQ ID NO: 468          moltype = RNA  length = 41
FEATURE                 Location/Qualifiers
misc_feature            1..41
                        note = Synthetic
source                  1..41
                        mol_type = other RNA
                        organism = synthetic construct
SEQUENCE: 468
actgtctgca tacacggtat gcccaacgcc atccaaaacc g                          41

SEQ ID NO: 469          moltype = RNA  length = 40
FEATURE                 Location/Qualifiers
misc_feature            1..40
                        note = Synthetic
source                  1..40
                        mol_type = other RNA
                        organism = synthetic construct
SEQUENCE: 469
acctgcggct attgccagcg ccataagacc ctccacagta                            40
```

```
SEQ ID NO: 470            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 470
acctgcggct attgccagcg ccataagacc ctccacagca                              40

SEQ ID NO: 471            moltype = RNA   length = 39
FEATURE                   Location/Qualifiers
misc_feature              1..39
                          note = Synthetic
source                    1..39
                          mol_type = other RNA
                          organism = synthetic construct
SEQUENCE: 471
cctgcggcta ttgccagcgc cataagaccc tccacagta                               39

SEQ ID NO: 472            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 472
acctgcggct attgccagcg ccataagacc ttccacagta                              40

SEQ ID NO: 473            moltype = RNA   length = 40
FEATURE                   Location/Qualifiers
misc_feature              1..40
                          note = Synthetic
source                    1..40
                          mol_type = other RNA
                          organism = synthetic construct
SEQUENCE: 473
acctgcggct attgccagcg ccataagacc ctccgcagta                              40

SEQ ID NO: 474            moltype = RNA   length = 56
FEATURE                   Location/Qualifiers
misc_feature              1..56
                          note = Synthetic
source                    1..56
                          mol_type = other RNA
                          organism = synthetic construct
SEQUENCE: 474
ggaagaggga tgggtgccag ctttgcatac cacgtgcaat tcactccacc cgtcac           56

SEQ ID NO: 475            moltype = RNA   length = 64
FEATURE                   Location/Qualifiers
misc_feature              1..64
                          note = Synthetic
source                    1..64
                          mol_type = other RNA
                          organism = synthetic construct
SEQUENCE: 475
gggagagagg aagagggatg ggagccagct ttgcatacca cgtgcaattc actccacccg       60
tcac                                                                    64

SEQ ID NO: 476            moltype = RNA   length = 56
FEATURE                   Location/Qualifiers
misc_feature              1..56
                          note = Synthetic
source                    1..56
                          mol_type = other RNA
                          organism = synthetic construct
SEQUENCE: 476
gggatgggca catggtacgc ccaaagcgag gcccgctgcg tagtgccata acccag           56

SEQ ID NO: 477            moltype = RNA   length = 61
FEATURE                   Location/Qualifiers
misc_feature              1..61
                          note = Synthetic
source                    1..61
                          mol_type = other RNA
                          organism = synthetic construct
SEQUENCE: 477
```

```
gggagagagg aagagggatg ggcacatggt acgcccaaag cgaggcccgc tgcgtagtgc    60
c                                                                   61

SEQ ID NO: 478         moltype = RNA   length = 66
FEATURE                Location/Qualifiers
misc_feature           1..66
                       note = Synthetic
source                 1..66
                       mol_type = other RNA
                       organism = synthetic construct
SEQUENCE: 478
gggatgggca cggtccagcg ctaactgtac ctgctgtgcc acccaccgca taacccagag    60
gtcgat                                                              66

SEQ ID NO: 479         moltype = RNA   length = 49
FEATURE                Location/Qualifiers
misc_feature           1..49
                       note = Synthetic
source                 1..49
                       mol_type = other RNA
                       organism = synthetic construct
SEQUENCE: 479
gggatgggca cggtccagcg ctaactgtac ctgctgtgcc acccaccgc                49

SEQ ID NO: 480         moltype = RNA   length = 62
FEATURE                Location/Qualifiers
misc_feature           1..62
                       note = Synthetic
source                 1..62
                       mol_type = other RNA
                       organism = synthetic construct
SEQUENCE: 480
gggagagagg aagagggatg ggcacggtcc agcgctaact gtacctgctg tgccacccac    60
cg                                                                  62

SEQ ID NO: 481         moltype = RNA   length = 45
FEATURE                Location/Qualifiers
misc_feature           1..45
                       note = Synthetic
source                 1..45
                       mol_type = other RNA
                       organism = synthetic construct
SEQUENCE: 481
gggagagagg aagagggatg ggcacggtcc agcgctaact gtacc                   45

SEQ ID NO: 482         moltype = RNA   length = 53
FEATURE                Location/Qualifiers
misc_feature           1..53
                       note = Synthetic
source                 1..53
                       mol_type = other RNA
                       organism = synthetic construct
SEQUENCE: 482
ggaagaggga tgggcacggt ccagcgctaa ctgtacctgc tgtgccaccc acc           53

SEQ ID NO: 483         moltype = RNA   length = 43
FEATURE                Location/Qualifiers
misc_feature           1..43
                       note = Synthetic
source                 1..43
                       mol_type = other RNA
                       organism = synthetic construct
SEQUENCE: 483
gggaccacgc gccaacgtgt cagctacacg ccgtgttccc cgg                     43

SEQ ID NO: 484         moltype = RNA   length = 61
FEATURE                Location/Qualifiers
misc_feature           1..61
                       note = Synthetic
source                 1..61
                       mol_type = other RNA
                       organism = synthetic construct
SEQUENCE: 484
gggaccacgc gccaacgtgt cagctacacg ccgtgttccc cggcataacc cagaggtcga    60
t                                                                   61

SEQ ID NO: 485         moltype = RNA   length = 62
FEATURE                Location/Qualifiers
misc_feature           1..62
```

```
                        note = Synthetic
source                  1..62
                        mol_type = other RNA
                        organism = synthetic construct
SEQUENCE: 485
gggagagagg aagagggatg ggaccacgcg ccaacgtgtc agctacacgc cgtgttcccc   60
gg                                                                 62

SEQ ID NO: 486          moltype = RNA   length = 44
FEATURE                 Location/Qualifiers
misc_feature            1..44
                        note = Synthetic
source                  1..44
                        mol_type = other RNA
                        organism = synthetic construct
SEQUENCE: 486
gggatgggca cggtccagcg ctaactgtac ctgctgtgcc accc                    44

SEQ ID NO: 487          moltype = RNA   length = 54
FEATURE                 Location/Qualifiers
misc_feature            1..54
                        note = Synthetic
source                  1..54
                        mol_type = other RNA
                        organism = synthetic construct
SEQUENCE: 487
gggaggaaga gggatgggca cggtccagcg ctaactgtac ctgctgtgcc accc          54

SEQ ID NO: 488          moltype = RNA   length = 52
FEATURE                 Location/Qualifiers
misc_feature            1..52
                        note = Synthetic
source                  1..52
                        mol_type = other RNA
                        organism = synthetic construct
SEQUENCE: 488
gggaggaaga ggatgggcac ggtccagcgc taactgtacc tgctgtgcca cc            52

SEQ ID NO: 489          moltype = RNA   length = 52
FEATURE                 Location/Qualifiers
misc_feature            1..52
                        note = Synthetic
source                  1..52
                        mol_type = other RNA
                        organism = synthetic construct
SEQUENCE: 489
gggaggaaga gggatgggca cggtccagcg cactgtacct gctgtgccac cc            52

SEQ ID NO: 490          moltype = RNA   length = 50
FEATURE                 Location/Qualifiers
misc_feature            1..50
                        note = Synthetic
source                  1..50
                        mol_type = other RNA
                        organism = synthetic construct
SEQUENCE: 490
gggaggaaga ggatgggcac ggtccagcgc actgtacctg ctgtgccacc               50

SEQ ID NO: 491          moltype = RNA   length = 22
FEATURE                 Location/Qualifiers
misc_feature            1..22
                        note = Synthetic
source                  1..22
                        mol_type = other RNA
                        organism = synthetic construct
SEQUENCE: 491
gggagagagg aagagggatg gg                                             22

SEQ ID NO: 492          moltype = RNA   length = 34
FEATURE                 Location/Qualifiers
misc_feature            1..34
                        note = Synthetic
source                  1..34
                        mol_type = other RNA
                        organism = synthetic construct
SEQUENCE: 492
cataacccag aggtcgatag tactggatcc cccc                                34

SEQ ID NO: 493          moltype = AA   length = 710
```

```
FEATURE                 Location/Qualifiers
REGION                  1..710
                        note = misc_feature - amino acid sequence for nucleolin
source                  1..710
                        mol_type = protein
                        organism = Homo sapiens
SEQUENCE: 493
MVKLAKAGKN QGDPKKMAPP PKEVEEDSED EEMSEDEEDD SSGEEVVIPQ KKGKKAAATS    60
AKKVVVSPTK KVAVATPAKK AAVTPGKKAA ATPAKKTVTP AKAVTTPGKK GATPGKALVA   120
TPGKKGAAIP AKGAKNGKNA KKEDSDEEED DDSEEDEEDD EDEDEDEDEI EPAAMKAAAA   180
APASEDEDDE DDEDDEDDDD DEEDSEEEA METTPAKGKK AAKVVPVKAK NVAEDEDEEE    240
DDEDEDDDDD EDDEDDDDED DEEEEEEEEE EPVKEAPGKR KKEMAKQKAA PEAKKQKVEG   300
TEPTTAFNLF VGNLNFNKSA PELKTGISDV FAKNDLAVVD VRIGMTRKFG YVDFESAEDL   360
EKALELTGLK VFGNEIKLEK PKGKDSKKER DARTLLAKNL PYKVTQDELK EVFEDAAEIR   420
LVSKDGKSKG IAYIEFKTEA DAEKTFEEKQ GTEIDGRSIS LYYTGEKGQN QDYRGGKNST   480
WSGESKTLVL SNLSYSATEE TLQEVFEKAT FIKVPQNQNG KSKGYAFIEF ASFEDAKEAL   540
NSCNKREIEG RAIRLELQGP RGSPNARSQP SKTLFVKGLS EDTTEETLKE SFDGSVRARI   600
VTDRETGSSK GFGFVDFNSE EDAKAAKEAM EDGEIDGNKV TLDWAKPKGE GGFGGRGGGR   660
GGFGGRGGGR GGRGGFGGRG RGGFGGRGGF RGGRGGGGDH KPQGKKTKFE              710

SEQ ID NO: 494          moltype = RNA   length = 49
FEATURE                 Location/Qualifiers
misc_feature            1..49
                        note = Synthetic
source                  1..49
                        mol_type = other RNA
                        organism = synthetic construct
SEQUENCE: 494
gggatgggaa gatctgctaa gtgcacgcac aatcaccatc gagcgtctc                49

SEQ ID NO: 495          moltype = RNA   length = 63
FEATURE                 Location/Qualifiers
misc_feature            1..63
                        note = Synthetic
source                  1..63
                        mol_type = other RNA
                        organism = synthetic construct
SEQUENCE: 495
gggagagagg aagagggatg ggaagatctg ctaagtgcac gcacaatcac catcgagcgt    60
ctc                                                                  63

SEQ ID NO: 496          moltype = RNA   length = 54
FEATURE                 Location/Qualifiers
misc_feature            1..54
                        note = Synthetic
source                  1..54
                        mol_type = other RNA
                        organism = synthetic construct
SEQUENCE: 496
gggagagagg aagagggatg ggcacggtcc agcgctaact gtacctgctg tgcc          54

SEQ ID NO: 497          moltype = RNA   length = 58
FEATURE                 Location/Qualifiers
misc_feature            1..58
                        note = Synthetic
source                  1..58
                        mol_type = other RNA
                        organism = synthetic construct
SEQUENCE: 497
gggagagaga gggatgggca cggtccagcg ctaactgtac ctgctgtgcc acccaccg      58

SEQ ID NO: 498          moltype = RNA   length = 60
FEATURE                 Location/Qualifiers
misc_feature            1..60
                        note = Synthetic
source                  1..60
                        mol_type = other RNA
                        organism = synthetic construct
SEQUENCE: 498
gggagagagg aagaggatgg gcacggtcca gcgctaactg tacctgctgt gccaccaccg    60

SEQ ID NO: 499          moltype = RNA   length = 60
FEATURE                 Location/Qualifiers
misc_feature            1..60
                        note = Synthetic
source                  1..60
                        mol_type = other RNA
                        organism = synthetic construct
SEQUENCE: 499
```

```
gggagagagg aagagggagg gcacggtcca gcgctaactg tacctgctgt gcccccaccg    60

SEQ ID NO: 500         moltype = RNA  length = 52
FEATURE                Location/Qualifiers
misc_feature           1..52
                       note = Synthetic
source                 1..52
                       mol_type = other RNA
                       organism = synthetic construct
SEQUENCE: 500
gggagagagg aagagggatg ggtccagcgc taactgtacc tgccacccac cg            52

SEQ ID NO: 501         moltype = RNA  length = 58
FEATURE                Location/Qualifiers
misc_feature           1..58
                       note = Synthetic
source                 1..58
                       mol_type = other RNA
                       organism = synthetic construct
SEQUENCE: 501
gggagagagg aagagggatg ggcggtccag cgctaactgt acctgctgcc acccaccg      58

SEQ ID NO: 502         moltype = RNA  length = 58
FEATURE                Location/Qualifiers
misc_feature           1..58
                       note = Synthetic
source                 1..58
                       mol_type = other RNA
                       organism = synthetic construct
SEQUENCE: 502
gggagagagg aagagggatg ggcacggtcc agcgctatgt ctgctgtgcc acccaccg      58

SEQ ID NO: 503         moltype = RNA  length = 58
FEATURE                Location/Qualifiers
misc_feature           1..58
                       note = Synthetic
source                 1..58
                       mol_type = other RNA
                       organism = synthetic construct
SEQUENCE: 503
gggagagagg aagagggatg ggcacggtcc agcgctaact gtacctgctg tgccaccc      58

SEQ ID NO: 504         moltype = RNA  length = 58
FEATURE                Location/Qualifiers
misc_feature           1..58
                       note = Synthetic
source                 1..58
                       mol_type = other RNA
                       organism = synthetic construct
SEQUENCE: 504
gggaggaaga gggatgggca cggtccagcg ctaactgtac tgctgtgcc acccaccg       58

SEQ ID NO: 505         moltype = RNA  length = 54
FEATURE                Location/Qualifiers
misc_feature           1..54
                       note = Synthetic
source                 1..54
                       mol_type = other RNA
                       organism = synthetic construct
SEQUENCE: 505
ggaagaggga tgggcacggt ccagcgctaa ctgtacctgc tgtgccaccc accg          54

SEQ ID NO: 506         moltype = RNA  length = 58
FEATURE                Location/Qualifiers
misc_feature           1..58
                       note = Synthetic
source                 1..58
                       mol_type = other RNA
                       organism = synthetic construct
SEQUENCE: 506
gagaggaaga gggatgggca cggtccagcg ctaactgtac ctgctgtgcc acccaccg      58

SEQ ID NO: 507         moltype = RNA  length = 60
FEATURE                Location/Qualifiers
misc_feature           1..60
                       note = Synthetic
source                 1..60
                       mol_type = other RNA
                       organism = synthetic construct
```

```
SEQUENCE: 507
gggagagagg aagagggatg ggcacggtcc agcgctaact gtacctgctg tgccacccac   60

SEQ ID NO: 508           moltype = RNA   length = 60
FEATURE                  Location/Qualifiers
misc_feature             1..60
                         note = Synthetic
source                   1..60
                         mol_type = other RNA
                         organism = synthetic construct
SEQUENCE: 508
gggagagagg aagagggatg ggcacggtcc agcgctaact gtacctgctg tgccaccccg   60

SEQ ID NO: 509           moltype = RNA   length = 60
FEATURE                  Location/Qualifiers
misc_feature             1..60
                         note = Synthetic
source                   1..60
                         mol_type = other RNA
                         organism = synthetic construct
SEQUENCE: 509
gggagagagg aagagggatg ggcacggtcc gcgctaactg tacctgctgg ccacccaccg   60

SEQ ID NO: 510           moltype = RNA   length = 60
FEATURE                  Location/Qualifiers
misc_feature             1..60
                         note = Synthetic
source                   1..60
                         mol_type = other RNA
                         organism = synthetic construct
SEQUENCE: 510
gggagagagg aagagggatg ggcacggtcc gcgctaactg taccgctgtg ccacccaccg   60

SEQ ID NO: 511           moltype = RNA   length = 60
FEATURE                  Location/Qualifiers
misc_feature             1..60
                         note = Synthetic
source                   1..60
                         mol_type = other RNA
                         organism = synthetic construct
SEQUENCE: 511
gggagagagg aagagggatg ggcacggtcc agcgcactgt acctgctgtg ccacccaccg   60

SEQ ID NO: 512           moltype = RNA   length = 62
FEATURE                  Location/Qualifiers
misc_feature             1..62
                         note = Synthetic
source                   1..62
                         mol_type = other RNA
                         organism = synthetic construct
SEQUENCE: 512
gggagagagg aagagggatg ggcacggtcc agcgctaact gtacctgctg tgccacccac   60
cg                                                                  62

SEQ ID NO: 513           moltype = RNA   length = 60
FEATURE                  Location/Qualifiers
misc_feature             1..60
                         note = Synthetic
source                   1..60
                         mol_type = other RNA
                         organism = synthetic construct
SEQUENCE: 513
gggagaggaa gagggatggg cacggtccag cgctaactgt acctgctgtg ccacccaccg   60

SEQ ID NO: 514           moltype = RNA   length = 60
FEATURE                  Location/Qualifiers
misc_feature             1..60
                         note = Synthetic
source                   1..60
                         mol_type = other RNA
                         organism = synthetic construct
```

```
SEQUENCE: 514
gggagaggaa gagggatggg cacggtccag cgctaactgt acctgctgtg ccacccaccg    60

SEQ ID NO: 515         moltype = RNA   length = 56
FEATURE                Location/Qualifiers
misc_feature           1..56
                       note = Synthetic
source                 1..56
                       mol_type = other RNA
                       organism = synthetic construct
SEQUENCE: 515
gaggaagagg gatgggcacg gtccagcgct aactgtacct gctgtgccac ccaccg    56
```

NUCLEOLIN-TARGETING APTAMERS AND METHODS OF USING THE SAME

CROSS-REFERENCE TO RELATED APPLICATIONS

This patent application is a divisional of U.S. patent application Ser. No. 16/645,762, filed Mar. 9, 2020 which application is a national stage filing under 35 U.S.C. 371 of International Application No. PCT/US2018/050240, filed Sep. 10, 2018, which claims the benefit of priority of U.S. Provisional Patent Application No. 62/555,745, filed Sep. 8, 2017, all of which are incorporated herein by reference in their entirety.

STATEMENT REGARDING FEDERALLY SPONSORED RESEARCH

This invention was made with government support by the National Institutes of Health under Award Number CA159826. The government has certain rights in the invention.

SEQUENCE LISTING

This application is being filed electronically via Patent Center and includes an electronically submitted Sequence Listing in .xml format. The .xml file contains a sequence listing entitled "155554.00702.xml" created on Nov. 21, 2023 and is 658,560 bytes in size. The Sequence Listing contained in this .xml file is part of the specification and is hereby incorporated by reference herein in its entirety.

INTRODUCTION

The protein nucleolin plays a critical role in repair of DNA double-stranded breaks (DSB) (Goldstein et al, PNAS, 2013). Mechanistically, nucleolin functions as a histone chaperone at the DSB, escorting the histone proteins H2A and H2B away from the nucleosome at the DNA break. This nucleosome disruption is required for the recruitment of repair enzymes and the repair of the DNA breaks. Therefore, inhibition of nucleolin results in sensitization of cells to DNA damaging agents. Importantly, the majority of human tumors overexpress nucleolin on the cell surface relative to normal cells, thus making nucleolin a tumor-preferential target. A nucleolin inhibitor would have the unique ability to specifically sensitize only tumor cells to DNA damaging agents as it should only target and internalize into cancerous cells.

Aptamers, small artificial RNA or DNA oligonucleotide ligands, can be selected to inhibit protein function and are also emerging as important tumor-targeting molecules. Additionally, they have many advantages over traditional antibody targeting agents, including ease of synthesis and amenability to chemical modification (Keefe et al, Nat Rev Drug Discov, 2010). Moreover, they exhibit antibody-like target affinities and specificities at a fraction of the size, allowing more efficient tumor penetration while maintaining the ability to discriminate between proteins that differ by only a few amino acids (reviewed in Conrad et al, Methods Enzymol, 1996; Obsorne et al, Chem Rev, 1997).

There is a need in the art for new aptamers that may bind to and/or inhibit the nucleolin protein. Such aptamers may be useful not only as new cancer treatments but also may facilitate the delivery of agents to the nucleus of a cell.

SUMMARY

In one aspect of the present invention, aptamers are provided. The aptamer may include a polynucleotide having at least 50%, 60%, 70%, 80%, 85%, 90%, 91%, 92%, 93%, 94%, 95%, 96%, 97%, 98%, 99%, or 100% sequence identity to any one of SEQ ID NOS: 1-490, 494-515, or any one of the sequences described in the Tables or Figures disclosed herein (for example, Tables 1-4, 6-8 or FIG. 11A-11B, 12A-12B, 13A-13C, 14A-14D, 15A-15B, 16, 17, 18, 19, 20, 21, 22, 23, 24, 25, 26, 27, 28A-28B, 29, 30, 31, 32, 33, 34, 35, 36 or 37A-37B). In another aspect, the present invention relates to dimers, trimers, and tetramers including any one of the aptamers described herein.

In a further aspect of the present invention, pharmaceutical compositions including any of the aptamers described herein are provided. The pharmaceutical compositions may include a pharmaceutical carrier, excipient, or diluent.

In a still further aspect, the present invention relates to methods for treating cancer in a subject. The methods may include administering to the subject a therapeutically effective amount of any one of the aptamers, dimers, trimers, tetramers, or pharmaceutical compositions described herein.

In a still further aspect, methods of labeling or inhibiting nucleolin are provided. The methods include contacting nucleolin with any one of the compositions described herein to allow binding and possibly inhibition of the activity of the nucleolin. This contacting can be in vitro by adding the nucleolin to cells or may be in vivo by administering the compositions described herein to a subject. The compositions and aptamers provided herein are capable of binding to and possibly inhibiting the function of nucleolin.

BRIEF DESCRIPTION OF THE DRAWINGS

FIGS. 3A-3B show nucleolin-specific RNA aptamers bind to the RBD domain of nucleolin. (FIG. 3A) Map of truncated nucleolin mutants. From Chen et al. 2011, *JBC*. (FIG. 3B) Southwestern blot showing the binding of the initial RNA aptamer library (Sell) versus SELEX round 6 (R6 NCL) to truncated nucleolin mutants expressed in MCF7 cells.

FIG. 4 shows binding analysis of the nucleolin (NCL) aptamers identified through high throughput sequencing. Aptamers were end-labeled with $^{32}$P. Nucleolin protein was serially diluted in 20 mM Hepes, 150 mM NaCl, 2 mM CaCl$_2$) and 0.01% bovine serum albumin and incubated with a trace amount of the $^{32}$P-labeled RNA pools. After incubation at 37° C., unbound RNA was captured on a nylon membrane and RNA-nucleolin complexes captured on a nitrocellulose membrane. The fraction of protein-bound RNA was determined via phosphorimaging of the nitrocellulose and nylon membranes.

FIGS. 9A-9D show binding of Ev3 aptamer truncates to the nucleolin protein. Aptamers were end-labeled with $^{32}$P. Nucleolin protein was serially diluted in 20 mM Hepes, 150 mM NaCl, 2 mM CaCl$_2$) and 0.01% bovine serum albumin and incubated with a trace amount of the $^{32}$P-labeled RNA pools. After incubation at 37° C., unbound RNA was captured on a nylon membrane and RNA-nucleolin complexes captured on a nitrocellulose membrane. The fraction of protein-bound RNA was determined via phosphorimaging of the nitrocellulose and nylon membranes.

FIGS. 11A-11B show predicted secondary structures for a representative Family B aptamer (SEQ ID NO: 8).

FIGS. 13A-13C show predicted secondary structures for a representative Family D aptamer (SEQ ID NO: 10).

FIGS. 14A-14D show predicted secondary structures for a representative Family E aptamer (SEQ ID NO: 11).

FIGS. 15A-15B show predicted secondary structures for a representative Family F aptamer (SEQ ID NO: 12).

FIG. 16 shows predicted secondary structures for Ev3min2 truncate aptamer (SEQ ID NO: 497).

FIG. 25 shows predicted secondary structures for Ev3min11 truncate aptamer (SEQ ID NO: 506).

FIG. 27 shows predicted secondary structures for Ev3min13 truncate aptamer (SEQ ID NO: 508).

DETAILED DESCRIPTION

Figure 1:
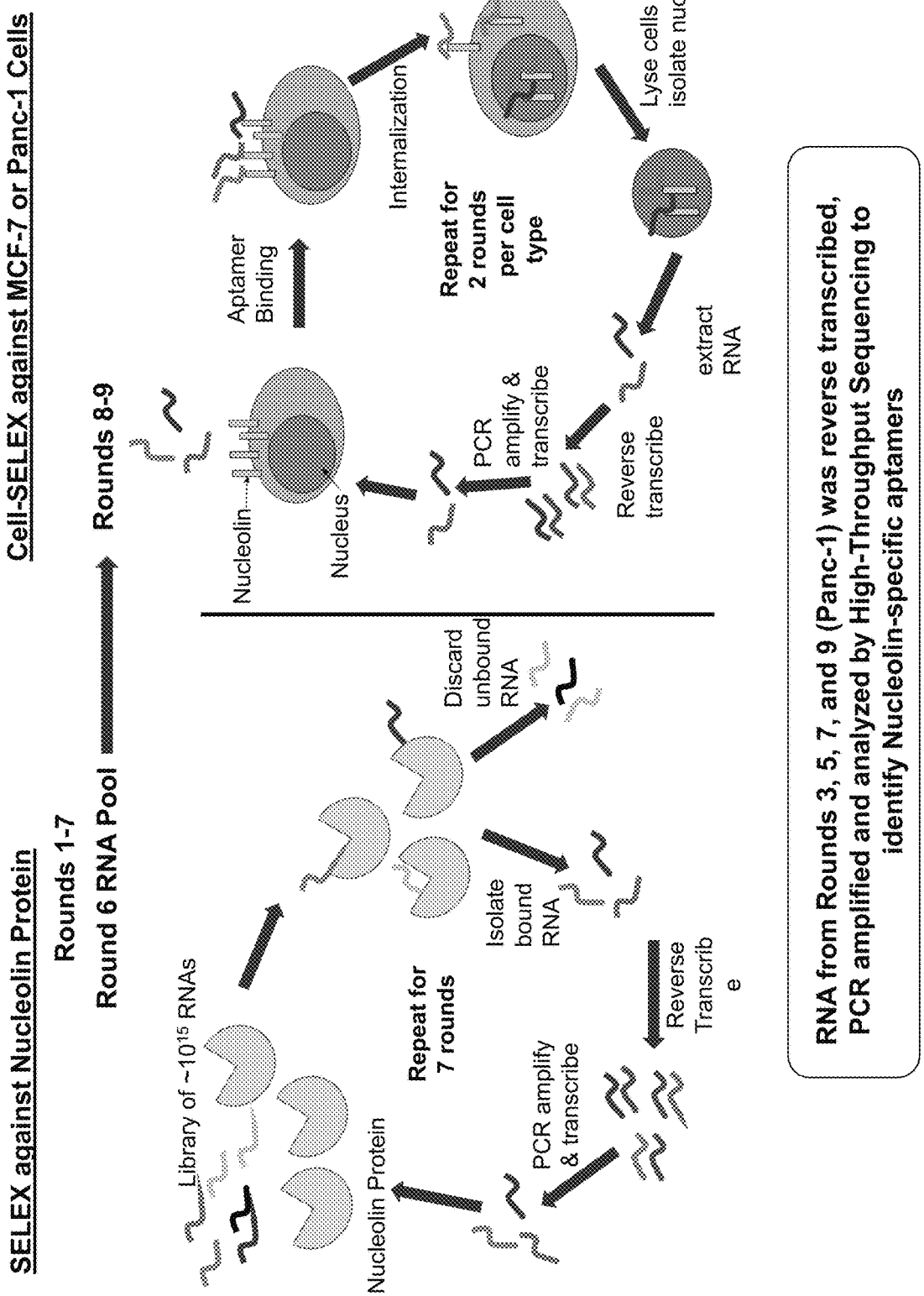
FIG. 1 shows the work flow demonstrating the selection of aptamer families capable of relocating into the nucleus after binding to nucleolin on cell surface. A random 2'Fluoro-pyrimidine RNA pool of sequences GGGAGAGAGGAAGAGGGAUGGG (SEQ ID NO: 491)-$N_{40}$-CAUAACCCAGAGGUCGAUAGUACUG-GAUCCCCCC (SEQ ID NO: 492) (where $N_{40}$ represents 40 random nucleotides) was incubated for 20 min at 37° C. with nucleolin protein (in 20 mM Hepes, 150 mM NaCl, 2 mM $CaCl_2$ and 0.01% bovine serum albumin) at ratios of RNA: protein varying from 187:1 to 133:1. RNA bound to protein was isolated by filtration through a 0.45 µm nitrocellulose membrane before RNA extraction, reverse transcription, PCR amplification and transcription to complete 1 round of selection. Each subsequent round of selection used the RNA pool transcribed from the previous round of selection, for a total of 7 rounds of SELEX against the nucleolin protein. The Round 6 RNA pool was also used to perform 2 Cell-SELEX rounds against both MCF-7 and Panc-1 cells. For the Cell-SELEX rounds, the Round 6 RNA pool was incubated with either MCF-7 or Panc-1 cells for 2 hrs at 37° C./5% CO2 before using a high salt wash to remove non-internalized RNA. Cells were then tryspinized, washed again with high salt, and RNA extracted from the cell nuclei using the Invitrogen™ PARIS™ kit. RNA pools from Rounds 3, 5, 7 and 9 (Panc-1) were reverse transcribed, PCR amplified and analyzed by High-Throughput Sequencing.

Here, in the non-limiting Examples, the present inventors disclose new aptamers that may bind to and/or inhibit the nucleolin protein. The present inventors demonstrate that such aptamers may be useful not only to sensitize cancer cells to cancer treatments including, for example, ionizing radiation and chemotherapeutic agents, but also may facilitate the delivery of agents to the nucleus of a cell.

In one aspect of the present invention, aptamers are provided. As used herein, the term "aptamer" refers to single-stranded oligonucleotides that bind specifically to target molecules with high affinity. Aptamers can be generated against target molecules, such as nucleolin, by screening combinatorial oligonucleotide libraries for high affinity binding to the target (See, e.g., Ellington, Nature 1990; 346: 8 18-22 (1990), Tuerk, Science 249:505-1 0 (1990)). The aptamers disclosed herein may be synthesized using methods well-known in the art. For example, the disclosed aptamers may be synthesized using standard oligonucleotide synthesis technology employed by various commercial vendors including, without limitation, Integrated DNA Technologies, Inc. (IDT), Sigma-Aldrich, Life Technologies, or Bio-Synthesis, Inc.

The aptamer may include a polynucleotide having at least 50%, 60%, 70%, 80%, 85%, 90%, 91%, 92%, 93%, 94%, 95%, 96%, 97%, 98%, 99%, or 100% sequence identity to any one of SEQ ID NOS: 1-490, 494-515, or any one of the sequences described in the Tables or Figures disclosed herein (for example, Tables 1-4, 6-8 or FIG. 11A-11B, 12A-12B, 13A-13C, 14A-14D, 15A-15B, 16, 17, 18, 19, 20, 21, 22, 23, 24, 25, 26, 27, 28A-28B, 29, 30, 31, 32, 33, 34, 35, 36 or 37A-37B). The aptamers described herein (i.e., SEQ ID NOS: 1-490, 494-515) may or may not include a 5' constant region (GGGAGAGAGGAAGAGGGAUGGG (SEQ ID NO: 491)) that may be used, for example, to transcribe or purify the aptamers in vitro. The aptamers described herein (i.e., SEQ ID NOS: 1-490, 494-515) may or may not include a 3' constant region (CAUAACCCAGAG-GUCGAUAGUACUGGAUCCCCCC (SEQ ID NO: 492)) that may be used, for example, to transcribe or purify the aptamers in vitro. In some embodiments, the aptamer may include a polynucleotide having at least 50%, 60%, 70%, 80%, 85%, 90%, 91%, 92%, 93%, 94%, 95%, 96%, 97%, 98%, 99%, or 100% sequence identity to the polynucleotide sequence-5'-GGGAGAGAGGAAGAGGGAUGGG (SEQ ID NO: 491)-A Variable Region-CAUAACCCAGAGGU-CGAUAGUACUGGAUCCCCCC (SEQ ID NO: 492)-3', wherein the variable region may include any one of SEQ ID NOS: 13-473 or a portion thereof. The portion of the indicated aptamers should be capable of binding to nucleolin. In some embodiments, the aptamer may include a polynucleotide having at least 50%, 60%, 70%, 80%, 85%, 90%, 91%, 92%, 93%, 94%, 95%, 96%, 97%, 98%, 99%, or 100% sequence identity to SEQ ID NO: 480 (Ev3 Aptamer).

The terms "polynucleotide," "nucleotide sequence," "polynucleotide sequence," "nucleic acid" and "nucleic acid sequence" refer to a nucleotide, oligonucleotide, polynucleotide (which terms may be used interchangeably), or any fragment thereof. These phrases may refer to DNA or RNA of genomic, natural, or synthetic origin.

Regarding polynucleotide sequences, the terms "sequence identity," "percent identity," and "% identity" refer to the percentage of base matches between at least two nucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Sequence identity for a nucleotide sequence may be determined as understood in the art. (See, e.g., U.S. Pat. No. 7,396,664). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known nucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website.

Regarding polynucleotide sequences, sequence identity is measured over the length of an entire defined nucleotide sequence, for example, as defined by a particular sequence identified herein. Furthermore, sequence identity, as measured herein, is based on the identity of the nucleotide base in the nucleotide sequence, irrespective of any further modifications to the nucleotide sequence. For example, the polynucleotide nucleotide sequences described herein may include modifications to the nucleotide sequences such 2'flouro, 2'O-methyl, and inverted deoxythymidine (idT) modifications. These modifications are not considered in determining sequence identity. Thus if a base, for example, is a 2'fluoro adenine (or 2'O-methyl, etc.), it is understood to be an adenine for purposes of determining sequence identity with another sequence. Likewise, 3' idT modifications to the polynucleotide sequences described herein also should not be considered in determining sequence identity.

Based on the general aptamer structure presented, for example, in FIG. 11A-11B, 12A-12B, 13A-13C, 14A-14D, 15A-15B, 16, 17, 18, 19, 20, 21, 22, 23, 24, 25, 26, 27, 28A-28B, 29, 30, 31, 32, 33, 34, 35, 36 or 37A-37B, a person of ordinary skill in the art would readily recognize that several modifications could be made to the sequence while preserving the overall structure and presumably the function of the aptamer. For example, in FIG. 11A, a person of ordinary skill in the art could simply switch the first stem forming region GGGA and the tenth stem forming region UCCC to CCCU and AGGG, respectively, and still retain the stem structure of the aptamer. Additionally, modifications to the stem regions could be made that change the bases within the stem region but conserve the overall pyrimidine and purine base composition so that the stem region hybridizes at a similar melting temperature. A person of ordinary skill would also recognize that changes made to the aptamer that disturbed the general aptamer stem loop structure would likely result in an aptamer incapable of efficiently binding its target.

In some embodiments, the aptamer may have a dissociation constant ($K_D$) for the nucleolin protein that is less than 1000, 800, 600, 500, 450, 350, 250, 150, 125, 100, 90, 80, 70, 65, 60, 55, 50, 45, 40, 35, 30, 25, 20, 15, 10, 5, 2.5, 2, 1, 0.5, or 0.1 nanomolar (nM). The $K_D$ of an aptamer may be measured using the methodology used by the inventors in the Examples.

The aptamers may include a polynucleotide (RNA, DNA, or peptide nucleic acid (PNA)) that is in an unmodified form or may be in a modified form including at least one nucleotide base modification. Nucleotide base modifications of polynucleotides to, for example, protect the polynucleotide from nuclease degradation and/or increase the stability of the polynucleotide and are well-known in the art. Common nucleotide base modifications that may be used in accordance with the present invention include, without limitation, deoxyribonucleotides, 2'-O-Methyl bases, 2'-Fluoro bases, 2' Amino bases, inverted deoxythymidine bases, 5' modifications, and 3' modifications. In some embodiments, the aptamer may include a polynucleotide including a modified form including at least one nucleotide base modification selected from the group consisting of a 2'fluoro modification, a 2'O-methyl modification, a 5' modification, and a 3'modification.

Typical 5' modifications may include, without limitation, inverted deoxythymidine bases, addition of a linker sequence such as C6, addition of a cholesterol, addition of a reactive linker sequence which could be conjugated to another moiety such as a PEG. Typical 3' modifications may include, without limitation, inverted deoxythymidine bases, and inverted abasic residues.

As additional 5' and/or 3' modifications, the aptamer may include a polynucleotide including a 5' linker and/or a 3' linker. Common 5' and/or 3' linkers for polynucleotides are known in the art and may include peptides, amino acids, nucleic adds, as well as homofunctional linkers or heterofunctional linkers. Particularly useful conjugation reagents that can facilitate formation of a covalent bond with an aptamer may comprise an N-hydroxysuccinimide (NHS) ester and/or a maleimide or using click chemistry. Typical 5' and/or 3' linkers for polynucleotides may include without limitation, amino C3, C4, C5, C6, or C12-linkers. The aptamer may further include an agent. Suitable agents may include, without limitation, stability agents, detectable agents such as reporter moieties, and/or therapeutic agents.

As used herein, a "stability agent" refers to any substance (s) that may increase the stability and/or increase the circulation time of a polynucleotide in vivo. Typical stability agents are known in the art and may include, without limitation, polyethylene glycol (PEG), cholesterol, albumin, or Elastin-like polypeptide.

As used herein, a "detectable agent" refers to any substance(s) that may be detected using appropriate equipment. Suitable detectable agents may be, without limitation, a fluorophore moiety, an enzyme moiety, an optical moiety, a magnetic moiety, a radiolabel moiety, an X-ray moiety, an ultrasound imaging moiety, a photoacoustic imaging moiety, a nanoparticle-based moiety, or a combination of two or more of the listed moieties.

A "fluorophore moiety" may include any molecule capable of generating a fluorescent signal. Various fluorophore moieties are well-known in the art and/or commercially available. Exemplary fluorophore moieties include, without limitation, fluorescein, FITC, Alexa Fluor 488, Alexa Fluor 660, Alexa Fluor 680, Alexa Fluor 750, and Alexa Fluor 790 (Life Technologies); Cy2, Cy3, Cy3.5, Cy5, Cy5.5 and Cy7 (GE Healthcare); DyLight 350, DyLight 488, DyLight 594, DyLight 650, DyLight 680, DyLight 755 (Life Technologies); IRDye 800CW, IRDye 800RS, and IRDye 700DX (Li-Cor); VivoTag680, VivoTag-S680, and VivoTag-S750 (PerkinElmer).

An "enzyme moiety" refers to polypeptides that catalyze the production of a detectable signal. Exemplary enzyme moieties may include, without limitation, horseradish peroxidase (HRP), alkaline phosphatase (AP), glucose oxidase, or β-galactosidase.

"Optical moieties" may include, for example, any agents that may be used to produce contrast or signal using optical imaging such as luminescence or acousto-optical moieties.

"Magnetic moieties" may include, for example, a chelating agent for magnetic resonance agents. Chelators for magnetic resonance agents can be selected to form stable complexes with paramagnetic metal ions, such as Gd(III), Dy(III), Fe(III), and Mn(II).

Other exemplary detectable agents may include radiolabel moieties. Exemplary radioactive labels may include, without limitation, $^{99}$Mo, $^{99m}$Tc, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{n}$C, $^{x3}$N, $^{15}$O, and $^{18}$F.

"X-ray moieties" may include, for example, any agents that may be used to produce contrast or signal using X-ray imaging such as iodinated organic molecules or chelates of heavy metal ions.

"Photoacoustic imaging moieties" may include photoacoustic imaging-compatible agents such as methylene blue, single-walled carbon nanotubes (SWNTs), and gold nanoparticles. Ultrasound imaging moieties may include, for example, any agents that may be used to produce contrast or signal using ultrasound imaging such as Levovist, Albunex, or Echovist.

A detectable agent may also be a nanoparticle-based moiety. A nanoparticle-based moiety is a nanoparticle that is capable of generating a signal. For example, silicon containing nanoparticles may be used to produce fluoresecence, luminescence, or another type of signal. Other exemplary nanoparticle-based moieties include, without limitation, nanospheres such as Kodak X-SIGHT 650, Kodak X-SIGHT 691, Kodak X-SIGHT 751 (Fisher Scientific); metal oxide nanoparticles; and quantum dots such as Evi-Tags (Evident Technologies) or Qdot probes (Life Technologies).

As used herein, a "therapeutic agent" may be any substance that provides a therapeutic functionality when conjugated to any one of the aptamers described herein. Suitable therapeutic agents may include, without limitation, cytotoxic compounds, and particularly those shown to be effective in other drug conjugates. As used herein, a "cytotoxic compound" refers to any substance that disrupts the functioning of cells and/or causes the death of cells. Various therapeutic cytotoxic compounds are known in the art and may include, without limitation, DNA damaging agents, anti-metabolites, natural products and their analogs. Exemplary classes of cytotoxic compounds include enzyme inhibitors such as dihydrofolate reductase inhibitors, and thymidylate synthase inhibitors, tubulin inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, auristatins, maytansinoids, differentiation inducers, and taxols. More specifically, suitable cytoxic compounds may include: 5-fluorouracil, aclacinomycin, activated cytoxan, bisantrene, bleomycin, carmofur, CCNU, cis-platinum, daunorubicin, doxorubicin, DTIC, melphalan, methotrexate, mithromycin, mitomycin, mitomycin C, peplomycin pipobroman, plicamycin, procarbazine, retinoic acid, tamoxifen, taxol, tegafur, VP16, VM25, diphtheria toxin, botulinum toxin, geldanamycin, maytansinoids (including DM1), monomethylauristatin E (MMAE), monomethylauristatin F (MMAF), and maytansinoids (DM4) and their analogues. Exemplary cytotoxic compounds may also include therapeutic radiopharmaceuticals including, without limitation, $^{186}$Re, $^{188}$Re, $^{153}$Sm, $^{67}$Cu, $^{105}$Rh, $^{m}$Ag, and $^{192}$Ir.

The aptamer and agent may be "linked" either covalently or non-covalently. Additionally, the aptamer and agent may be linked using the 5' and/or 3' linkers described herein. The aptamer and agent may be linked at the 5' end and/or the 3' end of the aptamer. To link the aptamer and agent non-covalently, the aptamer and the agent may be linked by a tag system. A "tag system" may include any group of agents capable of binding one another with a high affinity. Several tag systems are well-known in the art and include, without limitation, biotin/avidin, biotin/streptavidin, biotin/NeutrAvidin, or digoxigenin (DIG) systems. In some embodiments, the tag system comprises biotin/avidin or biotin/streptavidin. In such embodiments, the aptamer may be modified at either the 5' or 3' end to include biotin while the agent may be modified to include streptavidin or avidin. Alternatively, the aptamer may be modified at either the 5' or 3' end to include streptavidin or avidin while the agent may be modified to include biotin.

In another aspect, the present invention relates to dimers, trimers, and tetramers including any one of the aptamers described herein. A "dimer" refers to the linking together of two aptamer molecules in order to, for example, to increase the stability and/or increase the circulation time of a polynucleotide in vivo. A "trimer" refers to the linking together of three aptamer molecules in order to, for example, to increase the stability and/or increase the circulation time of a polynucleotide in vivo. A "tetramer" refers to the linking together of four aptamer molecules in order to, for example, to increase the stability and/or increase the circulation time of a polynucleotide in vivo. The aptamer molecules may be linked together covalently, noncovalently, or a combination of both. The aptamer molecules may be linked at their 5' or 3' ends. To link the aptamers noncovalently, the aptamers may be linked by a tag system or through a scaffold system.

In a further aspect of the present invention, pharmaceutical compositions including any of the aptamers described herein are provided. The pharmaceutical compositions may include a pharmaceutical carrier, excipient, or diluent (i.e., agents), which are nontoxic to the cell or mammal being exposed thereto at the dosages and concentrations employed. Often a pharmaceutical composition may include an aqueous pH buffered solution. Examples of pharmaceutical carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ brand surfactant, polyethylene glycol (PEG), and PLURONICS™ surfactant. In some embodiments, the pharmaceutical carrier may include a buffer including about 20 mM Hepes, pH 7.4; 150 mM NaCl; 1 mM $CaCl_2$); 1 mM $MgCl_2$; 5 mM KCl.

In a still further aspect, the present invention relates to methods for treating cancer in a subject. The methods may include administering to the subject a therapeutically effective amount of any one of the aptamers, dimers, trimers, tetramers, or pharmaceutical compositions described herein. The subject may be any mammal, suitably a human, domesticated animal such as a dog or cat, or a mouse or rat. Optionally, the present methods may further include administering a chemotherapeutic agent or radiation therapy to the subject.

Exemplary cancers in accordance with the present invention include, without limitation, colon, primary and metastatic breast, ovarian, liver, pancreatic, prostate, bladder, lung, osteosarcoma, pancreatic, gastric, esophageal, skin cancers (basal and squamous carcinoma; melanoma), testicular, colorectal, urothelial, renal cell, hepatocellular, leukemia, lymphoma, multiple myeloma, head and neck, and central nervous system cancers or pre-cancers.

Treating cancer includes, but is not limited to, reducing the number of cancer cells or the size of a tumor in the subject, reducing progression of a cancer to a more aggressive form, reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc.

Optionally, the present methods may further include administering a chemotherapeutic agent and/or radiation therapy to the subject. Without being limited by theory, the present inventors conjecture (and demonstrate in the Examples) that aptamers that block nucleolin function in cancer cells can sensitize cancer cells to DNA-damaging agents such as chemotherapeutic agents and radiation therapy. In some embodiments, the aptamer-containing composition described herein is administered prior to, simultaneously with, or after the chemotherapeutic agent and/or radiation therapy. In some embodiments, the aptamer-containing composition is administered prior to the administration of the optional chemotherapeutic agent and/or radiation therapy.

Chemotherapeutic agents are compounds that may be used to treat cancer. Suitable chemotherapy agents may include, without limitation, 5-fluorouracil, aclacinomycin, activated cytoxan, bisantrene, bleomycin, carmofur, CCNU, cis-platinum, daunorubicin, doxorubicin, DTIC, melphalan, methotrexate, mithromycin, mitomycin, mitomycin C, peplomycin pipobroman, plicamycin, procarbazine, retinoic acid, tamoxifen, taxol, tegafur, VP16, or VM25. In some embodiments, the chemotherapeutic agent may be a DNA-damaging agent including, without limitation, cisplatin carboplatin, picoplatin, oxaliplatin, methotrexate, doxorubicin, or daunorubicin, 5-fluorouracil. capecitabine, floxuridine, and gemcitabine, and the purine analogs 6-mercaptopurine, 8-azaguanine, fludarabine, and cladribine. The optional radiation therapy in the present methods may include one or more doses of between 1 Gy and 30 Gy. Suitably, the radiation therapy includes a single fraction dose of 12, 15, 18, 20, 21, 23, 25, or 28 Gy.

The chemotherapeutic agent and/or radiation therapy may be administered in any order in relation to the aptamer-containing compositions described herein, at the same time or as part of a unitary composition. The aptamer-containing composition and chemotherapeutic agent and/or radiation therapy may be administered such that one composition or therapy is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks or more.

An "effective amount" or a "therapeutically effective amount" as used herein means the amount of a composition that, when administered to a subject for treating a state, disorder or condition is sufficient to effect a treatment (as defined above). The therapeutically effective amount will vary depending on the composition, formulation or combination, the disease and its severity and the age, weight, physical condition and responsiveness of the subject to be treated. The compositions (i.e., those including the aptamers described herein) described herein may be administered by any means known to those skilled in the art, including, but not limited to, intratumoral, oral, topical, intranasal, intraperitoneal, parenteral, intravenous, intramuscular, subcutaneous, intrathecal, transcutaneous, nasopharyngeal, or transmucosal absorption. Thus the compositions may be formulated as an ingestable, injectable, topical or suppository formulation. Within broad limits, administration of larger quantities of the aptamer-containing compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the aptamer-containing compositions being administered, the disease to be treated or inhibited, the condition of the subject, and other relevant medical factors that may modify the activity of the compositions or the response of the subject, as is well known by those skilled in the art. For example, the specific dose for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the compound will reduce symptoms of the condition at least 10%, 20%, 30%, 40%, 50%, 60%, 70%, 80%, 90% or 100% compared to pre-treatment symptoms or symptoms is left untreated. It is specifically contemplated that pharmaceutical preparations and compositions may palliate or alleviate symptoms of the disease without providing a cure, or, in some embodiments, may be used to cure the disease or disorder.

The effectiveness of the aptamer-containing composition in treating the cancer or reducing the likelihood of resistance can be measured by tracking the growth of the tumor or the growth rate of the tumor or cancer cells. A decrease in tumor size or in the rate of tumor growth is indicative of treatment of the cancer.

The aptamers disclosed herein may also be used in methods of labeling or inhibiting nucleolin. As disclosed herein the aptamers provided bind to nucleolin and may be used to inhibit nucleolin. In some instances the aptamers are trafficked with the nucleolin to the nucleus of the cell when the aptamer is contacts the cell. The aptamers may be combined with an agent as described above and if the agent is a reporter moiety the agent may allow nucleolin to be labeled within the cell or to bring the agent in contact with nucleolin. Nucleolin may be contacted with the aptamer directly or indirectly in vivo, in vitro, or ex vivo. Contacting encompasses administration to a cell, a culture of cells, tissue, mammal, patient, or human expressing nucleolin. Further, contacting a cell includes adding an agent to a cell culture. Other suitable methods may include introducing or administering an agent to a cell, tissue, mammal, or patient using appropriate procedures and routes of administration as defined above.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Development of Nucleolin-Binding Aptamers

Figure 2A:
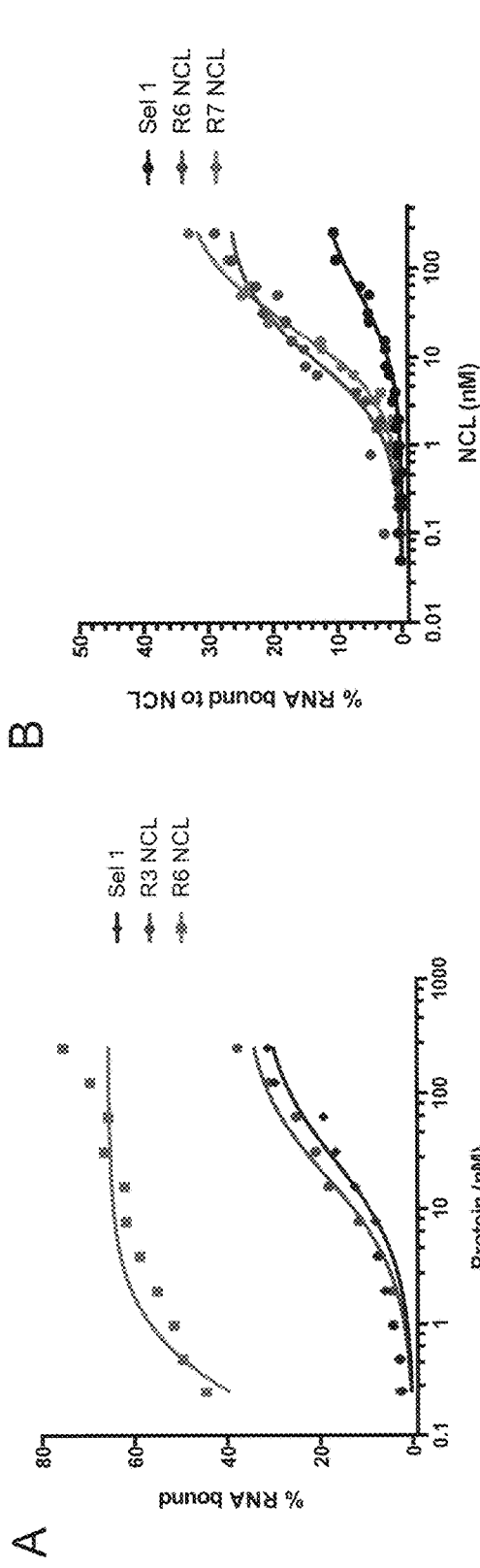
FIGS. 2A-2D show binding of the SELEX and Cell-SELEX rounds to the nucleolin protein (NCL). RNA pools from SELEX rounds 3, 6, and 7 or from Cell-SELEX Rounds 7-8 MCF-7 or Rounds 7-8 Panc-1 were end-labeled with $^{32}$P. Nucleolin protein was serially diluted in 20 mM Hepes, 150 mM NaCl, 2 mM CaCl$_2$ and 0.01% bovine serum albumin and incubated with a trace amount of the $^{32}$P-labeled RNA pools. After incubation at 37° C., unbound RNA was captured on a nylon membrane and RNA-nucleolin complexes captured on a nitrocellulose membrane. The fraction of protein-bound RNA was determined via phosphorimaging of the nitrocellulose and nylon membranes.
Figure 2B:
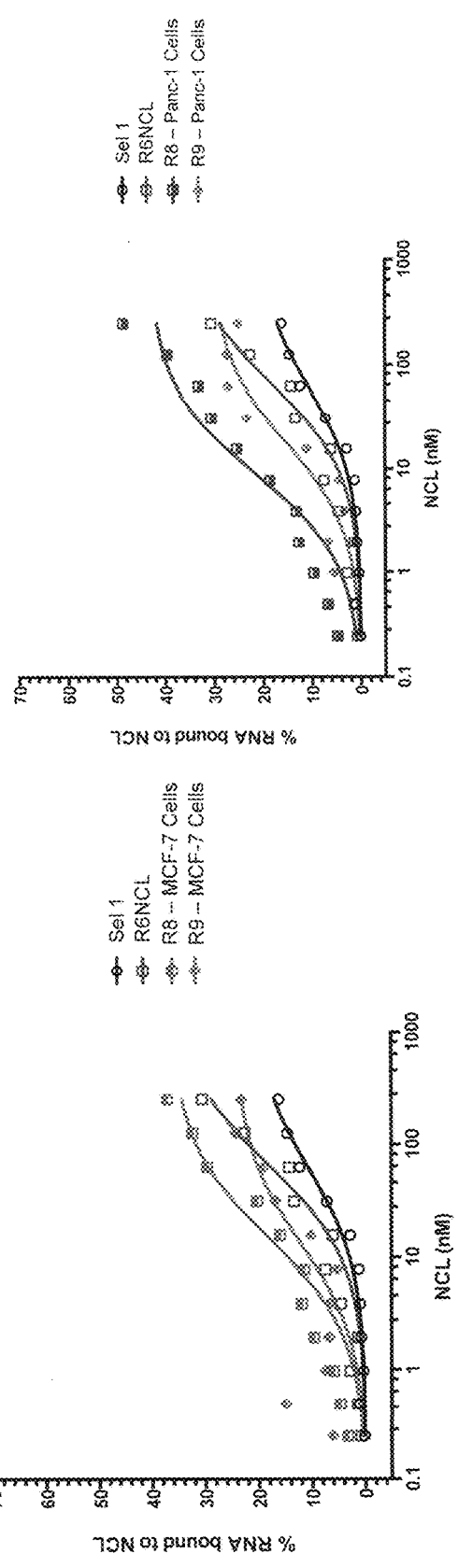
Figure 2C:
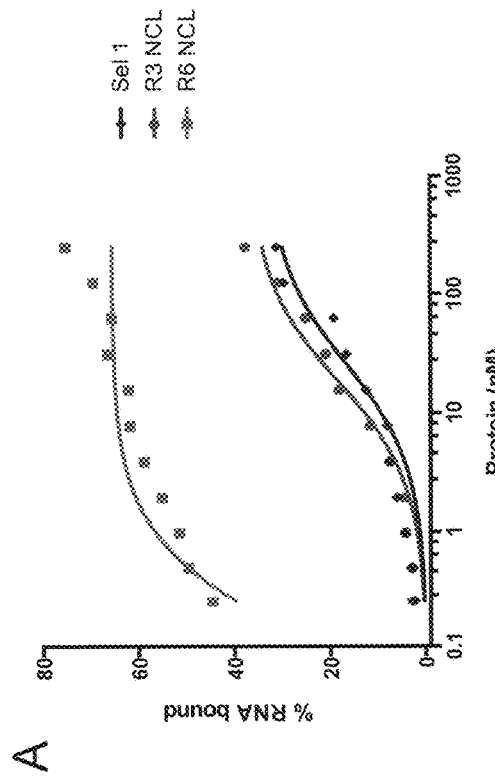
Figure 2D:
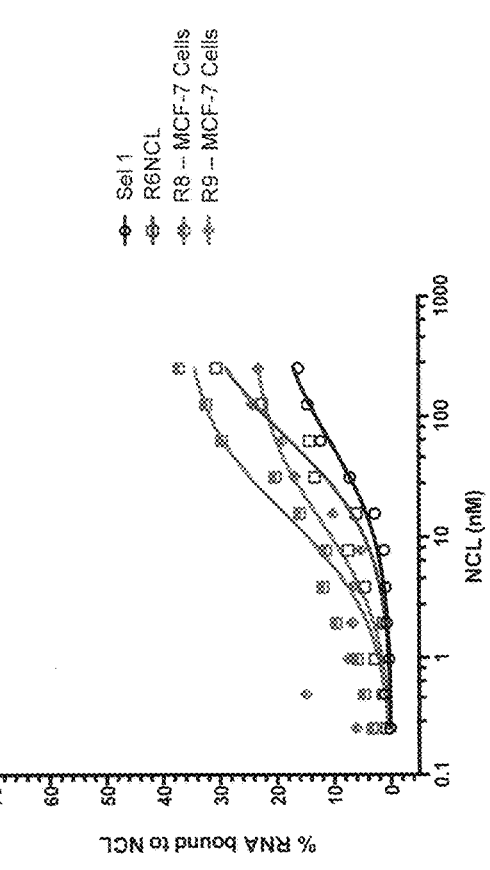
Figure 5B:
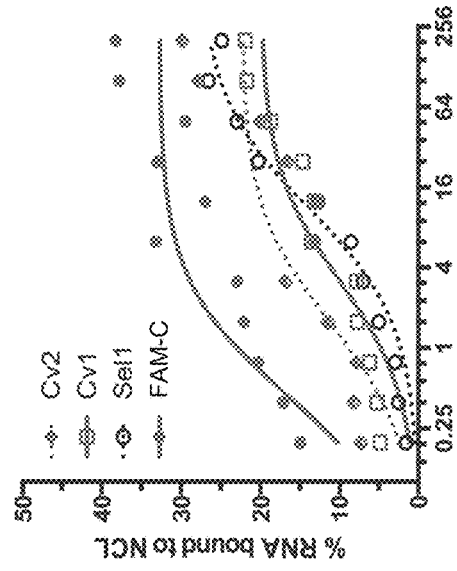
FIGS. 5A-5F show binding of nucleolin aptamer truncates to the nucleolin protein. Aptamers were end-labeled with $^{32}$P. Nucleolin protein was serially diluted in 20 mM Hepes, 150 mM NaCl, 2 mM CaCl$_2$) and 0.01% bovine serum albumin and incubated with a trace amount of the $^{32}$P-labeled RNA pools. After incubation at 37° C., unbound RNA was captured on a nylon membrane and RNA-nucleolin complexes captured on a nitrocellulose membrane. The fraction of protein-bound RNA was determined via phosphorimaging of the nitrocellulose and nylon membranes.
Figure 5D:
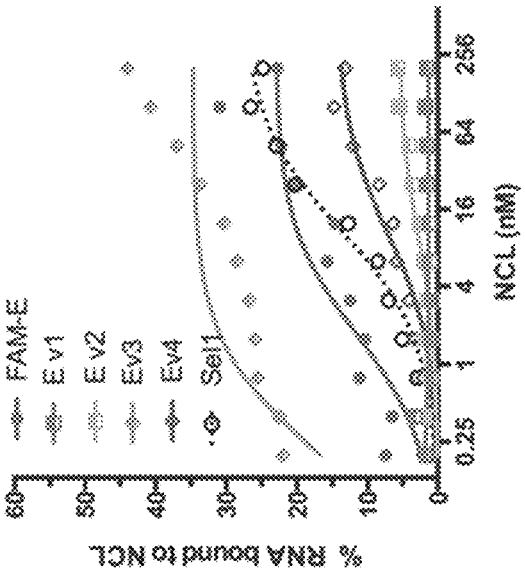
Figure 5A:
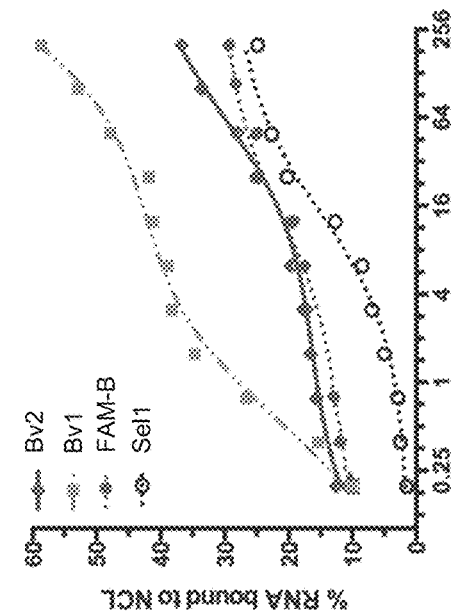
Figure 5C:
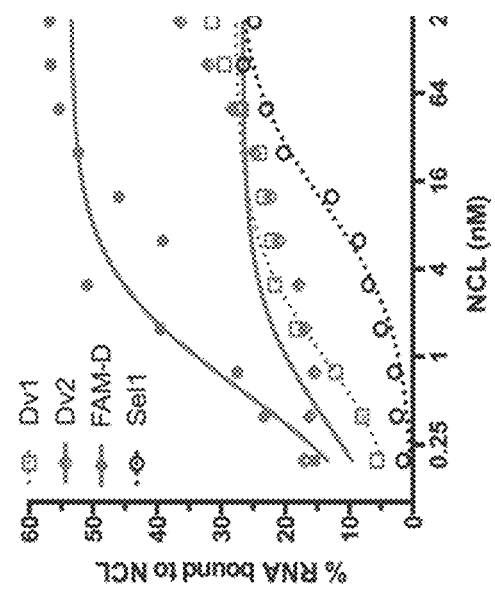
Figure 5F:
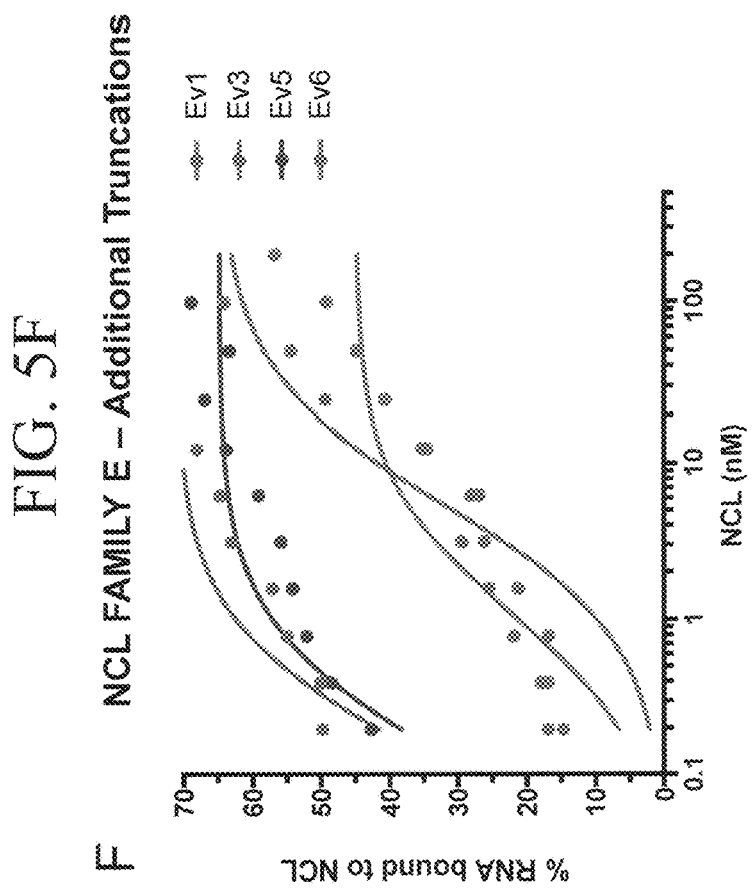
Figure 5E:
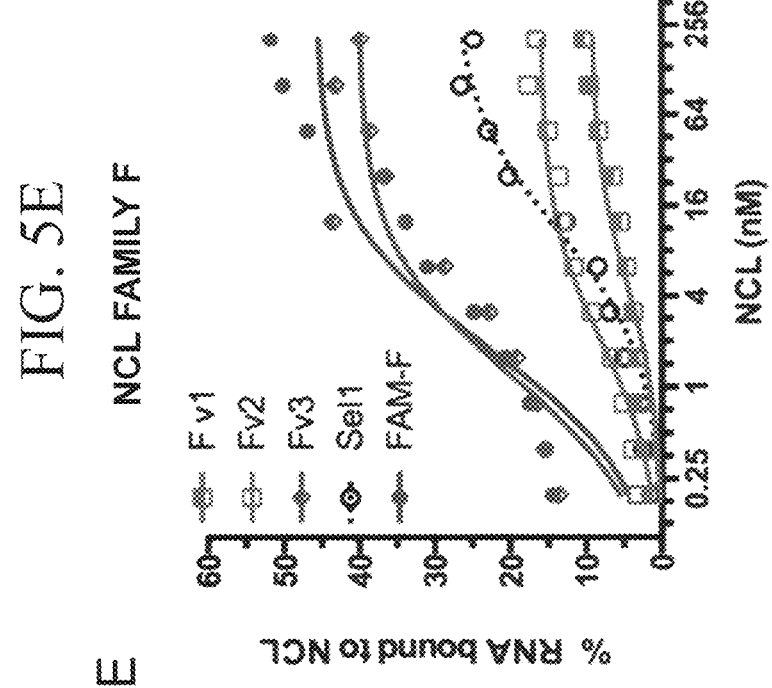

With the goal of developing an aptamer that binds and/or inhibits the nucleolin protein, we performed a dual protein and cell selection via systematic evolution of ligands by exponential enrichment (SELEX) using a modified RNA library (FIG. 1). First, SELEX was performed against a recombinant nucleolin protein (SEQ ID NO: 493) resulting in an RNA library enriched in clones specific for nucleolin after 6 rounds of selection (FIG. 2A). As a $7^{th}$ round of SELEX did not improve the aptamer pool's affinity for the nucleolin protein (FIG. 2B), we moved forward with the pool of RNA from the $6^{th}$ round of SELEX (R6 NCL). To identify nucleolin-specific RNAs capable of binding to nucleolin on cell surface and subsequently transporting to the nucleus, the R6 NCL RNA pool was incubated with either MCF-7 or Panc-1 cells (FIG. 1). The nuclei were then isolated and the aptamer pool that reached this compartment was amplified. After 2 rounds of cellular selection with either MCF-7 or Panc-1 cells, the RNA library was further enriched for aptamers capable of binding to the nucleolin protein (FIGS. 2C & 2D).

We previously demonstrated that nucleolin interacts with Rad50, a member of the MRN complex, through its C-terminal RGG domain and that this interaction is essential for recruitment of nucleolin to the DNA damage site and repair of the DSB (Goldstein et al. 2013, PNAS). Thus, we estimated that in order to achieve a disruption of the nucleolin-Rad50 interaction and the inhibition of DSB repair required for radiosensitization, our nucleolin aptamer would need to bind to either the RGG domain itself or to the RBD domain in the proximity of the C-terminus. In fact, we found that the R6 NCL RNA aptamer pool binds to the RBD domain (FIGS. 3A-3B), suggesting that these aptamers may be able to inhibit the nucleolin-Rad50 interaction that is crucial for DSB repair.

High throughput sequencing of the SELEX pools from various selection rounds (rounds 3, 5, 7, and 9—Panc-1 round 2), resulted in almost 8000 unique RNA families plus 78 ambiguous sequences, where RNA families are RNA sequences that differ by 4 nucleotides or less and ambiguous sequences are single RNA sequences that do not fit into a RNA family. The most representative sequence from each of the top 6 abundant families, designated Families A-F (FAM-A, etc., Tables 1-4), were transcribed to test their ability to bind to the nucleolin protein. Families B-F demonstrated specific binding to nucleolin while Family A did not appear to significantly bind the protein, suggesting that it may be an artifact resulting from PCR amplification (FIG. 4, Table 5). To make it easier to chemically synthesize the nucleolin aptamers, we sought to shorten their length. Thus, we designed truncates of the Families B-F aptamers (Tables 6-8). Several of these truncations resulted in improved affinity for nucleolin over the parent aptamers, with truncations Bv1, Dv2, Ev3, Ev5, and Fv3 demonstrating the best affinity (FIGS. 5A-5F). To further truncate the Ev3 aptamer, we designed 24 additional truncates of Ev3 (Tables 7 and 8). Several of these truncations, primarily Ev3.min21, Ev3.min22, and Ev3.min24 demonstrated a similar affinity for nucleolin compared to their parent Ev3 aptamer (FIGS. 9A-9D).

TABLE 1

Nucleolin Aptamer Sequences without 5' and 3' Constant Regions

| NCL Aptamer | Sequence |
|---|---|
| FAM-A | CCAUCUAGAUCUCCGUAGAUUCCCCCGGCUCUUUCUCGC (SEQ ID NO: 1) |
| FAM-B | AGCCAGCUUUGCAUACCACGUGCAAUUCACUCCACCCGUCA (SEQ ID NO: 2) |
| FAM-C | AAGAUCUGCUAAGUGCACGCACAAUCACCAUCGAGCGUCU (SEQ ID NO: 3) |
| FAM-D | CACAUGGUACGCCCAAAGCGAGGCCCGCUGCGUAGUGC (SEQ ID NO: 4) |
| FAM-E | CACGGUCCAGCGCUAACUGUACCUGCUGUGCCACCCACCG (SEQ ID NO: 5) |
| FAM-F | ACCACGCGCCAACGUGUCAGCUACACGCCGUGUUCCCCGG (SEQ ID NO: 6) |

TABLE 2

Nucleolin Aptamer Sequences with 5' and 3' Constant Regions

| NCL Aptamer | Sequence |
|---|---|
| FAM-A | GGGAGAGAGGAAGAGGGAUGGGCCAUCUAGAUCUCCGUAGAUUCCCCGGCUCUUUCUCGCCAUAACCCAGAGGUCGAUAGUACUGGAUCCCCCC (SEQ ID NO: 7) |
| FAM-B | GGGAGAGAGGAAGAGGGAUGGGAGCCAGCUUUGCAUACCACGUGCAAUUCACUCCACCCGUCACAUAACCCAGAGGUCGAUAGUACUGGAUCCCCCC (SEQ ID NO: 8) |

TABLE 2-continued

Nucleolin Aptamer Sequences with 5' and 3' Constant Regions

| NCL Aptamer | Sequence |
|---|---|
| FAM-C | GGGAGAGAGGAAGAGGGAUGGGAAGAUCUGCUAAGUGCACGCACAAU CACCAUCGAGCGUCUCAUAACCCAGAGGUCGAUAGUACUGGAUCCCCC C (SEQ ID NO: 9) |
| FAM-D | GGGAGAGAGGAAGAGGGAUGGGCACAUGGUACGCCCAAAGCGAGGCC CGCUGCGUAGUGCCAUAACCCAGAGGUCGAUAGUACUGGAUCCCCCC (SEQ ID NO: 10) |
| FAM-E | GGGAGAGAGGAAGAGGGAUGGGCACGGUCCAGCGCUAACUGUACCUG CUGUGCCACCCACCGCAUAACCCAGAGGUCGAUAGUACUGGAUCCCCC C (SEQ ID NO: 11) |
| FAM-F | GGGAGAGAGGAAGAGGGAUGGGACCACGCGCCAACGUGUCAGCUACA CGCCGUGUUCCCCGGCAUAACCCAGAGGUCGAUAGUACUGGAUCCCCC C (SEQ ID NO: 12) |

TABLE 3

Representative Nucleolin Aptamer Sequences without 5' and 3' Constant Regions from All Families

| Family Name | Representative Sequence | SEQ ID NO: |
|---|---|---|
| A | CCAUCUAGAUCUCCGUAGAUUCCCCCGGCUCUUUCUCGC | 13 |
| B | AGCCAGCUUUGCAUACCACGUGCAAUUCACUCCACCCGUCA | 14 |
| C | AAGAUCUGCUAAGUGCACGCACAAUCACCAUCGAGCGUCU | 15 |
| D | CACAUGGUACGCCCAAAGCGAGGCCCGCUGCGUAGUGC | 16 |
| E | CACGGUCCAGCGCUAACUGUACCUGCUGUGCCACCCACCG | 17 |
| F | ACCACGCGCCAACGUGUCAGCUACACGCCGUGUUCCCCGG | 18 |
| G | AAGAUCCUCGCGCAUCUGCCGAGCAAUCACCAUCGGACG | 19 |
| H | CCAAAUGCCAAGCCGUAGCCCGGCCAGUAGCCCACACGUC | 20 |
| I | UGCCAAGCCGAGGCCCGGCCACCAUCCACUGAUAGUGGGC | 21 |
| J | AAGAUCCUGACGCGACACAGCAAUCACCAUCGAACCAGCU | 22 |
| K | AAGAUCUGCGGCAACGCACAAUCACCAUCGAUUCCGAAUU | 23 |
| L | GAGCUCUCGAUUUCCUCCGCGACACCCAUCCAAACCUCA | 24 |
| M | CUCUCCGGUCUACCAUCCGGACCGGCGACAAAGUCAACUU | 25 |
| N | AAGAUCUGCUAUGCACAAUCACCAUCGGGCGCUCCGGGGAA | 26 |
| O | UUGACUCUGCUGCGUAGUUCGCACCAAGAUCAACCACUUC | 27 |
| P | UACCAAGUCGUGGCCCGACUACCCAGCACGAUGCGCAA | 28 |
| Q | CUAUUCGAGUUCCCACGAAUCCCCCCAUCGAGAACCUAC | 29 |
| R | UGCCAAGCCGAGGCCCGGCCACCGUCCCCGCGGCUGAUGA | 30 |
| S | AAUGAUCUCGCCAAUGGGCGACAAUCACCAUGUCUUCACA | 31 |
| T | UCAGUGCGCCAAGUGGAGGCCCCACCGCAGCCCAUCAA | 32 |
| U | UGUAUGCCAGCUUUGACGAUAACUGUCGCGCGUCAAUUCA | 33 |
| V | UACGCCAAAGUGGAGCCCACUCGUACCCCAUCAUGAGCUG | 34 |
| W | CCGCCAGCUUUGGGUACCCUGACCAAUUCACGGCCAUCCA | 35 |
| X | GUAAUUGCUGAGACCACCGGACAAUCAACAAGAAAUCCU | 36 |

TABLE 3-continued

Representative Nucleolin Aptamer Sequences without 5' and 3' Constant Regions from All Families

| Family Name | Representative Sequence | SEQ ID NO: |
|---|---|---|
| Y | UCAGGCCAAAGUGUGAUAGCCACACCCGCACCCAUCAGGA | 37 |
| Z | CCGACCGCCGACCAGGGUGCCACUCGUACCCCUGUCCGCC | 38 |
| AA | UGCCAAGUCGAAGCCCGACCACGCCAUCCCUAACAGUGCC | 39 |
| AB | ACUUGUGCUGAGUCGCCAAAGUGAGGCCCACUCGCCAGCA | 40 |
| AC | CCGCCAGCUCCUCUGAGGCACAAGAGGUUCACGGUGAUCC | 41 |
| AD | CACCAGGUUCUGCUGUCCCCAAGCGCUGACCCAUCCUUCC | 42 |
| AE | AAGAUCCGGUAACUCCCCACCGCAAUCACCGUCGACUACU | 43 |
| AF | CCAUCUAGAUCUCCGUAGAUUCCCCCGGCUCUUUCUCGC | 44 |
| AG | CCAUCUGAACCCACAGAUUCCCCCAUCAUCAGCCACAGUG | 45 |
| AH | CACUAAGUUGGUAGCCCCAACUGCCCCGACACGAGGAUGU | 46 |
| AI | UUGUGCUCCGUGGCUCCCCGGACCAACCGCUUCCAGCAGU | 47 |
| AJ | CAAUCACGCGUAGUACGUCGCGGAAGAUCCCCAUGCCGA | 48 |
| AK | CACAUGGUACGCCCAAAAGCGAGGCCCGCUGCGUAGUGC | 49 |
| AL | UGCCAUACGCGGUUCGAAGUCGAAGCCCGACAACCCGGCA | 50 |
| AM | GUUAUUCACAUGCCUCCCGUGAAUCAACAAGAAUUCCUUG | 51 |
| AN | AAAGAUCUAGACUGUAAGUCUCCAAUCGCCCAGUUAAUUC | 52 |
| AO | GCCCAAUCGCCAGUGGAACGCGCUGAAGGAUCUGCACCC | 53 |
| AP | UGCAACGUAAAAGAGAGUCAUCUCAGGCUAGUCGUCUACC | 54 |
| AQ | GUGUACGCCAAGUCGAGGCCCGACCGUACCCAUACGCGAC | 55 |
| AR | UUAGCUCUACUUUCCUCUUCAGUAAGACUAACCGCUUCUU | 56 |
| AS | UCCAAGCGGAGGCCCCGCACCCACCCUCCAACGGGCACGG | 57 |
| AT | UAUCGCUCCACAACGACUCCCGUGGACUACCCAAUUCCAA | 58 |
| AU | GUCGUGCCCAAGUGAAGGCCUCACGCACGCAUCCUAACCU | 59 |
| AV | AAGAUCUGCGCCAGCACAAUCACCAUCGUCCUGAGAAUGG | 60 |
| AW | AUGCCAAGCAGUGGCCCUGCCACCCACCUAUCACUGUCGA | 61 |
| AX | AACAGACCAAGCAGCGGCCCUGCUCUGCCAUCAUACGCCU | 62 |
| AY | GUCAUUCGCUGACGAAUCAACAUGAAUUCCUAACUGCUGA | 63 |
| AZ | ACACGCCAAGCUGGUAGCCCCAGCCGUGCCCAUUACGGCC | 64 |
| BA | UAGCCAAGCAGCAGCCCUGCCAACCCAUCCUACCCGGGCG | 65 |
| BB | GCCCAAGGCGAGGCCCGCCGUCCAUCCAGACGCUGAGGG | 66 |
| BC | AAGAUCUCGUCAUGCUUUGACGUCAAUCACCAUUGUUCCC | 67 |
| BD | AUCCCCAGGAUGAGCACGUUGCCAUGGACUGGCUAUCC | 68 |
| BE | CUGUUACAGUCUCGCGUAACCCCCCCAUCGAUGUCCUCGA | 69 |
| BF | AGCCAGCUUUCGGCAAACCGAAUUCACUCCACCCUGCUCA | 70 |
| BG | CACGGUAUAACCUCCUCAUAUACCUGCUGUGCCACCCGCG | 71 |
| BH | CCGGAAGAUCUGCUCGCACUAGCCGGAGCCCAAUCACGGC | 72 |
| BI | CCUGCCGAACGGCUAAGUCGCAGCCCGACCCGCGGCAGGG | 73 |

TABLE 3-continued

Representative Nucleolin Aptamer Sequences without 5' and 3' Constant Regions from All Families

| Family Name | Representative Sequence | SEQ ID NO: |
|---|---|---|
| BJ | CUCCGACCCGCGGACGAAGUCAACUUCCACAGUCCCACAC | 74 |
| BK | ACAUUAGGAUCUGCGUGAUGGGGAUCACCCGCUACAUGUC | 75 |
| BL | UCUAAGAUGGGGAAGAUCUCCGGAGCACCGGGCAAUCACC | 76 |
| BM | CUAUUCGAGUUCCCACGAAUCCCCCAUCGAGAACCUAC | 77 |
| BN | UGCCAAGCCGAGGCCCGGCCAGCAUCCCUCACGAGAGAGG | 78 |
| BO | GCCAAGCACGUAGCCCGUGCCCCCACCCGCCUGUGUGCUG | 79 |
| BP | UGCCAAGCACGAAGCCCGUGCCCCCAUCCAGAGUGUGAGA | 80 |
| BQ | AGCCAGCUUUUGCAUACCACGUGCAAUUCACUCCACCCGUCA | 81 |
| BR | CUUUGUAAACCCGGCAAACAAAAUCAACUUCCAUCAUCAA | 82 |
| BS | CCAUUGUAGCGACCACACAAUUCCCCAUCGGACAGCAUGG | 83 |
| BT | CUCUCGCCGUUCCCAGGCACGACAAAAUCAACUUCCCGCU | 84 |
| BU | AAGCCAAGCCGCGGCCCGGCCUUCCCAUGUGCUACUAGAG | 85 |
| BV | CCAAAUGCCAAAGCCGUAGCCCGGCCAGUAGCCCACACGUC | 86 |
| BW | CCAUUACGCGACGUAAUUCCCCCAUCGUUUCCUCGUUAAG | 87 |
| BX | CCAUCUAGAUCUCCGUAGAUUCCCCGGCUCUUUCUCGC | 88 |
| BY | ACUGUCUGCAUACACGGUAUGCCCAACGCCAUCCAAACCG | 89 |
| BZ | ACCUGCGGCUAUUGCCAGCGCCAUAAGACCCUCCACAGUA | 90 |

TABLE 4

Variant Nucleolin Aptamer Sequences without 5' and 3' Constant Regions from All Families

| Family Name | All Family Sequences | SEQ ID NO: |
|---|---|---|
| A | CCAUCUAGAUCUCCGUAGAUUCCCCCGGCUCUUUCUCGC | 91 |
|  | CCAUCUAGAUCUCCGUAGAUUCCCCCGGCUCUUCCUCGC | 92 |
|  | CCAUCUAGAUCUCCGUAGAUUCCCCCAGCUCUUUCUCGC | 93 |
| B | AGCCAGCUUUUGCAUACCACGUGCAAUUCACUCCACCCGUCA | 94 |
|  | AGCCAGCUUUUGCAUACCACGUGCAAUUCACUCCACCCGUCG | 95 |
| C | AAGAUCUGCUAAGUGCACGCACAAUCACCAUCGAGCGUCU | 96 |
|  | AAGAUCUGCUAAGUGCACGCACAAUCACCAUCGAGCGUCC | 97 |
|  | AAGAUCUGCUAAGUGCACGCACAAUCACCAUCGAGCGCCU | 98 |
|  | AAGAUCUGCUAAGUGCACGCACAAUCACCAUCGAGCGUC | 99 |
|  | AAGAUCUGCUAAGUGCACGCACAAUCACCAUCGAGCGACU | 100 |
| D | CACAUGGUACGCCCAAAGCGAGGCCCGCUGCGUAGUGC | 101 |
|  | CACACGGUACGCCCAAAGCGAGGCCCGCUGCGUAGUGC | 102 |
| E | CACGGUCCAGCGCUAACUGUACCUGCUGUGCCACCCACCG | 103 |
|  | CACGGUCCAGCGCUAACUGUACCUGCUGUGCCACCCACCA | 104 |
|  | CACGGUCCAGCGCUAACUGUACCUGCUGUGCCACCCACUG | 105 |
|  | CACGGUCCAGCGCUAACUGUACCUGCUGUGCCACCCACCU | 106 |
|  | CACGGUCCAGCGCUAACUGUACCUGCUGUGCCACCCGCCG | 107 |
| F | ACCACGCGCCAACGUGUCAGCUACACGCCGUGUUCCCCGG | 108 |
|  | ACCACGCGCCAACGUGUCAGCUACACGCCGUGUUCCCCGA | 109 |
|  | ACCACGCGCCAACGUGUCAGCUACACGCCGUGUUCCCCG | 110 |
|  | CCACGCGCCAACGUGUCAGCUACACGCCGUGUUCCCCGG | 111 |
| G | AAGAUCCUCGCGCAUCUGCCGAGCAAUCACCAUCGGACG | 112 |
|  | AAGAUCCUCGCGCAUCUGCCGAGCAAUCACCAUCGGACC | 113 |

TABLE 4-continued

Variant Nucleolin Aptamer Sequences without 5' and 3' Constant Regions from All Families

| Family Name | All Family Sequences | SEQ ID NO: |
|---|---|---|
| | AAGAUCCUCGCGCAUCUGCCGAGCAAUCACCAUCGGACA | 114 |
| | AAGAUCCUCGCGCAUCUGCCGAGCAAUCACCAUCGGACU | 115 |
| | AAAGAUCCUCGCGCAUCUGCCGAGCAAUCACCAUCGGACG | 116 |
| | AAGAUCCUCGCGCACCUGCCGAGCAAUCACCAUCGGACG | 117 |
| H | CCAAAUGCCAAGCCGUAGCCCGGCCAGUAGCCCACACGUC | 118 |
| | CCAAAAUGCCAAGCCGUAGCCCGGCCAGUAGCCCACACGUC | 119 |
| | CCAAAUGCCAAGCCGUAGCCCGGCCAGUAGCCCACACGAC | 120 |
| | CCAAAUGCCAAGCCGUAGCCCGGCCAGUAGCCCACACGUA | 121 |
| I | UGCCAAGCCGAGGCCCGGCCACCAUCCACUGAUAGUGGGC | 122 |
| | UGCCAAGCCGAGGCCCGGCCACCAUCCACUGAUAGUGGGA | 123 |
| | UGCCAAGCCGAGGCCCGGCCACCAUCCACUGAUAGUGGG | 124 |
| | UGCCAAGCCGAGGCCCGGCCACCAUCCACUGAUAGUGGGU | 125 |
| J | AAGAUCCUGACGCGACACAGCAAUCACCAUCGAACCAGCU | 126 |
| | AAGAUCCUGACGCGACACAGCAAUCACCAUCGAACCAGCC | 127 |
| K | AAGAUCUGCGGCAACGCACAAUCACCAUCGAUUCCGAAUU | 128 |
| | AAGAUCUGCGGCAACGCACAAUCACCAUCGAUUCCGAAUG | 129 |
| | AAGAUCUGCGGCAACGCACAAUCACCAUCGAUUCCGAAUC | 130 |
| | AAGAUCUGCGGCAACGCACAAUCACCAUCGAUUCCGAACU | 131 |
| | AAGAUCUGCGGCAACGUACAAUCACCAUCGAUUCCGAAUU | 132 |
| L | GAGCUCUCGAUUUCCUCCGCGACACCCAUCCAAACCUCA | 133 |
| | AGCUCUCGAUUUCCUCCGCGACACCCAUCCAAACCUCA | 134 |
| | GAGCUCUCGAUUUCCUCCGCGACACCCAUCCAAACCUCG | 135 |
| M | CUCUCCGGUCUACCAUCCGGACCGGCGACAAAGUCAACUU | 136 |
| | CUCUCCGGUCUACCACCCGGACCGGCGACAAAGUCAACUU | 137 |
| N | AAGAUCUGCUAUGCACAAUCACCAUCGGGCGCUCCGGGAA | 138 |
| | AAGAUCUGCUAUGCACAAUCACCAUCGGGCGCUCCGGGAA | 139 |
| | AAGAUCUGCUACGCACAAUCACCAUCGGGCGCUCCGGGAA | 140 |
| O | UUGACUCUGCUGCGUAGUUCGCACCAAGAUCAACCACUUC | 141 |
| | UUGACUCUGCUGCGUAGUUCGCACCAAGAUCAACCACUUCC | 142 |
| | UUGACUCUGCUGCGUAGCUCGCACCAAGAUCAACCACUUC | 143 |
| | UUGACUCUGCUGCGCAGUUCGCACCAAGAUCAACCACUUC | 144 |
| | UUGACUCUGCUGCGUAGUCCGCACCAAGAUCAACCACUUC | 145 |
| P | UACCAAGUCGUGGCCCGACUACCCAGCACGAUGCGCAA | 146 |
| | UACCAAAGUCGUGGCCCGACUACCCAGCACGAUGCGCAA | 147 |
| | UACCAAGUCGUGGCCCGACUACCCAGCACGGUGCGCAA | 148 |
| | UACCAAGUCGUGGCCCGACUACCCAGCACGAUGCGCAG | 149 |
| | UACCAAGUCGUGGCCCGACUACCCAGCACAAUGCGCAA | 150 |
| | UACCAAGUCGCGGCCCGACUACCCAGCACGAUGCGCAA | 151 |
| Q | CUAUUCGAGUUCCCACGAAUCCCCCCAUCGAGAACCUAC | 152 |
| | CUAUUCGAGUUCCCACGAAUCCCCCCAUCGAGAACCUA | 153 |
| | CUAUUCGAGUUCCCACGAAUCCCCCCAUCGAGAACCUAU | 154 |
| | CUAUUCGAGUUCCCACGAAUCCCCCCAUCGAGAACCUAA | 155 |
| R | UGCCAAGCCGAGGCCCGGCCACCGUCCCCGCGGCUGAUGA | 156 |
| | UGCCAAAGCCGAGGCCCGGCCACCGUCCCCGCGGCUGAUGA | 157 |
| | UGCCAAGCCGAGGCCCGGCCACCGUCCCCGCGGCUGAUCGA | 158 |
| | UGCCAAGCCGAGGCCCGGCCACCGUCCCCGCGGCUGAUGG | 159 |
| | UGCCAAGCCGAGGCCCGGCCACCGUCCCCGCGGCUGACGA | 160 |
| S | AAUGAUCUCGCCAAUGGGCGACAAUCACCAUGUCUUCACA | 161 |
| | AACGAUCUCGCCAAUGGGCGACAAUCACCAUGUCUUCACA | 162 |
| | AAUGAUCUCGCCAAUGGGCGACAAUCACCAUGUCUUCACG | 163 |
| | AAUGAUCUCGCCAAUGUGCGACAAUCACCAUGUCUUCACA | 164 |
| T | UCAGUGCGCCAAGUGGAGGCCCCACCGCAGCCCAUCAA | 165 |
| | UCAGUGCGCCAAGUGGAGGCCCCACCGCAGCCCAUCGA | 166 |
| | UCAGUGCGCCAAGUGGAGGCCCCACCGCAGCCCAUCAG | 167 |
| U | UGUAUGCCAGCUUUGACGAUAACUGUCGCGCGUCAAUUCA | 168 |
| V | UACGCCAAAGUGGAGCCCACUCGUACCCAUCAUGAGCUG | 169 |
| | UACGCCAAAGUGGAGCCCACUCGUACCCAUCAUGAGCCUG | 170 |
| | UACGCCAAAGUGGAGCCCACUCGUACCCAUCAUGAGCUC | 171 |
| | UACGCCAAAGUGGAGCCCACUCGUACCCAUCAUGGGCUG | 172 |

TABLE 4-continued

Variant Nucleolin Aptamer Sequences without 5' and 3' Constant Regions from All Families

| Family Name | All Family Sequences | SEQ ID NO: |
|---|---|---|
| | UACGCCAAAGUGGAGCCCACUCGUAUCCCAUCAUGAGCUG | 173 |
| | UACGCCAAAGUGGAGCCCACUCGUACCCCAUCGUGAGCUG | 174 |
| | UACGCCAAAGUGGAGCCCACUCGUACUCCAUCAUGAGCUG | 175 |
| | CACGCCAAAGUGGAGCCCACUCGUACCCCAUCAUGAGCUG | 176 |
| | UACGCCAAAGUGGAGCCCACUCGCACCCCAUCAUGAGCUG | 177 |
| | UACGCCAAAGUGGAGCCCACUCGUACCCCAUCAUGAGCUA | 178 |
| W | CCGCCAGCUUUGGGUACCCUGACCAAUUCACGGCCAUCCA | 179 |
| | CCGCCAGCUUUGGGUACCCUGACCAAUUCACGGCCAUCCG | 180 |
| | CCGCCCAGCUUUGGGUACCCUGACCAAUUCACGGCCAUCCA | 181 |
| X | GUAAUUGUCUGAGACCACCGGACAAUCAACAAGAAAUCCU | 182 |
| | GUAAUUGUCUGAGACCACCGGACAAUCAACAAGAAAAUCCU | 183 |
| | UAAUUGUCUGAGACCACCGGACAAUCAACAAGAAAUCCU | 184 |
| Y | UCAGGCCAAAGUGUGAUAGCCACACCCGCACCCAUCAGGA | 185 |
| | UCAGGCCAAAGUGUGAUAGCCACACCCGCACCCAUCAGA | 186 |
| | UCAGGCCAAAGUGUGAUAGCCACACCCGCACCCAUCAGG | 187 |
| Z | CCGACCGCCGACCAGGGUGCCACUCGUACCCCUGUCCGCC | 188 |
| | CCGACCGCCGACCAGGGUGCCACUCGUACCCCUGUCCGCCC | 189 |
| | CCGACCGCCGACCAGGGUGCCACUCGUACCCCUGUCCGCC | 190 |
| | CCGACCGCCGACCAGGGUGCCACUCGUACCCCUGUCCGC | 191 |
| AA | UGCCAAGUCGAAGCCCGACCACGCCAUCCCUAACAGUGCC | 192 |
| | UGCCAAAGUCGAAGCCCGACCACGCCAUCCCUAACAGUGCC | 193 |
| | UGCCAAGUCGAAGCCCGACCACGCCAUCCCUAACAGUGC | 194 |
| | UGCCAAGUCGAAGCCCGACCACGCCAUCCCUAACGGUGCC | 195 |
| | UGCCAAGUCGAAGCCCGACCACGCCAUCCCUAACAGUGCA | 196 |
| | UGCCAAGUCGAGGCCCGACCACGCCAUCCCUAACAGUGCC | 197 |
| | UGCCAAGCCGAAGCCCGACCACGCCAUCCCUAACAGUGCC | 198 |
| AB | ACUUGUGCUGAGUCGCCAAAGUGAGGCCCACUCGCCAGCA | 199 |
| | GCUUGUGCUGAGUCGCCAAAGUGAGGCCCACUCGCCAGCA | 200 |
| | ACCUGUGCUGAGUCGCCAAAGUGAGGCCCACUCGCCAGCA | 201 |
| AC | CCGCCAGCUCCUCUGAGGCACAAGAGGUUCACGGUGAUCC | 202 |
| | CCGCCAGCUCCUCUGAGGCACAAGAGGUUCACGGUGAUCCC | 203 |
| AD | CACCAGGUUCUGCUGUCCCCAAGCGCUGACCCAUCCUUCC | 204 |
| | CACCAGGUUCUGCUAUCCCCAAGCGCUGACCCAUCCUUCC | 205 |
| | CACCAGGUUCUGCUGUCUCCAAGCGCUGACCCAUCCUUCC | 206 |
| | CACCAGGUUCUGCUGUUCCCAAGCGCUGACCCAUCCUUCC | 207 |
| | CACCAGGUCCUGCUGUCCCCAAGCGCUGACCCAUCCUUCC | 208 |
| | CACCAGGCUCUGCUGUCCCCAAGCGCUGACCCAUCCUUCC | 209 |
| | CACCAGGUUCUGCUGUCCUCAAGCGCUGACCCAUCCUUCC | 210 |
| AE | AAGAUCCGGUAACUCCCCACCGCAAUCACCGUCGACUACU | 211 |
| | AAGAUCCGGUGACUCCCCACCGCAAUCACCGUCGACUACU | 212 |
| | AAGAUCCGGUAACUCCCUACCGCAAUCACCGUCGACUACU | 213 |
| | AAAGAUCCGGUAACUCCCCACCGCAAUCACCGUCGACUACU | 214 |
| AF | CCAUCUAGAUCUCCGUAGAUUCCCCCGGCUCUUUCUCGC | 215 |
| | CCAUCUAGAUCUCCGUAGAUUCCCCCGGGCUCUUUCUCGU | 216 |
| | CCAUCUAGAUCUCCGUAGAUUCCCCCGGGCUCUUUCUCGA | 217 |
| | CCAUCUAGAUCUCCGUAGAUUCCCCCGGGCUCUUUCUCG | 218 |
| | CCAUCUAGAUCUCCGUAGAUUCCCCCGGGCUCUUUCUCGC | 219 |
| | CCAUCUAGAUCUCCGUAGAUUCCCCCGGGCUCUUUCUCAC | 220 |
| | CCAUCUAGAUCUCCGUAGAUUUCCCCGGCUCUUUCUCGC | 221 |
| | CCAUCUAGAUCUCCGUAGAUUCCCCGGGCUCUUCCUCGC | 222 |
| | CCAUCUAGAUCUCCGUAGAUUCCCCGGGCUCUCUCUCGC | 223 |
| | CCAUCUAGAUCUCCGUAGAUUCCCCCGGGCUCUUUCUUGC | 224 |
| | CCAUCUAGAUCUCCGUAGAUUCCCCGGGCCCUUUCUCGC | 225 |
| | CCAUCUAGAUCUCCGUAGAUUCCCCGGGCUCUUUCUCUC | 226 |
| | CCAUCUAGAUCUCCGUAGAUUCCCCGGCCUCUUUCUCGC | 227 |
| | CCAUCUAGAUCUCCGUAGAUUCCCCGGGCUCUUUCUCCC | 228 |
| | CCAUCUAGAUCUCCGUAGAUUCCCCCGGGCUCUUUCUCGUC | 229 |
| AG | CCAUCUGAACCCACAGAUUCCCCCAUCAUCAGCCACAGUG | 230 |
| | CCAUCUGAACCCACAGAUUCCCCCAUCAUCAGCCACAGUA | 231 |
| | CCAUCUGAACCCACAGAUUCCCCCAUCAUCAGCCACAGCG | 232 |
| | CCAUCUGAACCCACAGAUUCCCCCAUCAUCAGCCACAGUC | 233 |
| | CCAUCUGAACCCACAGAUUCCCCCAUCAUCAGCCACGGUG | 234 |

TABLE 4-continued

Variant Nucleolin Aptamer Sequences without 5' and 3' Constant Regions from All Families

| Family Name | All Family Sequences | SEQ ID NO: |
|---|---|---|
| AH | CACUAAGUUGGUAGCCCCAACUGCCCCGACACGAGGAUGU | 235 |
|  | CACUAAGUUGGUAGCCCCAACUGCCCCGACACGAGGAUGUC | 236 |
|  | CACUAAGUUGGUAGCCCCAACUGCCCCGACACGAGGAUGC | 237 |
| AI | UUGUGCUCCGUGGCUCCCCGGACCAACCGCUUCCAGCAGU | 238 |
|  | UUGUGUUCCGUGGCUCCCCGGACCAACCGCUUCCAGCAGU | 239 |
|  | UUGUGCUCCGUGGCUCCCCGGACCAACCGCUUCCAGCAGC | 240 |
|  | UUGCGCUCCGUGGCUCCCCGGACCAACCGCUUCCAGCAGU | 241 |
| AJ | CAAUCACGCGUAGUACGUCGCGGAAGAUCCCCAUGCCGA | 242 |
|  | CAAUCACGCGUAGUACGUCGCGGAAGAUCCCCAUGCCGG | 243 |
|  | CAAUCACGCGUAGUACGUCGCGGAAGAUCCCCAUGCCAA | 244 |
|  | CAAUCACGCGUAGUACGUCGCGGAAGAUCCCCAUGCCGU | 245 |
|  | CAAUCACGCGUAGCACGUCGCGGAAGAUCCCCAUGCCGA | 246 |
|  | CAAUCACGCGUAGUACGUCGCGGAGGAUCCCCAUGCCGA | 247 |
| AK | CACAUGGUACGCCCAAAAGCGAGGCCCGCUGCGUAGUGC | 248 |
|  | CACAUGGUACGCCCCAAAGCGAGGCCCGCUGCGUAGUGC | 249 |
|  | CACAUGGUACGCCCAAAGCCGAGGCCCGCUGCGUAGUGC | 250 |
|  | CACAUGGUACGCCCAAAAGCGAGGCCCGCUGCGUAGUG | 251 |
| AL | UGCCAUACGCGGUUCGAAGUCGAAGCCCGACAACCCGGCA | 252 |
|  | UGCCAUACGCGGUUCGAAGUCGAAGCCCGACAACCCCGGCA | 253 |
|  | UGCCAUACGCGGUUCGAAGUCGAGGCCCGACAACCCGGCA | 254 |
| AM | GUUAUUCACAUGCCUCCCGUGAAUCAACAAGAAUUCCUUG | 255 |
|  | UUAUUCACAUGCCUCCCGUGAAUCAACAAGAAUUCCUUG | 256 |
|  | GUUAUUCACAUGCCUCCCGUGAAUCAACAAGAAUUCCUCG | 257 |
|  | GUUAUUCACAUGCCUCUCGUGAAUCAACAAGAAUUCCUUG | 258 |
|  |  | 259 |
| AN | AAAGAUCUAGACUGUAAGUCUCCAAUCGCCCAGUUAAUUC | 260 |
|  | AAAAGAUCUAGACUGUAAGUCUCCAAUCGCCCAGUUAAUUC | 261 |
|  | AAAGAUCUAGACUGUAAGUCUCCAAUCGCCCAGUAAUUC | 262 |
| AO | GCCCAAUCGCCAGUGGAACGCGCUGAAGGAUCUGCACCC | 263 |
|  | GCCCAAUCGCCAGUGGAACGCGCUGAAGGAUCUGCACC | 264 |
|  | GCCCAAUCGCCAGUGGAACGCACUGAAGGAUCUGCACCC | 265 |
|  | GCCCAAUCGCCAGUGGAACGCGCUGAAGGAUCUGCACCCC | 266 |
|  | CCCAAUCGCCAGUGGAACGCGCUGAAGGAUCUGCACCC | 267 |
|  | GCCCAAUCGCCAGCGGAACGCGCUGAAGGAUCUGCACCC | 268 |
| AP | UGCAACGUAAAAGAGAGUCAUCUCAGGCUAGUCGUCUACC | 269 |
|  | UGCAACGUAAAAGAGAGUCAUCUCAGGCUAGUCGUCUAC | 270 |
| AQ | GUGUACGCCAAGUCGAGGCCCGACCGUACCCAUACGCGAC | 271 |
|  | UGUACGCCAAGUCGAGGCCCGACCGUACCCAUACGCGAC | 272 |
|  | GUGUACGCCAAGUCGAGGCCCGACCGUACCCAUACGCGGC | 273 |
|  | GUGUACGCCAAGUCGAGGCCCGACCGUACCCAUACGCGAU | 274 |
| AR | UUAGCUCUACUUUCCUCUUCAGUAAGACUAACCGCUUCUU | 275 |
|  | UUAGCUCUACUUUCCUCUUCAGUAAGACUAACCGCUUCCU | 276 |
|  | UUAGCUCUACUUUCCUCUUCAGUAAGACUAACCGCUUCUC | 277 |
|  | UUAGCUCUACUUUCCUCUUCAGUAAGACUAACCGCUCCUU | 278 |
| AS | UCCAAGCGGAGGCCCCGCACCCACCCUCCAACGGGCACGG | 279 |
|  | UCCAAGCGGAGGCCCCGCACCCACCCUCCAACGGGCACGC | 280 |
|  | UCCAAGCGGAGGCCCCGUACCCACCCUCCAACGGGCACGG | 281 |
|  | UCCAAGCGGAGGCCCCGCACCCACCCCCAACGGGCACGG | 282 |
|  | UCCAAGCGGAGGCCCCGCACCCACCCUCCAACGGGCACGA | 283 |
|  | UCCAAAGCGGAGGCCCCGCACCCACCCUCCAACGGGCACGG | 284 |
|  | UCCAAGCGGAGGCCCCGCACCCACCCUCCAACGGGCACAG | 285 |
| AT | UAUCGCUCCACAACGACUCCCGUGGACUACCCAAUUCCAA | 286 |
|  | UAUCGCUCCACAACGACUCCCGUGGACUACCCAAUUCCAG | 287 |
|  | UAUCGCUCCACAACGACUCCCGUGGACUACCCAAUUCCAAA | 288 |
|  | UAUCGCUCCACAACGACUCCCGUGGACUACCCAAUUCCAU | 289 |
| AU | GUCGUGCCCAAGUGAAGGCCUCACGCACGCAUCCUAACCU | 290 |
|  | UCGUGCCCAAGUGAAGGCCUCACGCACGCAUCCUAACCU | 291 |
|  | GCGUGCCCAAGUGAAGGCCUCACGCACGCAUCCUAACCC | 292 |
| AV | AAGAUCUGCGCCAGCACAAUCACCAUCGUCCUGAGAAUGG | 293 |
|  | AAGAUCUGCGCCAGCACAAUCACCAUCGUCCUGAGAAUGC | 294 |

TABLE 4-continued

Variant Nucleolin Aptamer Sequences without 5' and 3' Constant Regions from All Families

| Family Name | All Family Sequences | SEQ ID NO: |
|---|---|---|
| | AAGAUCUGCGCCAGCACAAUCACCAUCGUCCUGAGAAUGA | 295 |
| | AAGAUCUGCGCCAGCACAAUCACCAUCGUCCUGAGAGUGG | 296 |
| | AAGAUCUGCGCCAGCACAAUCACCAUCGUCCUGGGAAUGG | 297 |
| AW | AUGCCAAGCAGUGGCCCUGCCACCCACCUAUCACUGUCGA | 298 |
| | AUGCCAAGCAGUCGGCCUGCCACCCACCUAUCACUGUCGA | 299 |
| | AUGCCAAGCAGUGGCCCUGCCACCCACCUAUCACUAUCGA | 300 |
| | AUGCCAAGCAGUGGCCCUGCCACCCACCUACCACUGUCGA | 301 |
| | AUGCCAAGCAGCGGCCCUGCCACCCACCUAUCACUGUCGA | 302 |
| AX | AACAGACCAAGCAGCGGCCCUGCUCUGCCAUCAUACGCCU | 303 |
| | GACAGACCAAGCAGCGGCCCUGCUCUGCCAUCAUACGCCU | 304 |
| | AACAGACCAAGCAGUGGCCCUGCUCUGCCAUCAUACGCCU | 305 |
| | AACAGACCAAGCAGCGGCCCUGCUCUGCCAUCAUACGCCC | 306 |
| | AACAGACCAAGCAGCGGCCCUGCUCUGCCAUCAUACACCU | 307 |
| | ACAGACCAAGCAGCGGCCCUGCUCUGCCAUCAUACGCCU | 308 |
| | AACAGACCAAGCAGCGGCCCUGCUCUGCCAUCAUACGCCCU | 309 |
| AY | GUCAUUCGCUGACGAAUCAACAUGAAUUCCUAACUGCUGA | 310 |
| | UCAUUCGCUGACGAAUCAACAUGAAUUCCUAACUGCUGA | 311 |
| | GUCAUUCGCUGACGAAUCAACAUGAAUUCCUAACUGCCGA | 312 |
| | GUCAUUCGCUGACGAAUCAACAUGAAUUCCUAACUGCUGG | 313 |
| AZ | ACACGCCAAGCUGGUAGCCCCAGCCGUGCCCAUUACGGCC | 314 |
| | ACACGCCAAGCUGGUAGCCCCAGCCGUGCCCAUUACGGC | 315 |
| | ACACGCCAAGCUGGUAGCCCCAGCCGUGCCCAUUACGGUC | 316 |
| | ACACGCCAAGCUGGUAGCCCCAGCCGUACCCAUUACGGCC | 317 |
| BA | UAGCCAAGCAGCAGCCCUGCCAACCCAUCCUACCCGGGCG | 318 |
| | UAGCCAAGCAGCAGCCCUGCCAACCCAUCCUACCCGGCG | 319 |
| | UAGCCAAGCAGCAGCCCUGCCAACCCAUCCUACCCGGGCA | 320 |
| | UAGCCAAGCAGCAGCCCUGCCAACCCAUCCUACCCGGGUG | 321 |
| | UAGCCAAGCAGCGGCCCUGCCAACCCAUCCUACCCGGGCG | 322 |
| BB | GCCCAAGGCGAGGCCCGCCGCUCCAUCCAGACGCUGAGGG | 323 |
| | GCCAAGGCGAGGCCCGCCGCUCCAUCCAGACGCUGAGG | 324 |
| | CCCAAGGCGAGGCCCGCCGCUCCAUCCAGACGCUGAGGG | 325 |
| | CCCAAGGCGAGGCCCGCCGCUCCAUCCAGACGCUGAGG | 326 |
| | GCCCAAGGCGAGGCCCGCCGCUCCAUCCAGACGCUGAGGC | 327 |
| | GCCCAAAGGCGAGGCCCGCCGCUCCAUCCAGACGCUGAGGG | 328 |
| | GCCCAAGGCGAGGCCCGCCGCUCCAUCCAGACGCUGAGGA | 329 |
| | GCCCCAAGGCGAGGCCCGCCGCUCCAUCCAGACGCUGAGGG | 330 |
| BC | AAGAUCUCGUCAUGCUUUGACGUCAAUCACCAUUGUUCCC | 331 |
| | AAGAUCUCGUCAUGCUUUGACGUCAAUCACCAUUGUUCC | 332 |
| | AAGAUCUCGUCAUGCUUUGACGCCAAUCACCAUUGUUCCC | 333 |
| | AAGAUCUCGUCAUGCUUUGACGUCAAUCACCAUUGUUCCA | 334 |
| | AAGAUCUCGUCAUGCUUUGACGUCAAUCACCAUUGUUCCU | 335 |
| | AAGAUCUCGUCAUGCUUUGACGUCAAUCACCAUUGUUCCCC | 336 |
| | AAAGAUCUCGUCAUGCUUUGACGUCAAUCACCAUUGUUCCC | 337 |
| | AAGAUCUCGUCAUGCCUUGACGUCAAUCACCAUUGUUCCC | 338 |
| BD | AUCCCCCAGGAUGAGCACGUUGCCAUGGACUGGCUAUCC | 339 |
| | AUCCCCAGGAUGAGCACGUUGCCAUGGACUGGCUAUCC | 340 |
| BE | CUGUUACAGUCUCGCGUAACCCCCCAUCGAUGUCCUCGA | 341 |
| | CUGUUACAGUCUCGCGUAACCCCCCAUCGAUGUCCUCGG | 342 |
| | CUGUUACAGUCUCGAGUAACCCCCCAUCGAUGUCCUCGA | 343 |
| | CUGUUACAGUCUCGCGUAACCCCUCCAUCGAUGUCCUCGA | 344 |
| | CUGUUACAGCCUCGCGUAACCCCCCAUCGAUGUCCUCGA | 345 |
| | CUGUUACAGUCUCCCGUAACCCCCCAUCGAUGUCCUCGA | 346 |
| BF | AGCCAGCUUUCGGCAAACCGAAUUCACUCCACCCUGCUCA | 347 |
| | AGCCAGCUUUCGGCAAACCGAAUUCACUCCACCCUCCUCA | 348 |
| | AGCCAGCUUUCGGCAAACCGAAUUCACUCCGCCCUGCUCA | 349 |
| | AGCCAGCUUUCGGCAAACCGAAUUCACUCCACCCUGCU | 350 |
| | AGCCAGCUUUCGGCGAAACCGAAUUCACUCCACCCUGCUCA | 351 |
| | AGCCAGCUUUCGGCAAACCGAAUUCACUCCACCCUGCUCG | 352 |
| | AGCCAGCUUUCGGCAAACCGAAUUCACUCCACCCUGCUC | 353 |
| | AGCCAGCUUUCGGCAAACCGAAUUCACUCCACCCUGCACA | 354 |
| BG | CACGGUAUAACCUCCUCAUAUACCUGCUGUGCCACCCGCG | 355 |
| | CACGGUAUAACCUCCUCAUAUACCUGCUGUGCCACCCGCA | 356 |
| | CACGGUAUAACCUCCUCAUAUACCUGCUGUGCCACCCACCG | 357 |

TABLE 4-continued

Variant Nucleolin Aptamer Sequences without 5' and 3' Constant Regions from All Families

| Family Name | All Family Sequences | SEQ ID NO: |
|---|---|---|
| | CACGGUAUAACCUCCUCAUAUACCUGCUGUGCCACCCGCU | 358 |
| | CACGGUAUAACCUCCUCAUAUACCUGCUGUGCCACCCACG | 359 |
| | CACGGUAUAACCUCCUCAUAUACCUGCUGUGCCACCCGUG | 360 |
| | CACGGUAUAACCUCCUCAUAUACCUGCUGUGCCGCCCGCG | 361 |
| BH | CCGGAAGAUCUGCUCGCACUAGCCGGAGCCCAAUCACGGC | 362 |
| | CCGGAAGAUCUGCUCGCACUAGUCGGAGCCCAAUCACGGC | 363 |
| | CCGGAGGAUCUGCUCGCACUAGCCGGAGCCCAAUCACGGC | 364 |
| | CCGGAAGAUCUGCUCGCAUUAGCCGGAGCCCAAUCACGGC | 365 |
| BI | CCUGCCGAACGGCUAAGUCGCAGCCCGACCCGCGGCAGGG | 366 |
| | CCUGCCGAACGGCUAAGUCGCAGCCCGACCCGCGGCAGG | 367 |
| | CCUGCCGAACGGCUAAGUCGCAGCCCGACCCGCGGCAGGA | 368 |
| | CCUGCCGAACGGCCAAGUCGCAGCCCGACCCGCGGCAGGG | 369 |
| | CCUGCCGAACGGCUAAGUCGCGGCCCGACCCGCGGCAGGG | 370 |
| BJ | CUCCGACCCGCGGACGAAGUCAACUUCCACAGUCCCACAC | 371 |
| | CUCCGACCCGCGGACGAAGUCAACUUCCACAGUCCCACAA | 372 |
| | CUCCGACCCGCGGACGAAGUCAACUUCCACAGUCCCACACAC | 373 |
| | CUCCGACCCGCGGACGAAGUCAACUUCCACAGUCUCACAC | 374 |
| | CUCCGACCCGCGGACGAAGUCAACUUCCACAGUCCCACAU | 375 |
| | CUCCGACCCGCGGACGAAGUCAACUUCCACAGUCCCGCAC | 376 |
| | CUCCGACCCGCGGACGAAGUCAACUUCCACGGUCCCACAC | 377 |
| | CUCCGACCCGCGGACGAAGUCAACUUCCACAGUCCCAUAC | 378 |
| BK | ACAUUAGGAUCUGCGUGAUGGGGAUCACCCGCUACAUGUC | 379 |
| | ACAUUUAGGAUCUGCGUGAUGGGGAUCACCCGCUACAUGUC | 380 |
| | GCAUUAGGAUCUGCGUGAUGGGGAUCACCCGCUACAUGUC | 381 |
| | ACAUUAGGAUCUGCGCGAUGGGGAUCACCCGCUACAUGUC | 382 |
| BL | UCUAAGAUGGGGAAGAUCUCCGGAGCACCGGGCAAUCACC | 383 |
| | UCUAAGAUGGGGAAGAUCUCCGGAGCACCGGGCAAUCACCC | 384 |
| | CCUAAGAUGGGGAAGAUCUCCGGAGCACCGGGCAAUCACC | 385 |
| | UCUAAGGUGGGGAAGAUCUCCGGAGCACCGGGCAAUCACC | 386 |
| | UCUAAGAUGGGGAAGAUCUCCGGAGCGCCGGGCAAUCACC | 387 |
| BM | CUAUUCGAGUUCCCACGAAUCCCCCAUCGAGAACCUAC | 388 |
| | CUAUUCGAGUUCCCACGAAUCCCCCAUCAGAACCUAC | 389 |
| | CUACUCGAGUUCCCACGAAUCCCCCAUCGAGAACCUAC | 390 |
| | CUAUUCGAGUUCCCACGAAUCCCCCAUCAAGAACCUAC | 391 |
| BN | UGCCAAGCCGAGGCCCGGCCAGCAUCCCUCACGAGAGAGG | 392 |
| | UGCCAAAGCCGAGGCCCGGCCAGCAUCCCUCACGAGAGAGG | 393 |
| | UGCCAAGCCGAGGCCCGGCCAGCAUCCCUCACGAGAGAGC | 394 |
| | UGCCAAGCCGAGGCCCGGCCAGCAUCCCUCACGAGAGAG | 395 |
| | UGCCAAGCCGAGGCCCGGCCAGCAUCCCCCACGAGAGAGG | 396 |
| | UGCCAAGCCGAGGCCCGGCCAGCAUCCCUCACGAGAGAGA | 397 |
| | UGCCAAGCCGGGGCCCGGCCAGCAUCCCUCACGAGAGAGG | 398 |
| | UGCCAAGCCGAGGCCCGGCCAGCAUCCCUCACGAGAGGG | 399 |
| BO | GCCAAGCACGUAGCCCGUGCCCCCACCCGCCUGUGUGCUG | 400 |
| | CCAAGCACGUAGCCCGUGCCCCCACCCGCCUGUGUGCUG | 401 |
| | GCCAAGCACGUAGCCCGUGCCCCCACCCGCCUGUGUGCGG | 402 |
| | GCCAAGCACGUAGCCCGUGCCCCCACCCACCUGUGUGCUG | 403 |
| | GCCAAGCACGUAGCCCGUGCCCCCACCCGCCUGUGUGCUC | 404 |
| | GCCAAGCACGUAGCCCGUGCCCCCACCCGCCUGUGUGCCG | 405 |
| | GCCAAGCACGUAGCCCGUGCCCCCACCCGCCUGUGUGCUG | 406 |
| | GCCAAGCACGUAGCCCGUGCCCCCACCCGCCUGUGUGCUA | 407 |
| BP | UGCCAAGCACGAAGCCCGUGCCCCCAUCCAGAGUGUGAGA | 408 |
| | UGCCAAAGCACGAAGCCCGUGCCCCCAUCCAGAGUGUGAGA | 409 |
| | UGCCAAGCACGAAGCCCGUGCCCCCAUCCAGAGUGUGGGA | 410 |
| | UGCCAAGCACGAGGCCCGUGCCCCCAUCCAGAGUGUGAGA | 411 |
| | UGCCAAGCACGAAGCCCGUGCCCCCAUUCAGAGUGUGAGA | 412 |
| | UGCCAAGCACGAAGCCCGUGCCCCCAUCCAGAGUGCGAGA | 413 |
| | UGCCAAGCACGAAGCCCGUGCCCCCAUCCAGAGCGUGAGA | 414 |
| | UGCCAAGCACGAAGCCCGUGCCCCCAUCCAGAGUGUGAGG | 415 |
| | UGCCAAGCACGAAGCCCGUGCCCCCAUCCAGGGUGUGAGA | 416 |

TABLE 4-continued

Variant Nucleolin Aptamer Sequences without 5' and 3' Constant Regions from All Families

| Family Name | All Family Sequences | SEQ ID NO: |
|---|---|---|
| BQ | AGCCAGCUUUUGCAUACCACGUGCAAUUCACUCCACCCGUCA | 417 |
|  | AGCCAGCUUUGCCAUACCACGUGCAAUUCACUCCACCCGUCA | 418 |
|  | AGCCAGCCUUUGCAUACCACGUGCAAUUCACUCCACCCGUCA | 419 |
|  | AGCCAGCUUUUGCAUACCACGUGCAAUUCACUCCACCCGUCG | 420 |
|  | AGCCAGCUUUUGCACACCACGUGCAAUUCACUCCACCCGUCA | 421 |
|  | AGCCAAGCUUUGCAUACCACGUGCAAUUCACUCCACCCGUCA | 422 |
| BR | CUUUGUAAACCCGGCAAACAAAAUCAACUUCCAUCAUCAA | 423 |
|  | CUUUGUAAACCCGGCAAACAAAAUCAACUUCCAUCACCAA | 424 |
| BS | CCAUUGUAGCGACCACACAAUUCCCCAUCGGACAGCAUGG | 425 |
|  | CCAUUGUAGCGACCACACAAUUCCCCAUCGGACAGCAUG | 426 |
|  | CCAUUGUAGCGACCACACAAUUCCCCAUCGGACAGCGUGG | 427 |
|  | CCAUUGUAGCGACCACACAAUUCCCCAUCGGACAGCACGG | 428 |
|  | CCAUUGUAGCGACCACACAAUUCCCCAUCGGACAGCAUGC | 429 |
|  | CCAUUGUAGCGACCACACAAUCCCCCAUCGGACAGCAUGG | 430 |
|  | CCAUUGUAGCGACCACACAAUUCCCCAUCGGACAGCAUGU | 431 |
| BT | CUCUCGCCGUUCCCAGGCACGACAAAAUCAACUUCCCGCU | 432 |
|  | CUCUCGCCGUUCCCAGGCGCGACAAAAUCAACUUCCCGCU | 433 |
|  | CUCUCGCCGUUCCCGGGCACGACAAAAUCAACUUCCCGCU | 434 |
|  | CUCUCGCCGUUCCCAGGCACGACAAAAUCAACUUCCCGCA | 435 |
| BU | AAGCCAAGCCGCGGCCCGGCCUUCCCAUGUGCUACUAGAG | 436 |
|  | AAAGCCAAGCCGCGGCCCGGCCUUCCCAUGUGCUACUAGAG | 437 |
|  | AAGCCAAAGCCGCGGCCCGGCCUUCCCAUGUGCUACUAGAG | 438 |
|  | GAGCCAAGCCGCGGCCCGGCCUUCCCAUGUGCUACUAGAG | 439 |
|  | AGCCAAGCCGCGGCCCGGCCUUCCCAUGUGCUACUAGAG | 440 |
|  | AAGCCAAGCCGUGGCCCGGCCUUCCCAUGUGCUACUAGAG | 441 |
|  | UGCCAAGCCGCGGCCCGGCCUUCCCAUGUGCUACUAGAG | 442 |
|  | AAGCCAAGCCGAGGCCCGGCCUUCCCAUGUGCUACUAGAG | 443 |
| BV | CCAAAUGCCAAAGCCGUAGCCCGGCCAGUAGCCCACACGUC | 444 |
|  | CCAAAAUGCCAAAGCCGUAGCCCGGCCAGUAGCCCACACGUC | 445 |
|  | CCAAAUGCCAAGCCCGUAGCCCGGCCAGUAGCCCACACGUC | 446 |
| BW | CCAUUACGCGACGUAAUUCCCCCAUCGUUUCCUCGUUAAG | 447 |
|  | CCAUUACGCGACGUAAUUCCCCCAUCGUCUCCUCGUUAAG | 448 |
|  | CCAUUACGCGACGUAAUUCCCCCAUCGCUUCCUCGUUAAG | 449 |
|  | CCAUUACGCGGCGUAAUUCCCCCAUCGUUUCCUCGUUAAG | 450 |
|  | CCAUUACGCGACGUAAUUCCCCCAUCGUUUCCUCGUUAGG | 451 |
|  | CCAUUACGCGACGUAAUUCCCCCAUCGUUUCCUCGCUAAG | 452 |
|  | CCAUUACGCGACGUAAUUCCCCCAUCGUUUCCUCGUUAUG | 453 |
|  | CCAUUACGCGACGUAAUUCCCCCAUCGUUUCCUCGUUAAA | 454 |
| BX | CCAUCUAGAUCUCCGUAGAUUCCCCGGCUCUUUCUCGC | 455 |
|  | CCAUCUAGAUCUCCGUAGAUUCCCCAGCUCUUUCUCGC | 456 |
|  | CCAUCUAGAUCUCCGUAGAUCCCCCGGCUCUUUCUCGC | 457 |
|  | CCAUCUAGAUCUCCGUAGAUUCCCCGCUCUUUCUCGC | 458 |
|  | CCAUCUAGAUCUCCGUAGAUUCCCCGGCUCUUCCUCGC | 459 |
|  | CCAUCUAGAUCUCCGUGAUUCCCCGGCUCUUUCUCGC | 460 |
|  | CCAUCUAGAUCUCCGUAGUUCCCCGGCUCUUUCUCGC | 461 |
|  | CCAUCUAGAUCCCGUAGAUUCCCCGGCUCUUUCUCGC | 462 |
|  | CCAUCUAGAUCUCCGUAGAUUCCCCGGCUCCUUCUCGC | 463 |
|  | CCAUCUAUAUCUCCGUAGAUUCCCCGGCUCUUUCUCGC | 464 |
| BY | ACUGUCUGCAUACACGGUAUGCCCAACGCCAUCCAAACCG | 465 |
|  | ACUGUCUGCAUACACGGUAUGCCCAACGCCAUCCAAACCGC | 466 |
|  | ACUGUCUGCAUACAUGGUAUGCCCAACGCCAUCCAAACCG | 467 |
|  | ACUGUCUGCAUACACGGUAUGCCCAACGCCAUCCAAAACCG | 468 |
| BZ | ACCUGCGGCUAUUGCCAGCGCCAUAAGACCCUCCACAGUA | 469 |
|  | ACCUGCGGCUAUUGCCAGCGCCAUAAGACCCUCCACAGCA | 470 |
|  | CCUGCGGCUAUUGCCAGCGCCAUAAGACCCUCCACAGUA | 471 |
|  | ACCUGCGGCUAUUGCCAGCGCCAUAAGACCUUCCACAGUA | 472 |
|  | ACCUGCGGCUAUUGCCAGCGCCAUAAGACCCUCCGCAGUA | 473 |

TABLE 5

Nucleolin Binding of Aptamer Families A-F

| Clone | Kd (nM) | Bmax (%) | $R^2$ |
|---|---|---|---|
| FAM-A | 10.07 | 17.66 | 0.9499 |
| FAM-B | 0.8508 | 25.2 | 0.8335 |
| FAM-C | 0.4285 | 32.76 | 0.869 |
| FAM-D | 0.586 | 53.6 | 0.9447 |
| FAM-E | 1.69 | 23.08 | 0.7941 |
| FAM-F | 0.37 | 33.6 | 0.6520 |

TABLE 6

Nucleolin Aptamer Truncates

| NCL Aptamer | Sequence |
|---|---|
| Bv1 | GGAAGAGGGAUGGGUGCCAGCUUUGCAUACCACGUGCAAUUCACUCCACCCGUCAC (SEQ ID NO: 474) |
| Bv2 | GGGAGAGAGGAAGAGGGAUGGGAGCCAGCUUUGCAUACCACGUGCAAUUCACUCCACCCGUCAC (SEQ ID NO: 475) |
| Dv1 | GGGAUGGGCACAUGGUACGCCCAAAGCGAGGCCCGCUGCGUAGUGCCAUAACCCAG (SEQ ID NO: 476) |
| Dv2 | GGGAGAGAGGAAGAGGGAUGGGCACAUGGUACGCCCAAAGCGAGGCCCGCUGCGUAGUGCC (SEQ ID NO: 477) |
| Ev1 | GGGAUGGGCACGGUCCAGCGCUAACUGUACCUGCUGUGCCACCCACCGCAUAACCCAGAGGUCGAU (SEQ ID NO: 478) |
| Ev2 | GGGAUGGGCACGGUCCAGCGCUAACUGUACCUGCUGUGCCACCCACCGC (SEQ ID NO: 479) |
| Ev3 | GGGAGAGAGGAAGAGGGAUGGGCACGGUCCAGCGCUAACUGUACCUGCUGUGCCACCCACCG (SEQ ID NO: 480) |
| Ev4 | GGGAGAGAGGAAGAGGGAUGGGCACGGUCCAGCGCUAACUGUACC (SEQ ID NO: 481) |
| Ev5 | GGAAGAGGGAUGGGCACGGUCCAGCGCUAACUGUACCUGCUGUGCCACCCACC (SEQ ID NO: 482) |
| Fv1 | GGGACCACGCGCCAACGUGUCAGCUACACGCCGUGUUCCCCGG (SEQ ID NO: 483) |
| Fv2 | GGGACCACGCGCCAACGUGUCAGCUACACGCCGUGUUCCCCGGCAUAACCCAGAGGUCGAU (SEQ ID NO: 484) |
| Fv3 | GGGAGAGAGGAAGAGGGAUGGGACCACGCGCCAACGUGUCAGCUACACGCCGUGUUCCCCGG (SEQ ID NO: 485) |

TABLE 7

Ev3 Truncates

| NCL Aptamer | Sequence |
|---|---|
| Ev3.min21 | GGGAUGGGCACGGUCCAGCGCUAACUGUACCUGCUGUGCCACCC (SEQ ID NO: 486) |
| Ev3.min22 | GGGAGGAAGAGGGAUGGGCACGGUCCAGCGCUAACUGUACCUGCUGUGCCACCC (SEQ ID NO: 487) |
| Ev3.min23 | GGGAGGAAGAGGAUGGGCACGGUCCAGCGCUAACUGUACCUGCUGUGCCACC (SEQ ID NO: 488) |
| Ev3.min24 | GGGAGGAAGAGGGAUGGGCACGGUCCAGCGCACUGUACCUGCUGUGCCACCC (SEQ ID NO: 489) |
| Ev3.min25 | GGGAGGAAGAGGAUGGGCACGGUCCAGCGCACUGUACCUGCUGUGCCACC (SEQ ID NO: 490) |

TABLE 8

Additional Nucleolin Aptamers

| NCL Aptamer | Sequence |
|---|---|
| Cv1 | GGGAUGGGAAGAUCUGCUAAGUGCACGCACAAUCACCAUCGAGCGUCUC (SEQ ID NO: 494) |
| Cv2 | GGGAGAGAGGAAGAGGGAUGGGAAGAUCUGCUAAGUGCACGCACAAUCACCAUCGAGCGUCUC (SEQ ID NO: 495) |
| Ev6 | GGGAGAGAGGAAGAGGGAUGGGCACGGUCCAGCGCUAACUGUACCUGCUGUGCC (SEQ ID NO: 496) |
| Ev3min2 | GGGAGAGAGAGGGAUGGGCACGGUCCAGCGCUAACUGUACCUGCUGUGCCACCCACCG (SEQ ID NO: 497) |
| Ev3min3 | GGGAGAGAGGAAGAGGAUGGGCACGGUCCAGCGCUAACUGUACCUGCUGUGCCACCACCG (SEQ ID NO: 498) |
| Ev3min4 | GGGAGAGAGGAAGAGGGAGGGCACGGUCCAGCGCUAACUGUACCUGCUGUGCCCCACCG (SEQ ID NO: 499) |
| Ev3min5 | GGGAGAGAGGAAGAGGGAUGGGUCCAGCGCUAACUGUACCUGCCACCCACCG (SEQ ID NO: 500) |
| Ev3min6 | GGGAGAGAGGAAGAGGGAUGGGCGGUCCAGCGCUAACUGUACCUGCUGCCACCCACCG (SEQ ID NO: 501) |
| Ev3min7 | GGGAGAGAGGAAGAGGGAUGGGCACGGUCCAGCGCUAUGUCUGCUGUGCCACCCACCG (SEQ ID NO: 502) |
| Ev3min8 | GGGAGAGAGGAAGAGGGAUGGGCACGGUCCAGCGCUAACUGUACCUGCUGUGCCACCC (SEQ ID NO: 503) |
| Ev3min9 | GGGAGGAAGAGGGAUGGGCACGGUCCAGCGCUAACUGUACCUGCUGUGCCACCCACCG (SEQ ID NO: 504) |
| Ev3min10 | GGAAGAGGGAUGGGCACGGUCCAGCGCUAACUGUACCUGCUGUGCCACCCACCG (SEQ ID NO: 505) |
| Ev3min11 | GAGAGGAAGAGGGAUGGGCACGGUCCAGCGCUAACUGUACCUGCUGUGCCACCCACCG (SEQ ID NO: 506) |
| Ev3min12 | GGGAGAGAGGAAGAGGGAUGGGCACGGUCCAGCGCUAACUGUACCUGCUGUGCCACCCAC (SEQ ID NO: 507) |
| Ev3min13 | GGGAGAGAGGAAGAGGGAUGGGCACGGUCCAGCGCUAACUGUACCUGCUGUGCCACCCCG (SEQ ID NO: 508) |
| Ev3min14 | GGGAGAGAGGAAGAGGGAUGGGCACGGUCCGCGCUAACUGUACCUGCUGGCCACCCACCG (SEQ ID NO: 509) |
| Ev3min15 | GGGAGAGAGGAAGAGGGAUGGGCACGGUCCGCGCUAACUGUACCGCUGUGCCACCCACCG (SEQ ID NO: 510) |
| Ev3min16 | GGGAGAGAGGAAGAGGGAUGGGCACGGUCCAGCGCACUGUACCGCUGUGCCACCCACCG (SEQ ID NO: 511) |
| Ev3min17 | GGGAGAGAGGAAGAGGGAUGGGCACGGUCCAGCGCUAACUGUACCUGCUGUGCCACCCACCG (SEQ ID NO: 512) |
| Ev3min18 | GGGAGAGGAAGAGGGAUGGGCACGGUCCAGCGCUAACUGUACCUGCUGUGCCACCCACCG (SEQ ID NO: 513) |
| Ev3min19 | GGGAGAGGAAGAGGGAUGGGCACGGUCCAGCGCUAACUGUACCUGCUGUGCCACCCACCG (SEQ ID NO: 514) |
| Ev3min20 | GAGGAAGAGGGAUGGGCACGGUCCAGCGCUAACUGUACCUGCUGUGCCACCCACCG (SEQ ID NO: 515) |

Example 2—Sensitizing Cancer Cells with Nucleolin Aptamers

Figure 6B:
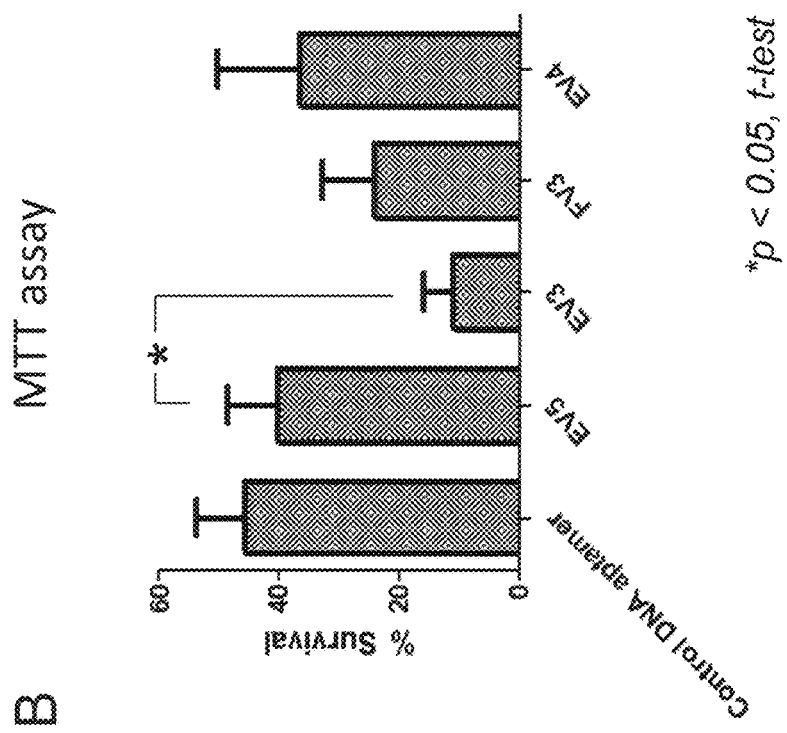
FIGS. 6A-6B show nucleolin specific RNA aptamer EV3 sensitizes colon cancer cells to ionizing radiation. HCT 116 p53-/- colon cancer cells were treated with 5 μg of indicated aptamers and exposed to 2Gy IR 48 h later. Cells were cultivated for 10d and survival was assessed by MTT assay.
Figure 6A:
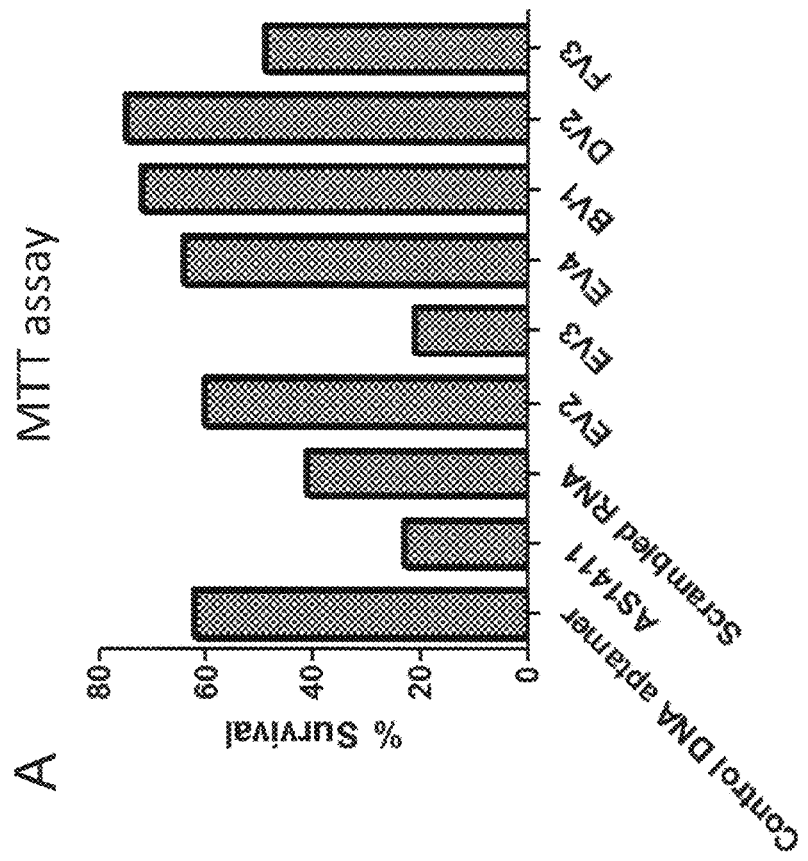

We next tested the ability of the nucleolin aptamer truncates Bv1, Ev3, Ev4, Dv2, and Fv3 to sensitize cancer cells that overexpress nucleolin on the cell surface to ionizing radiation (IR). We also included the Ev2 aptamer as a non-binding aptamer control. As shown in FIG. 6A, Ev3 appears to be a potent radiosensitizer, significantly decreasing post-IR survival in HCT116 p53-null cells. Further radiation sensitization studies showed that Ev3 decreased post-IR survival by approximately 5-fold in HCT116 p53-null cells compared to the aptamer control Ev5, which was used as a control due to its ability to bind nucleolin protein yet lack of radiosensitizing properties (FIG. 6B). Given that a large number of tumors lack functional p53, which is associated with resistance to therapy, it is encouraging that the specific nucleolin aptamer Ev3 can efficiently sensitize p53-null cells to IR.

Figure 7:
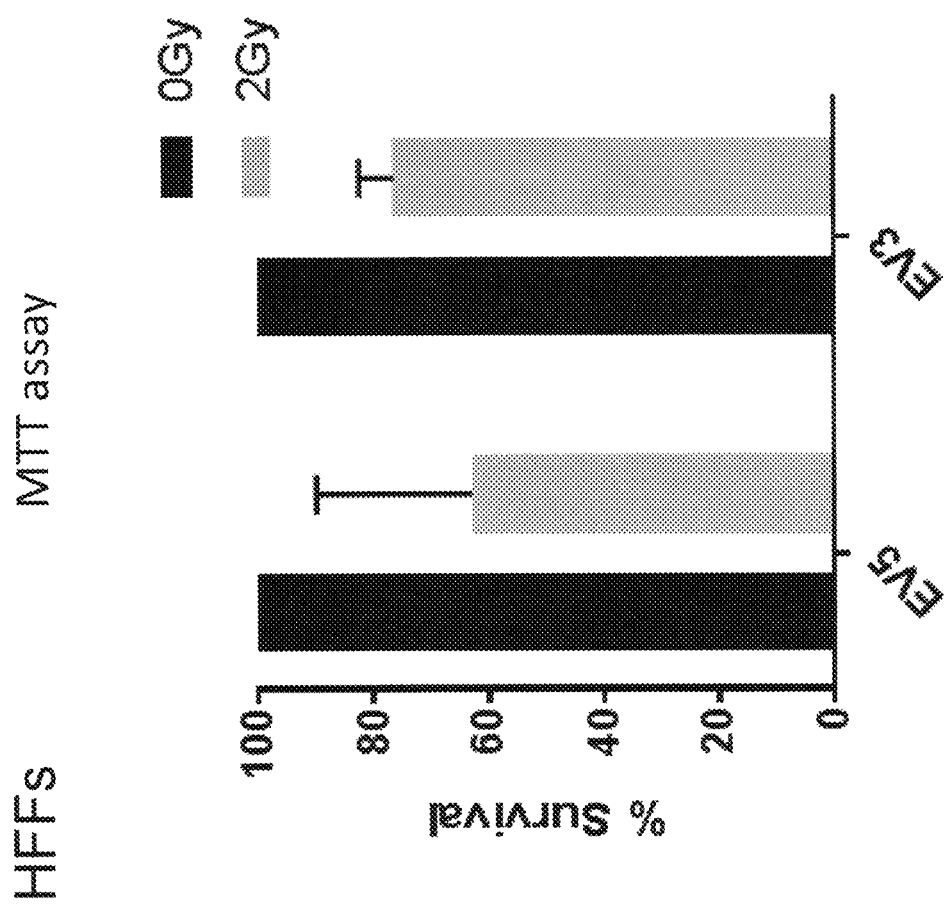
FIG. 7 shows EV3 does not sensitize HFF (human foreskin fibroblasts), that do not express nucleolin on cell surface, to radiation. hTERT-immortalized HFF cells that do not express nucleolin on cell surface were treated with 5 μg of indicated aptamers and exposed to 2Gy IR 48 h later. Cells were cultivated for 10d and survival was assessed by MTT assay.

To determine whether the Ev3 aptamer's ability to sensitize cancer cells to ionizing radiation was specific to the nucleolin protein, we tested the aptamer on hTERT-immortalized HFF cells (FIG. 7). hTERT-immortalized HFF cells that do not express nucleolin on cell surface were treated with 5 μg of indicated aptamers and exposed to 2Gy IR 48h later. Cells were cultivated for 10d and survival was assessed by MTT assay. As seen in FIG. 7, Ev3 does not sensitize HFF (human foreskin fibroblasts) that do not express nucleolin on cell surface to radiation.

Figure 8:
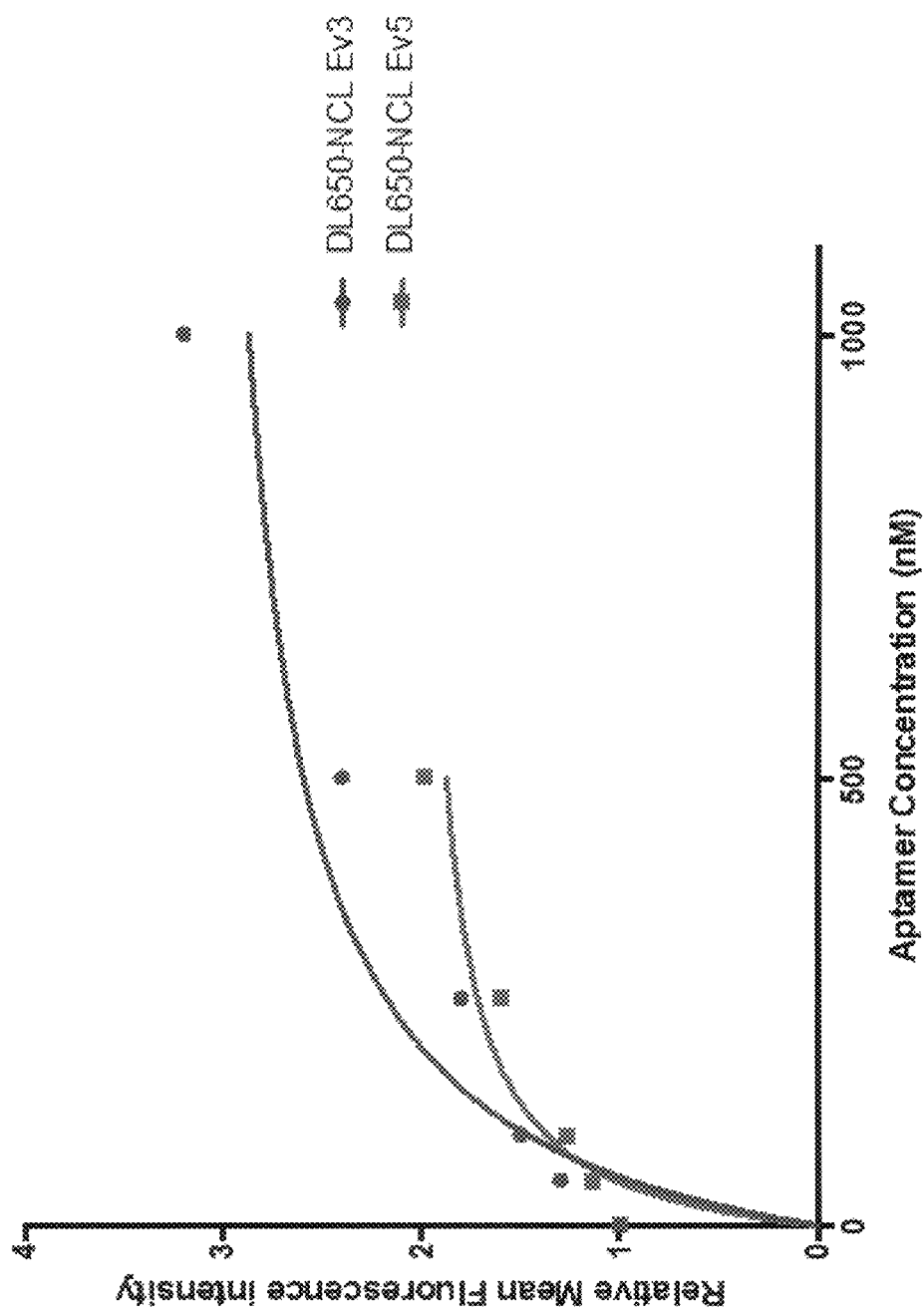
FIG. 8 shows EV3 and EV5 bind to nucleolin expressed on the cell surface in a concentration dependent manner. Flow cytometry analysis of MFI (mean fluorescence intensity) of DL650-labeled EV3 and EV5 after incubation of HCT116 p53-/- cells with the indicated aptamer concentrations.

To determine the Ev3 and Ev5 aptamers could bind nucleolin expressed on a cell surface in a concentration-dependent manner, we performed a flow cytometry analysis with HCT116 p53−/− cells. Flow cytometry analysis of MFI (mean fluorescence intensity) of DL650-labeled Ev3 and Ev5 after incubation of HCT116 p53−/− cells with indicated aptamer concentrations. As shown in FIG. 8 and Table 9, Ev3 and Ev5 bind to nucleolin expressed on the cell surface in a concentration dependent manner.

TABLE 9

| Ev3 and Ev5 Binding Data | | |
|---|---|---|
| One site binding (hyperbola) Best-fit values | DL650-NCL Ev3 | DL650-NCL Ev5 |
| Bmax | 3.214 | 2.064 |
| Kd | 119.2 | 50.7 |

Figure 10:
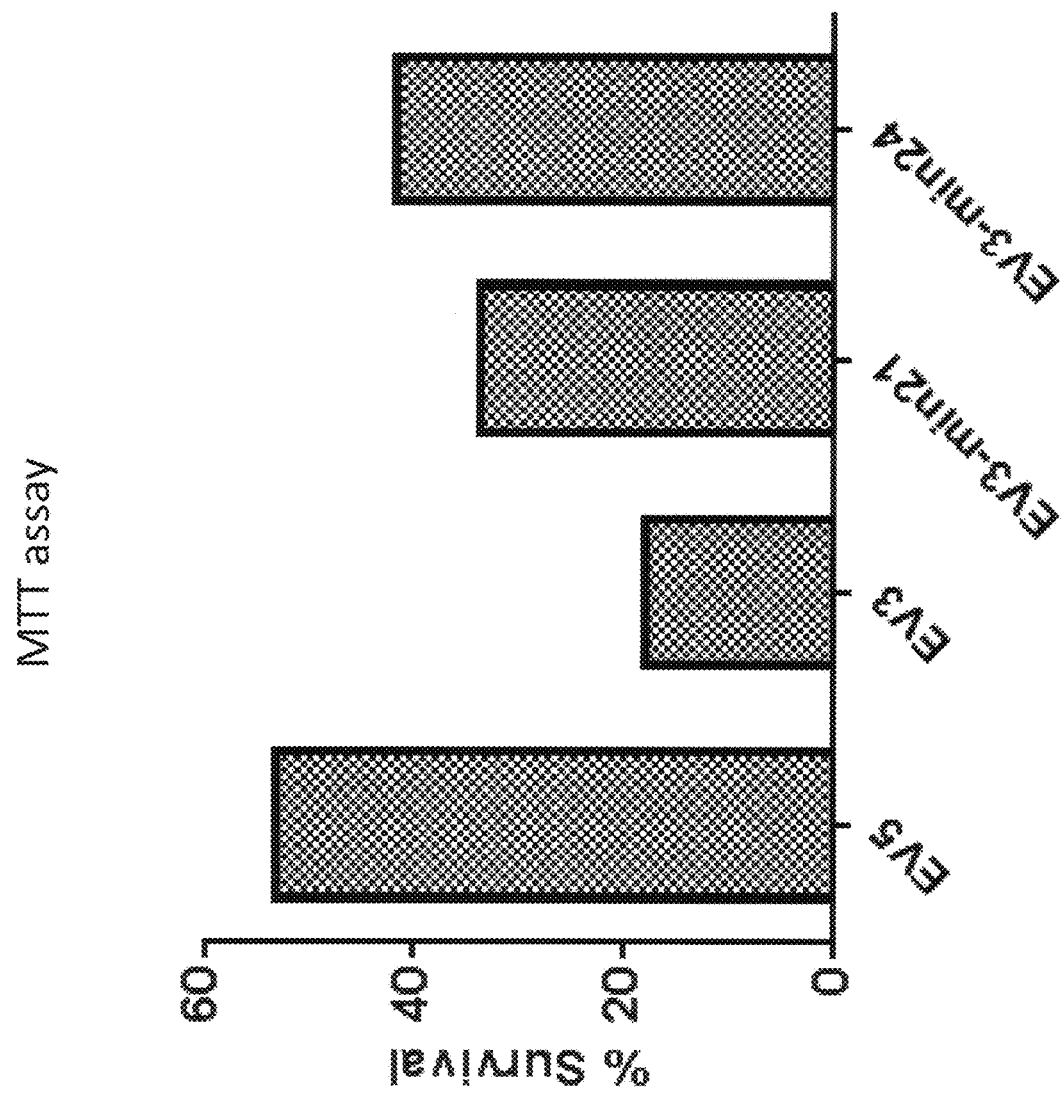
FIG. 10 shows truncation of EV3 resulted in reduced activity as radiosensitizer. HCT 116 p53-/- colon cancer cells were treated with 5 ng of indicated full-length aptamers or EV3 truncates and exposed to 2Gy IR 48h later. Cells were cultivated for 10d and survival was assessed by MTT assay.
Figure 11B:
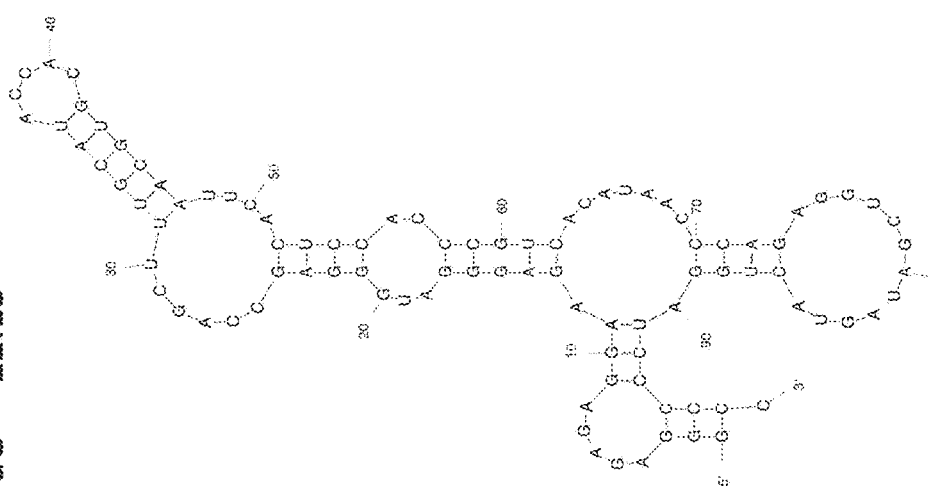
Figure 12A:
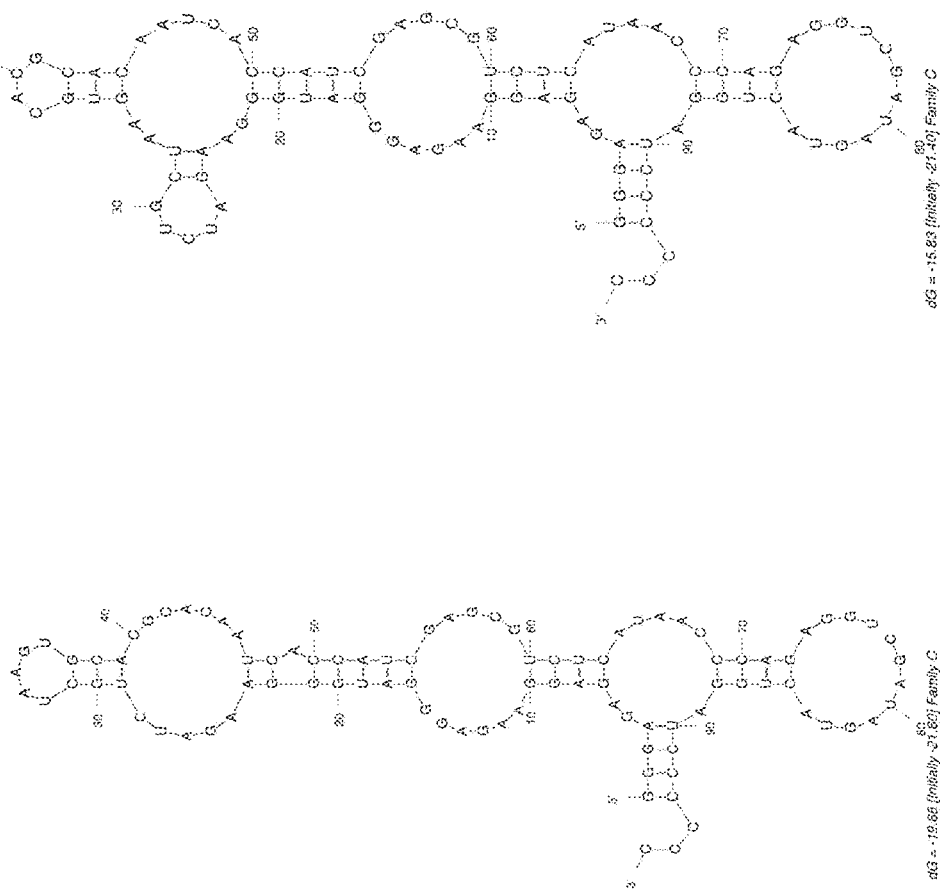
FIGS. 12A-12B show predicted secondary structures for a representative Family C aptamer (SEQ ID NO: 9).
Figure 12B:
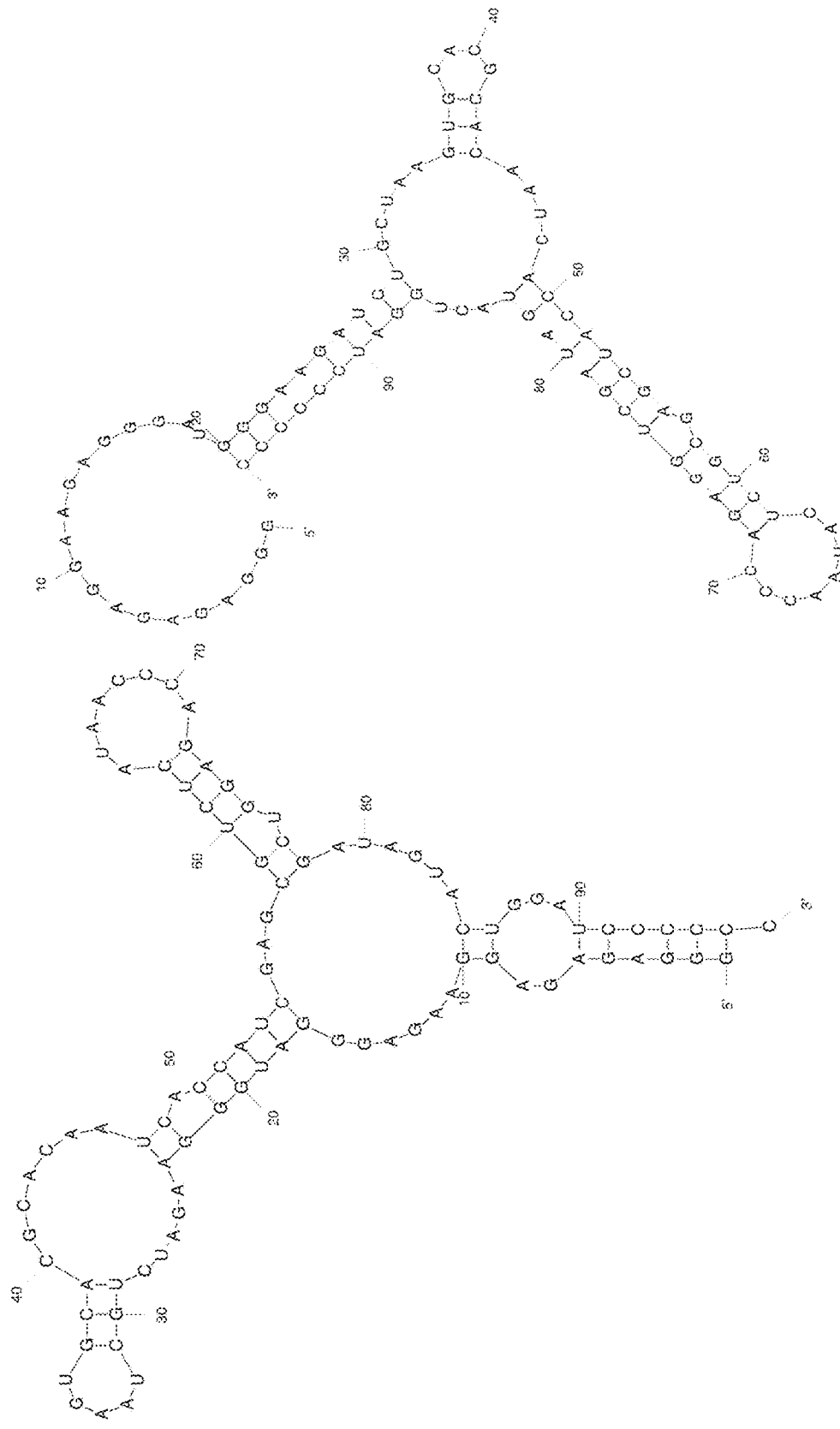
Figure 13C:
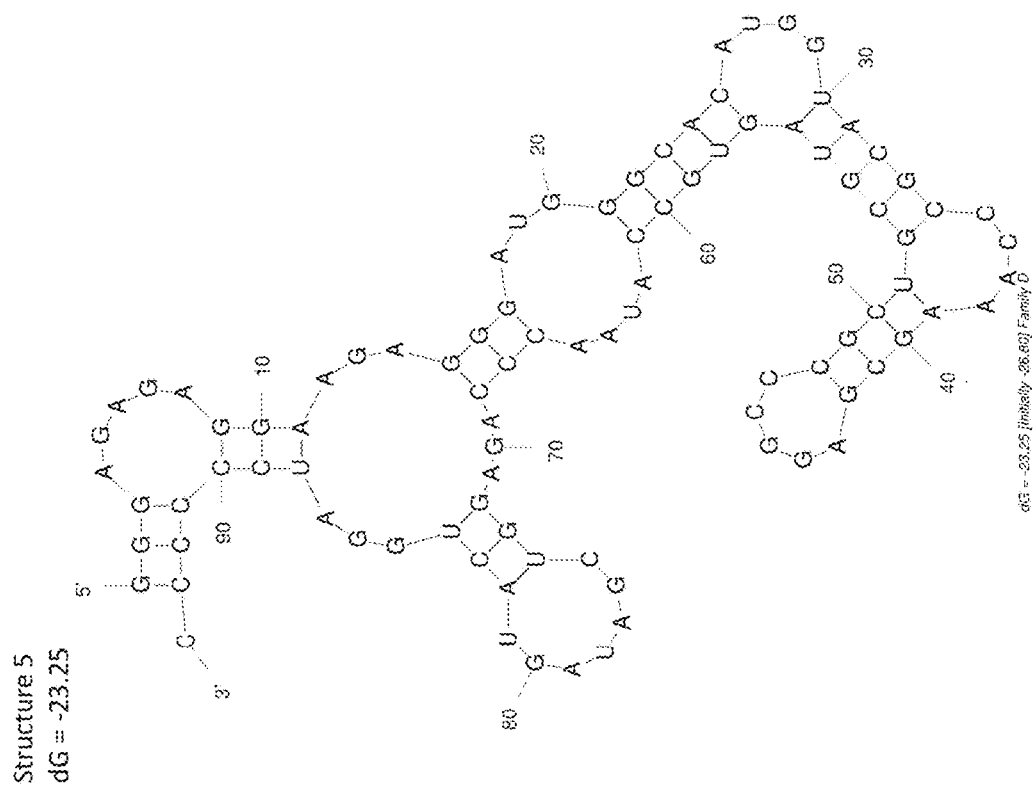
Figure 14B:
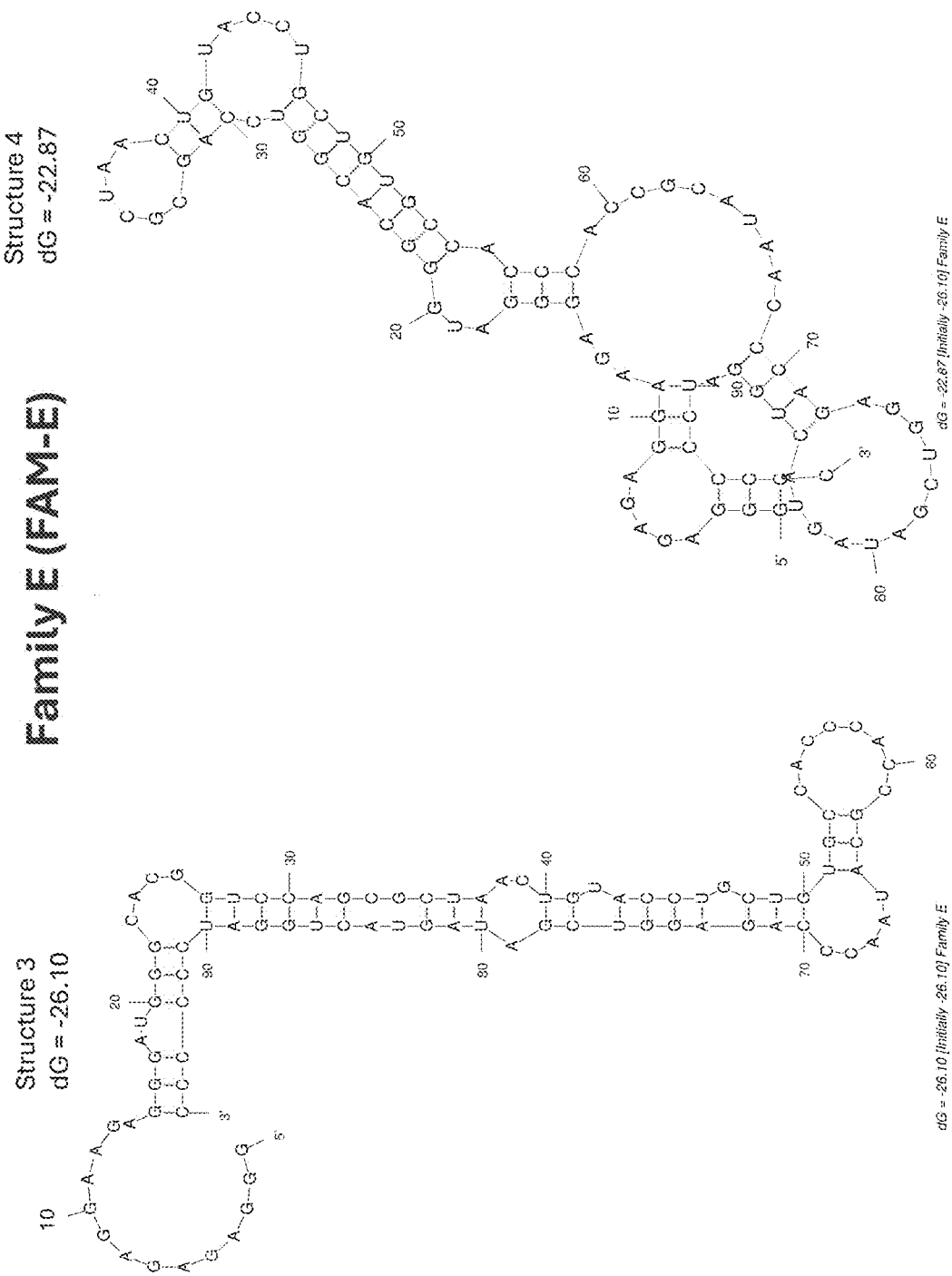
Figure 14D:
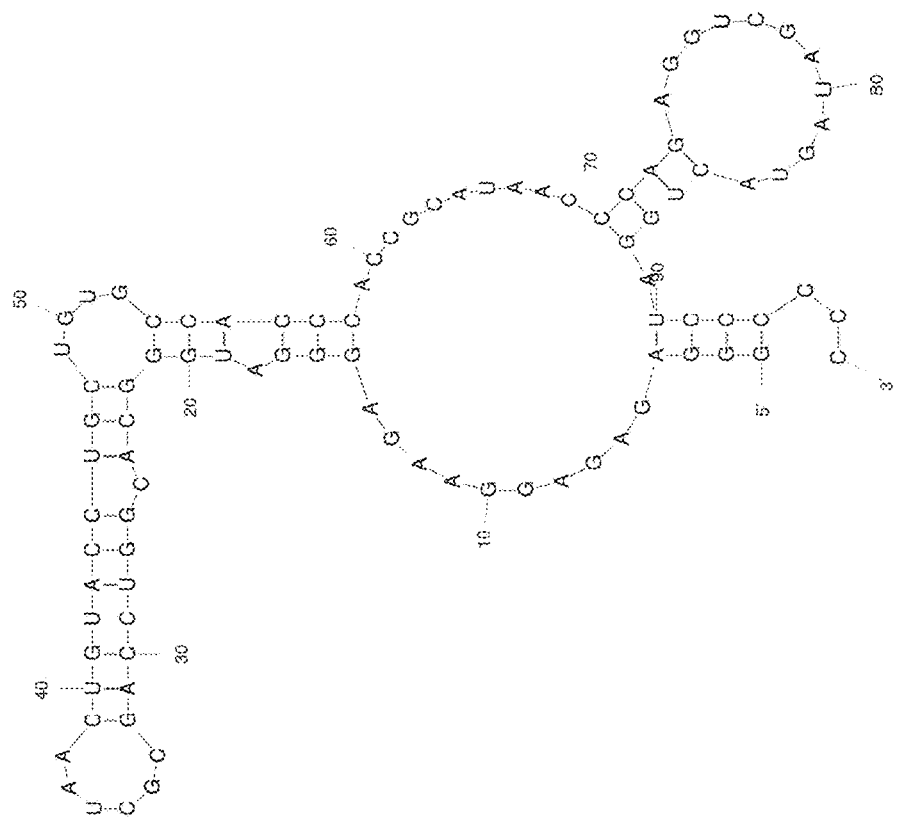
Figure 15B:
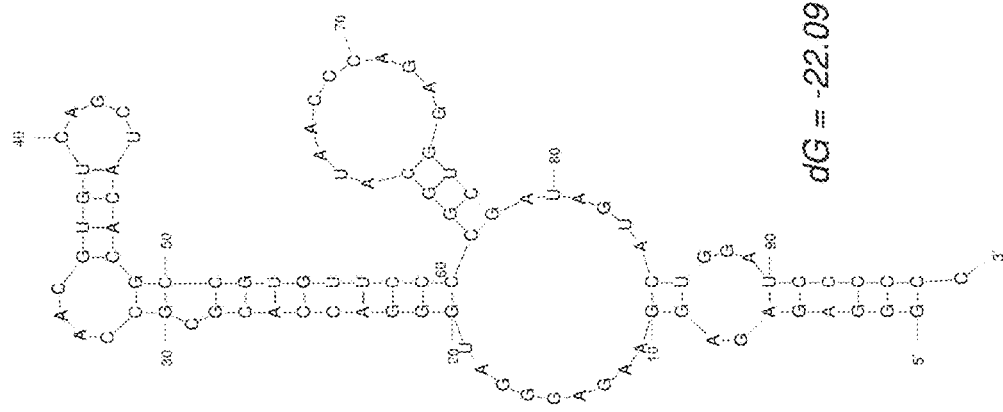
Figure 17:
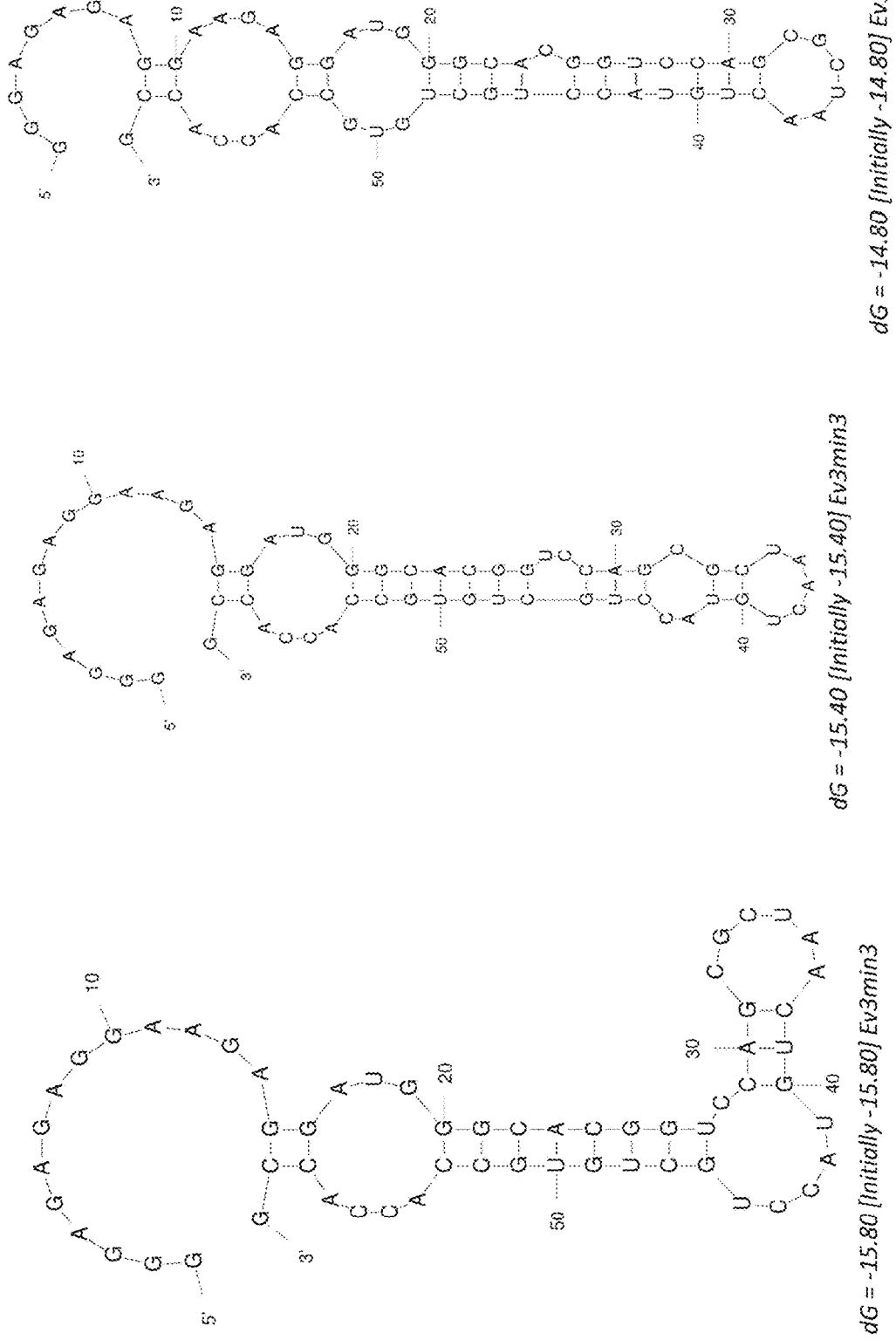
FIG. 17 shows predicted secondary structures for Ev3min3 truncate aptamer (SEQ ID NO: 498).
Figure 18:
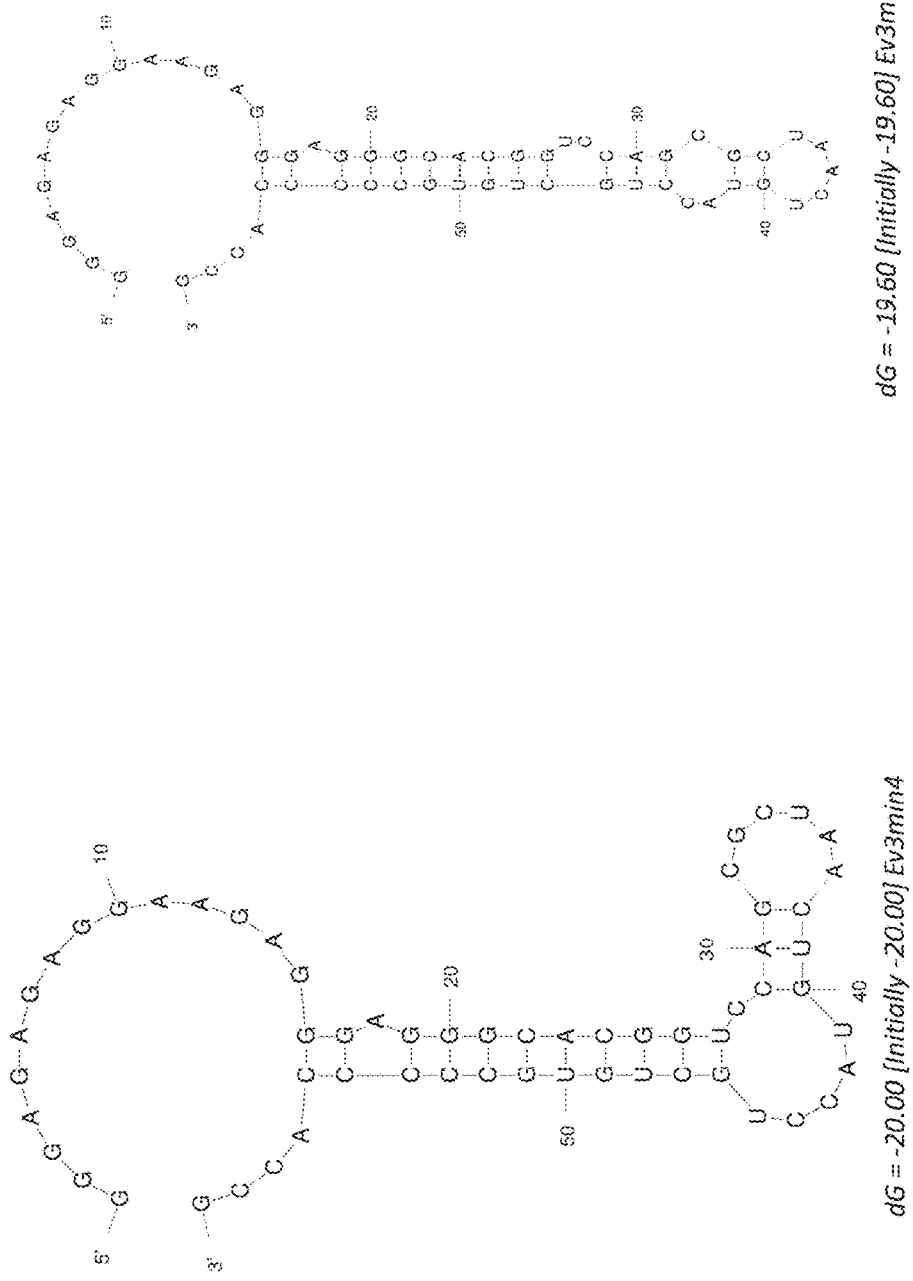
FIG. 18 shows predicted secondary structures for Ev3min4 truncate aptamer (SEQ ID NO: 499).
Figure 19:
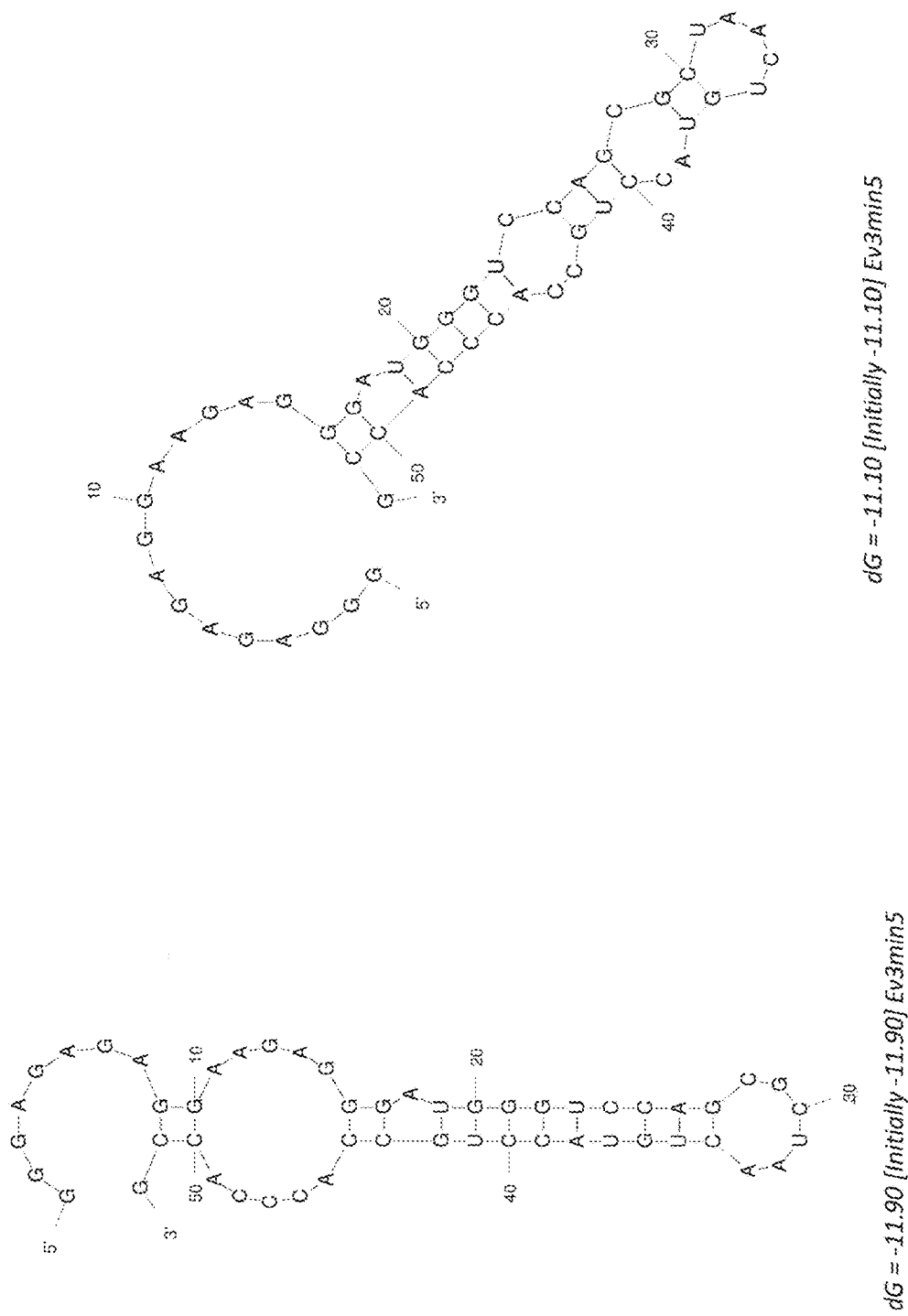
FIG. 19 shows predicted secondary structures for Ev3min5 truncate aptamer (SEQ ID NO: 500).
Figure 20:
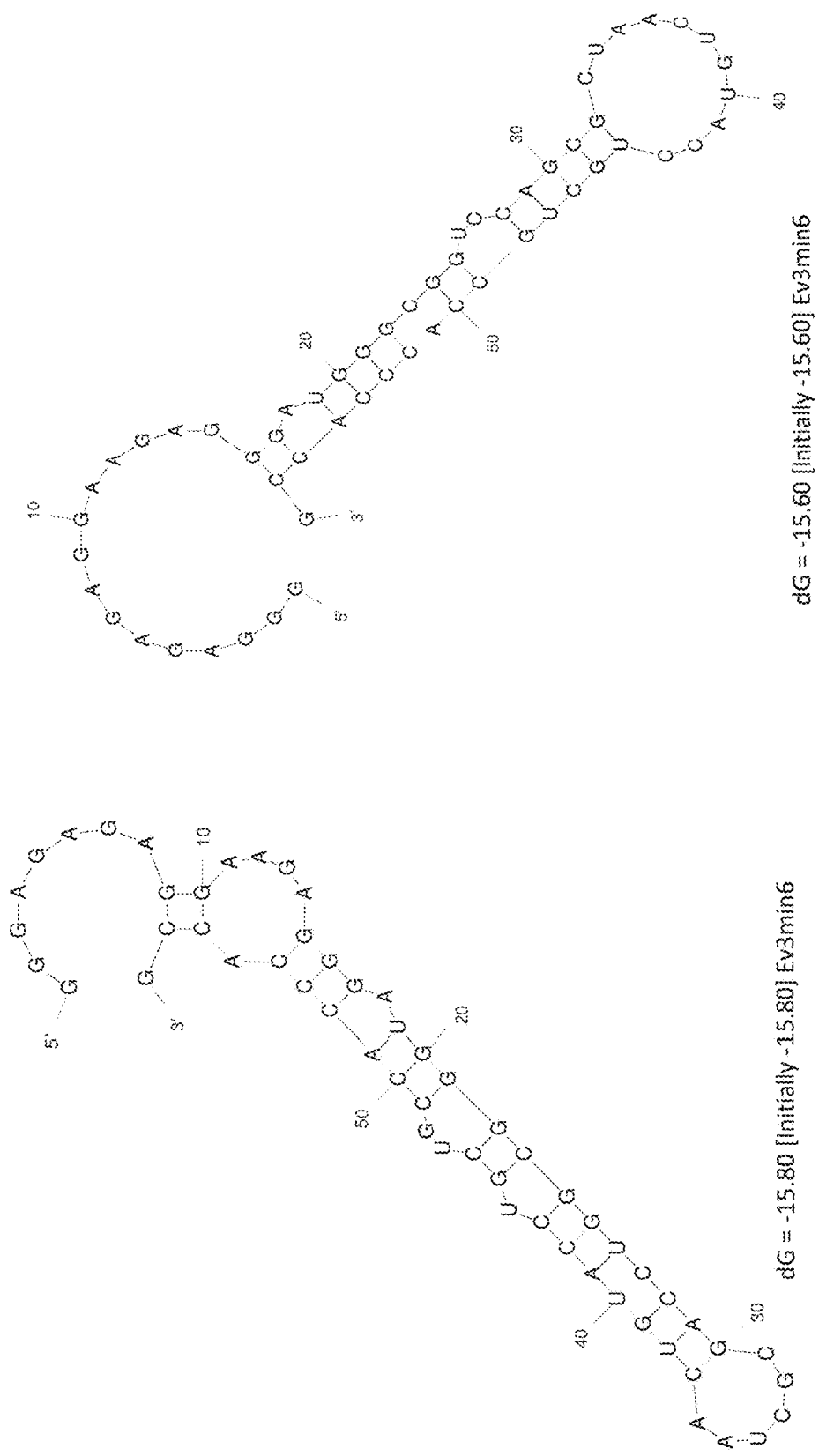
FIG. 20 shows predicted secondary structures for Ev3min6 truncate aptamer (SEQ ID NO: 501).
Figure 21:
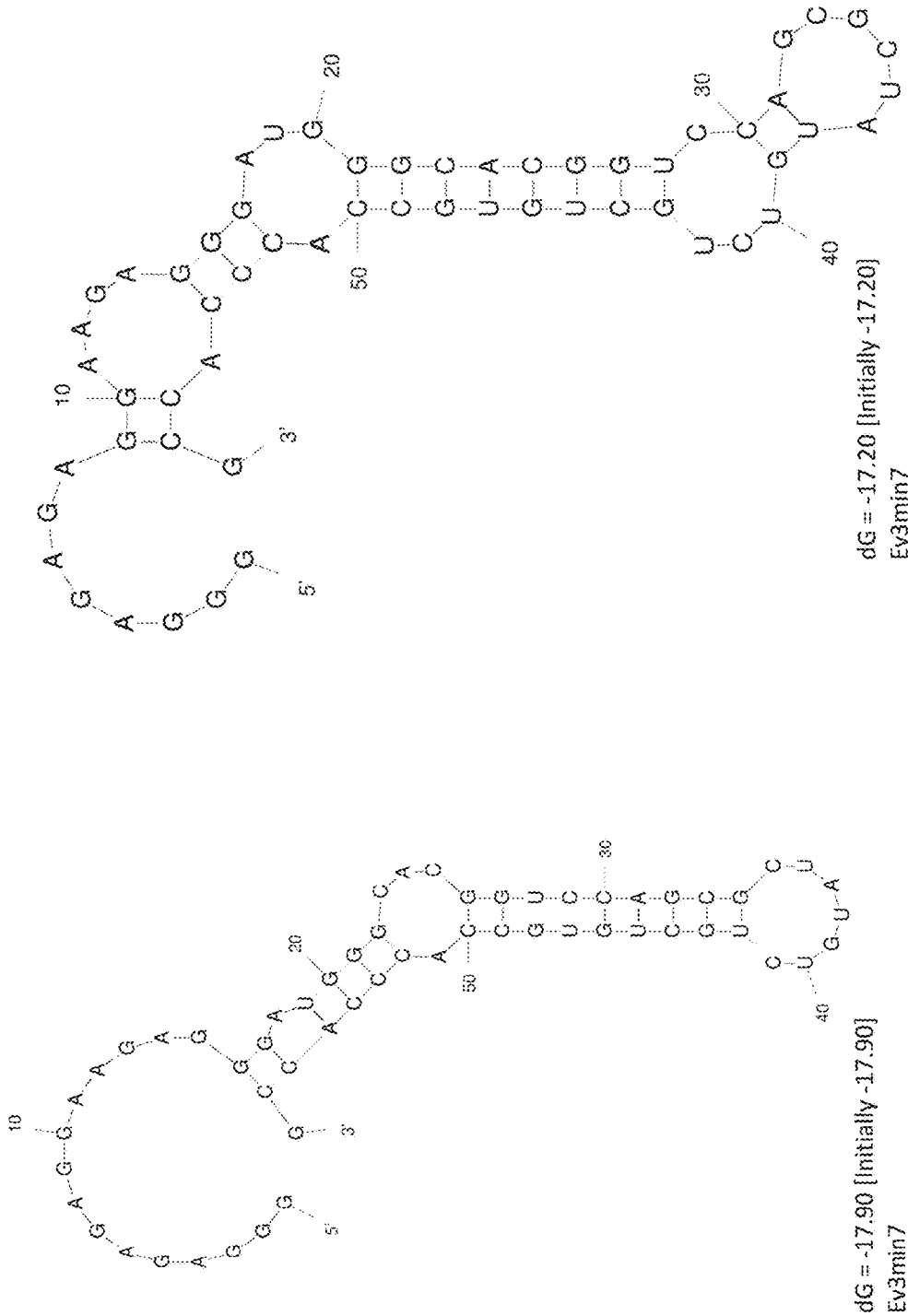
FIG. 21 shows predicted secondary structures for Ev3min7 truncate aptamer (SEQ ID NO: 502).
Figure 22:
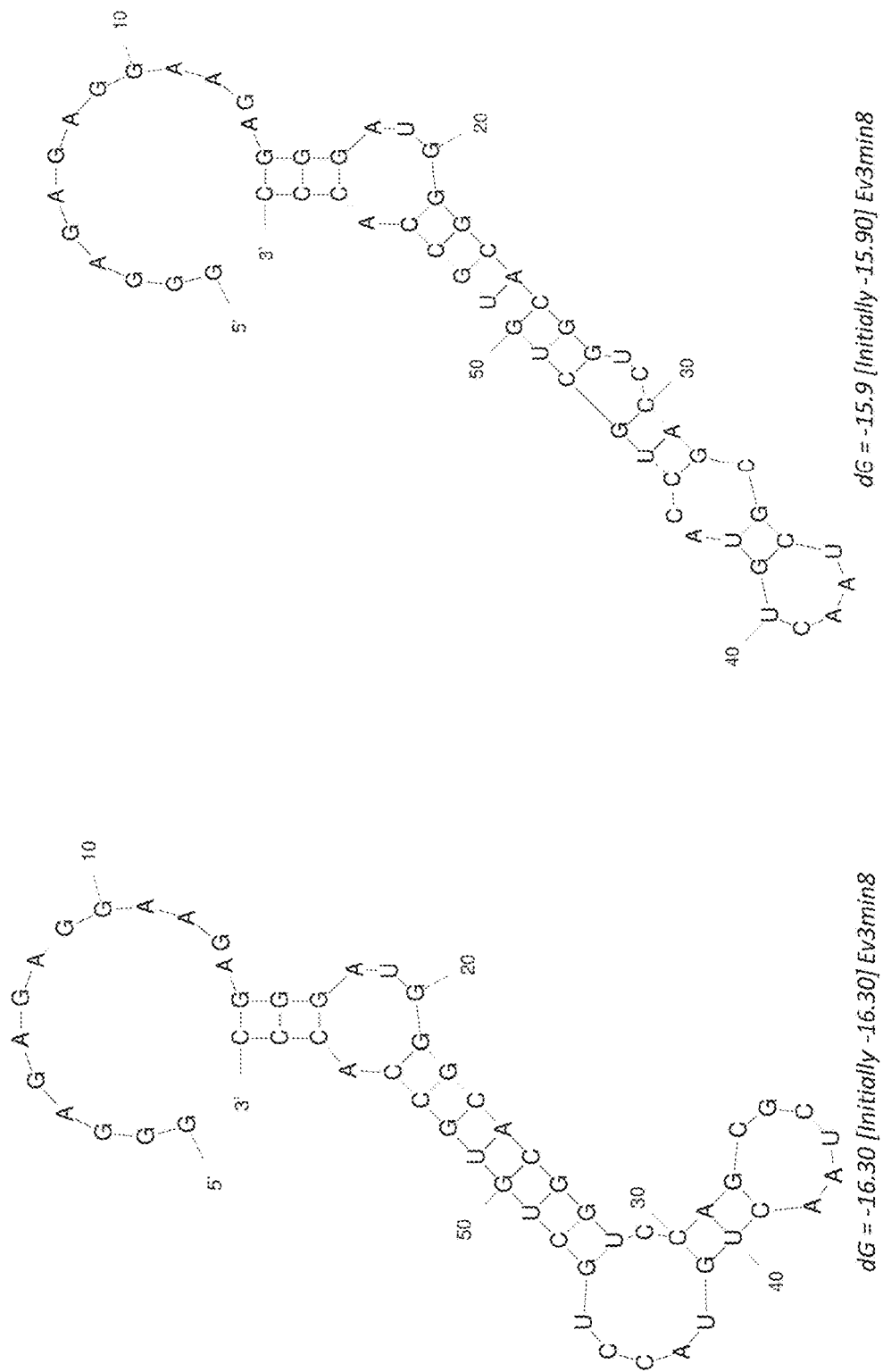
FIG. 22 shows predicted secondary structures for Ev3min8 truncate aptamer (SEQ ID NO: 503).
Figure 23:
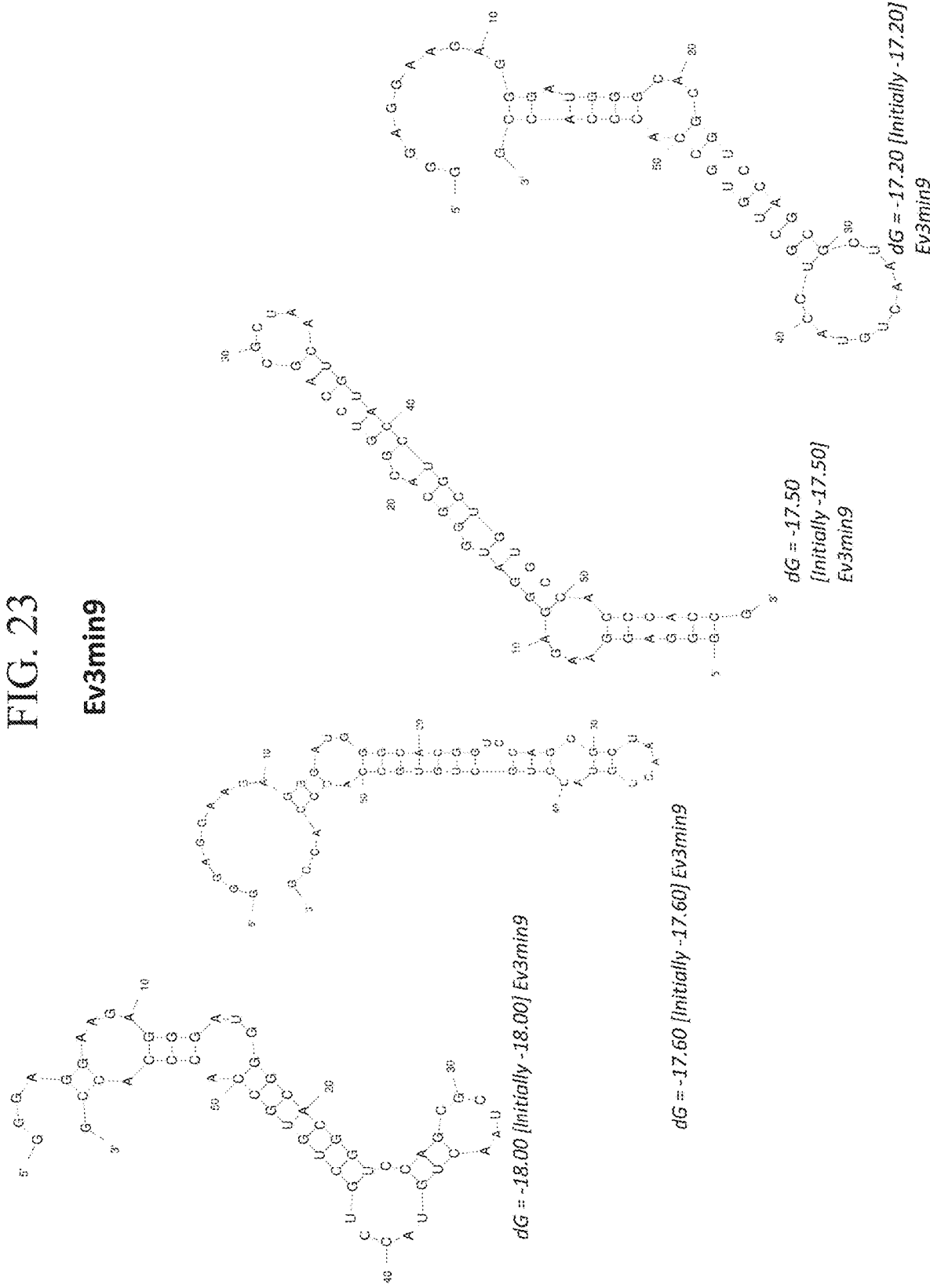
FIG. 23 shows predicted secondary structures for Ev3min9 truncate aptamer (SEQ ID NO: 504).
Figure 24:
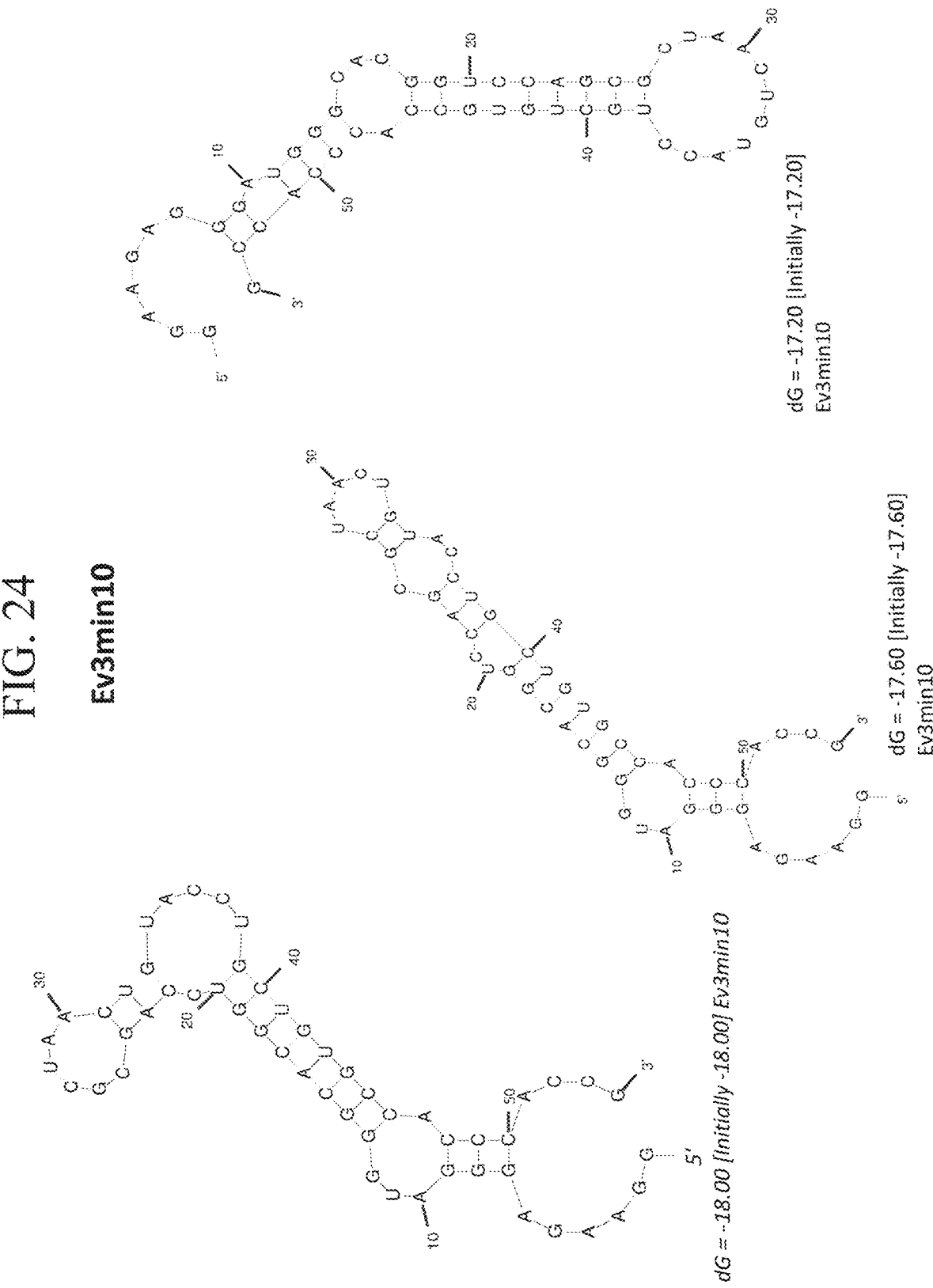
FIG. 24 shows predicted secondary structures for Ev3min10 truncate aptamer (SEQ ID NO: 505).
Figure 26:
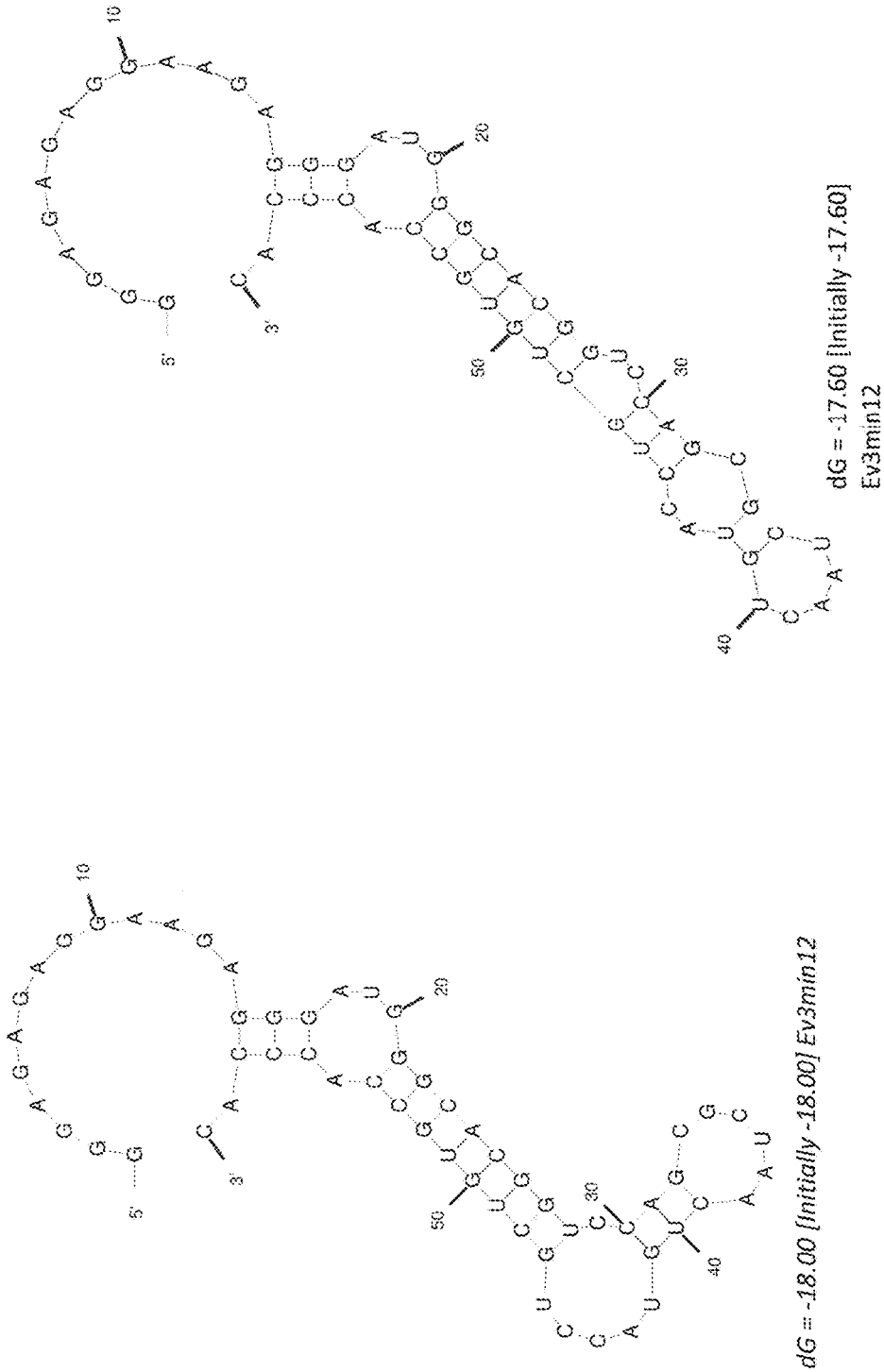
FIG. 26 shows predicted secondary structures for Ev3min12 truncate aptamer (SEQ ID NO: 507).
Figure 28B:
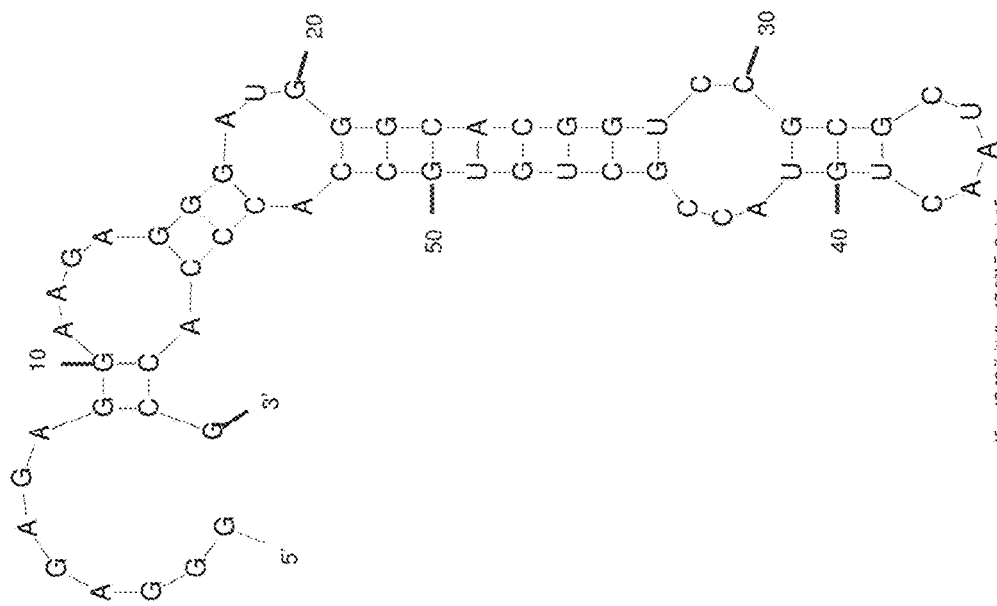
FIGS. 28A-28B show predicted secondary structures for Ev3min14 truncate aptamer (SEQ ID NO: 509) and Ev3min15 truncate aptamer (SEQ ID NO: 510).
Figure 28A:
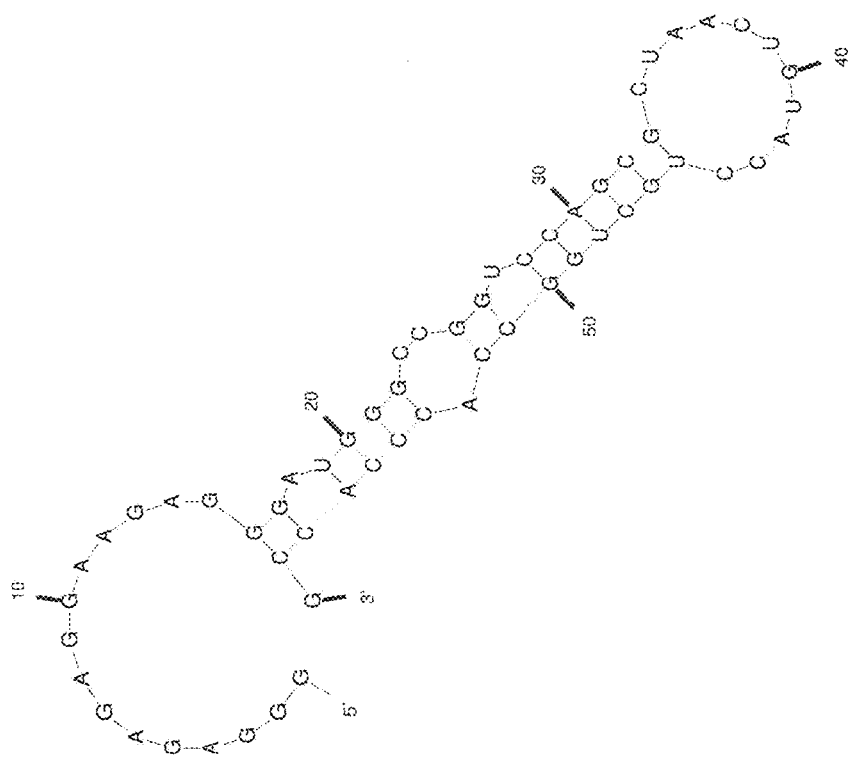
Figure 29:
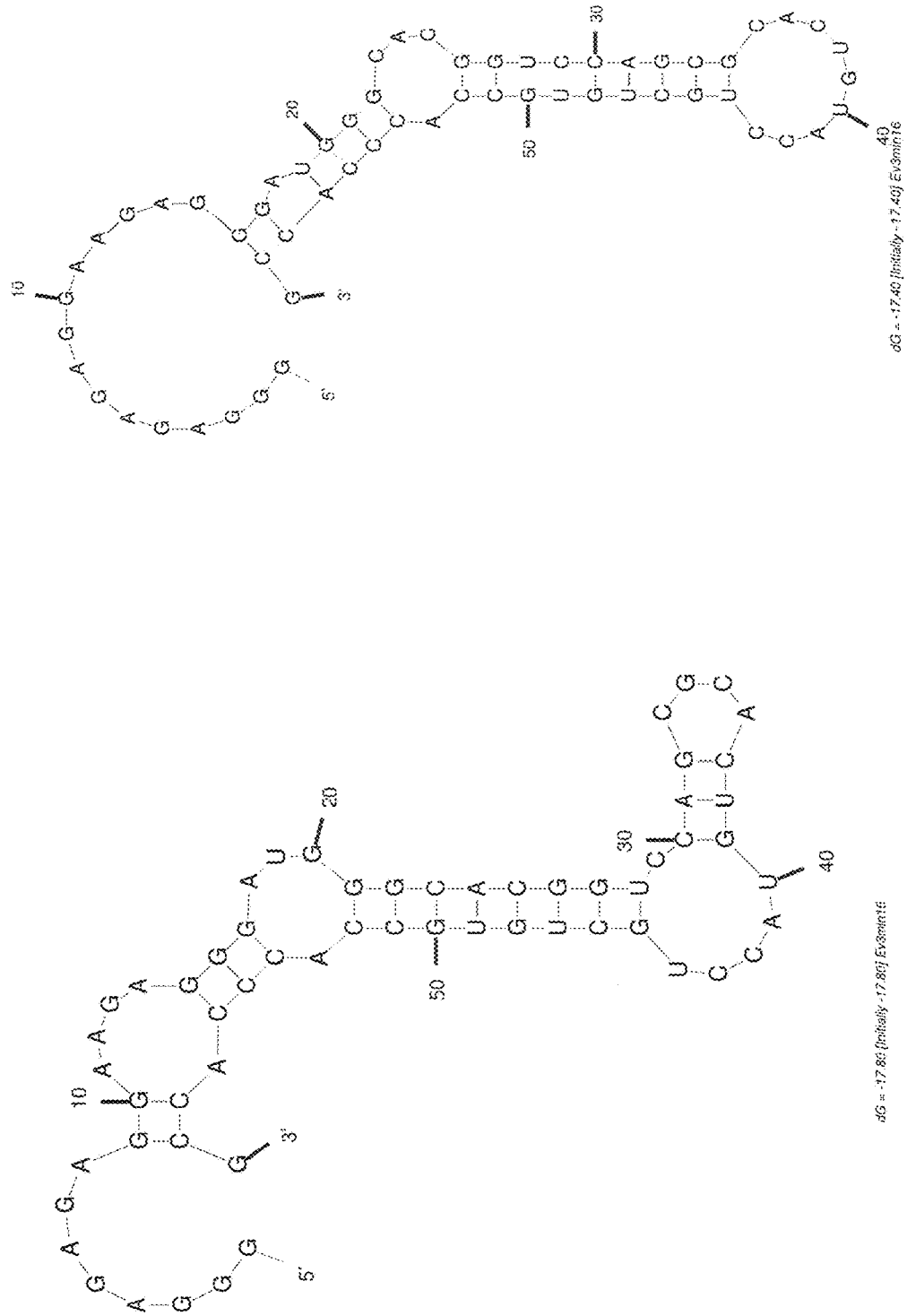
FIG. 29 shows predicted secondary structures for Ev3min16 truncate aptamer (SEQ ID NO: 511).
Figure 30:
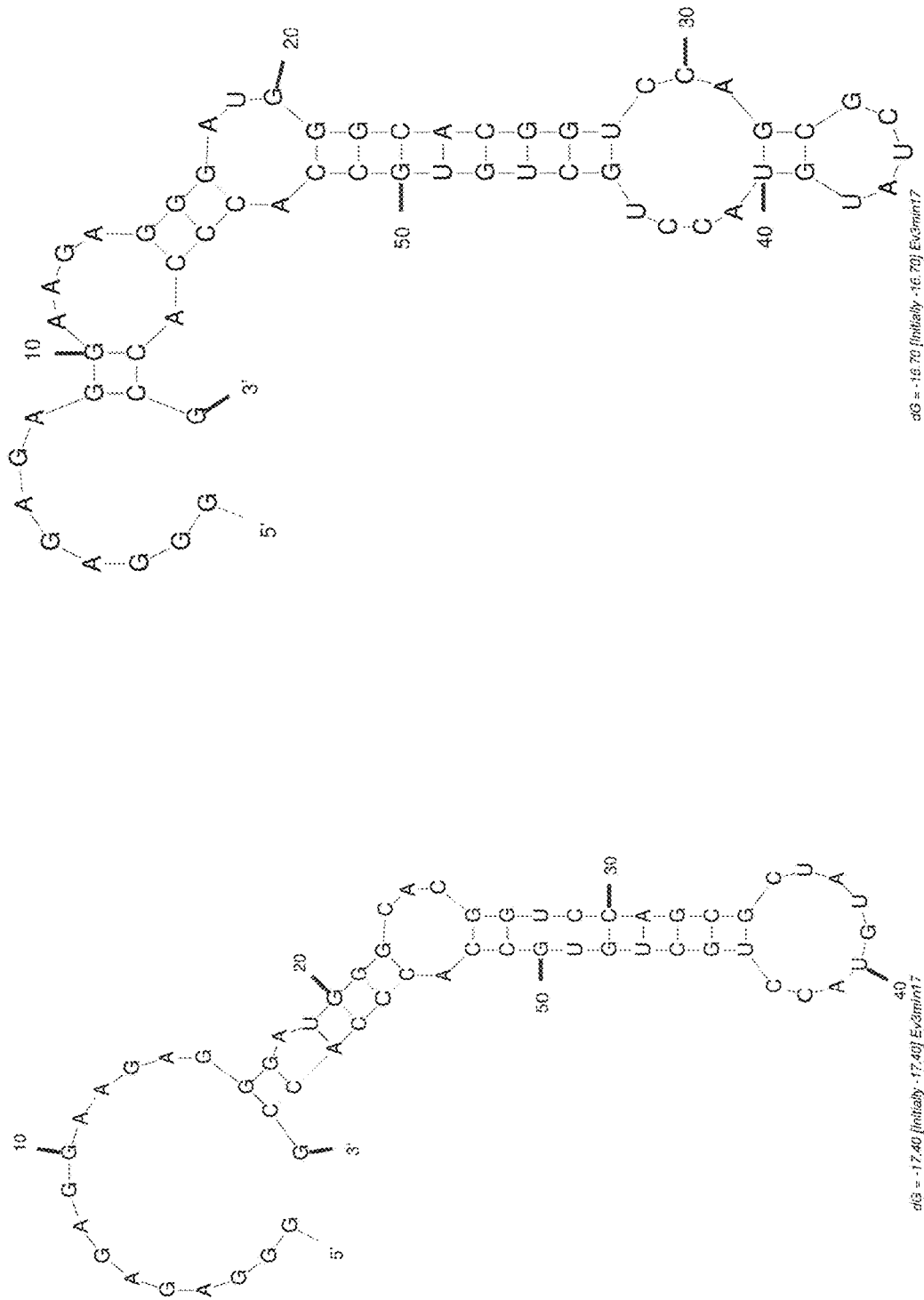
FIG. 30 shows predicted secondary structures for Ev3min17 truncate aptamer (SEQ ID NO: 512).
Figure 31:
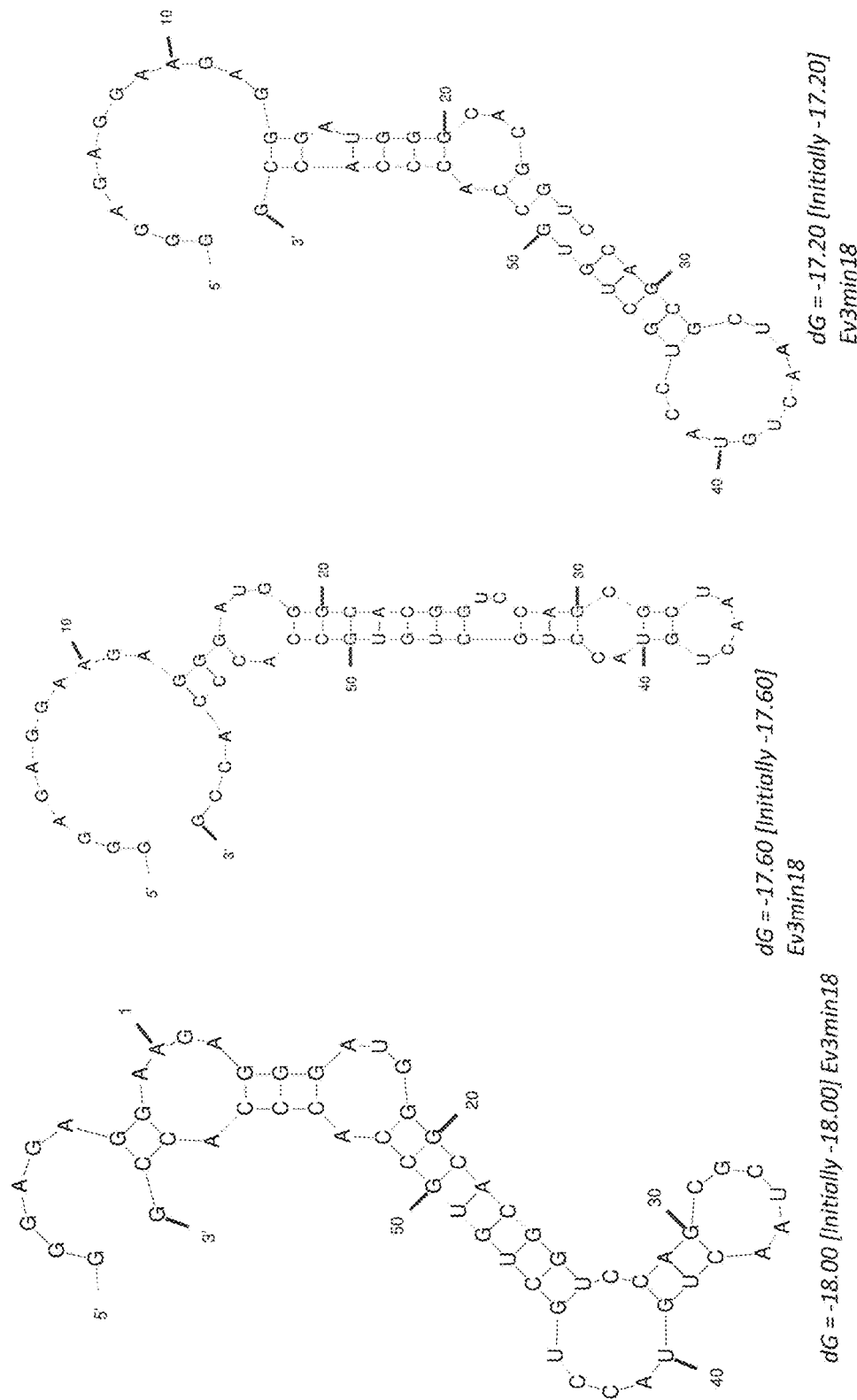
FIG. 31 shows predicted secondary structures for Ev3min18 truncate aptamer (SEQ ID NO: 513).
Figure 32:
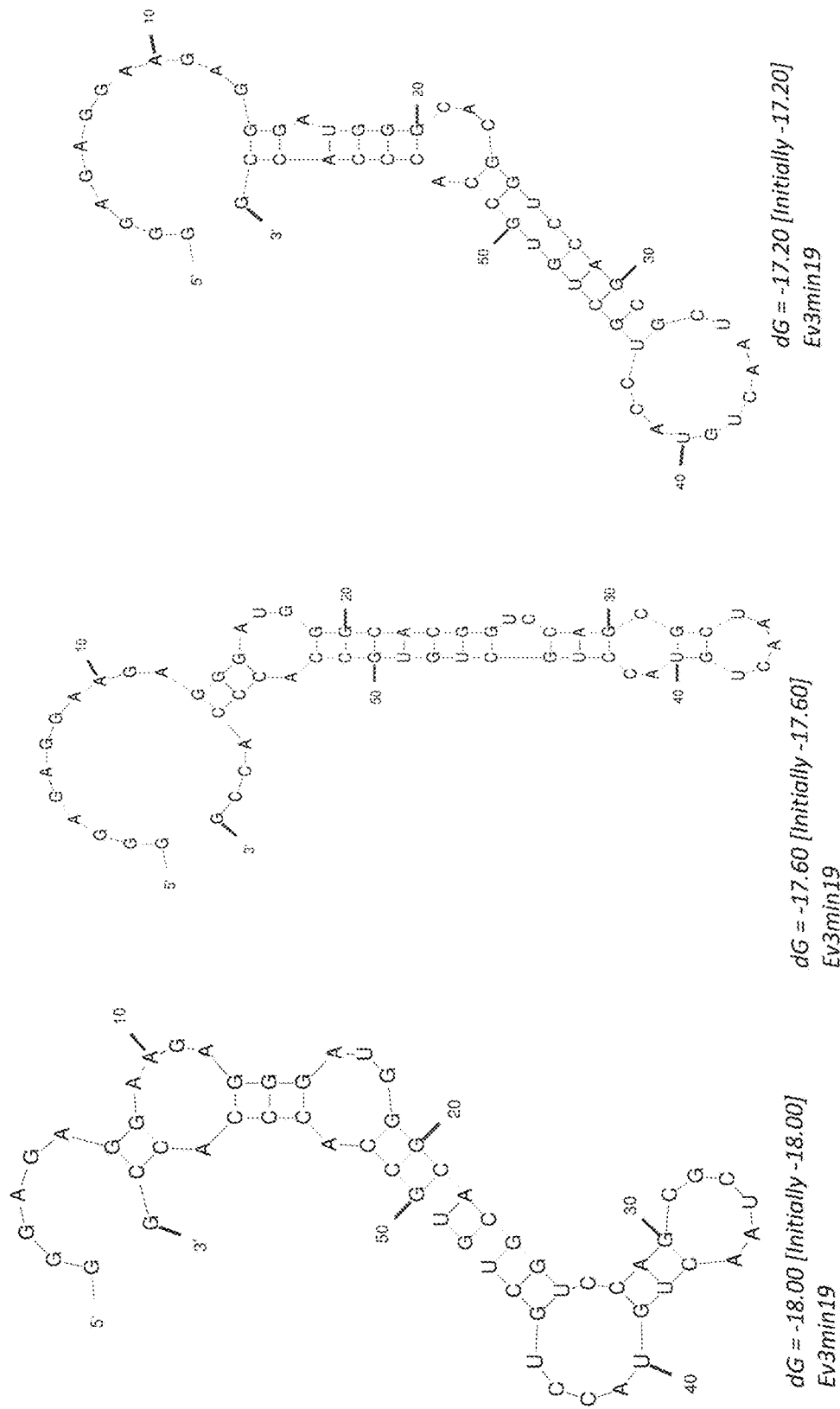
FIG. 32 shows predicted secondary structures for Ev3min19 truncate aptamer (SEQ ID NO: 514).
Figure 33:
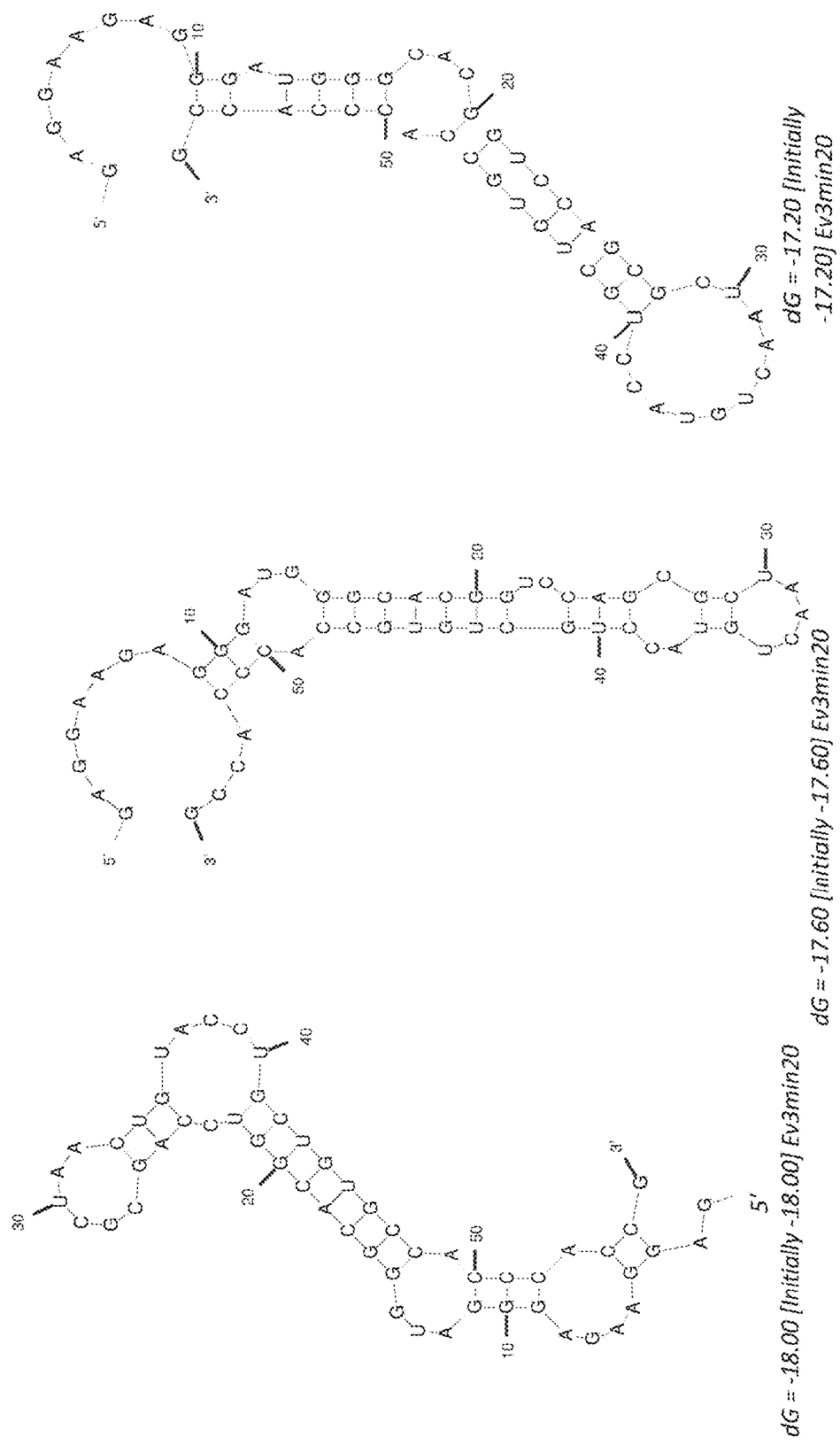
FIG. 33 shows predicted secondary structures for Ev3min20 truncate aptamer (SEQ ID NO: 515).
Figure 34:
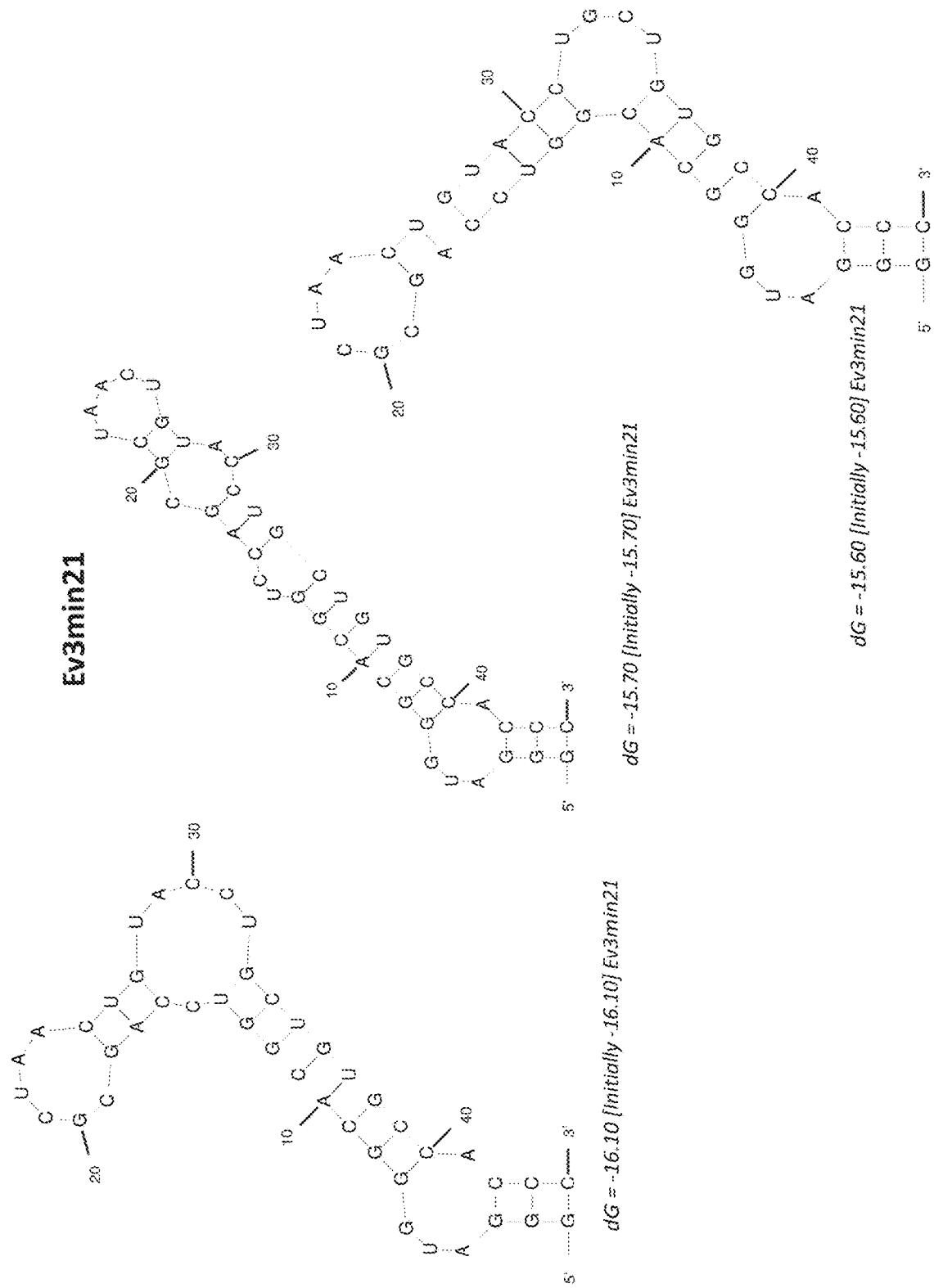
FIG. 34 shows predicted secondary structures for Ev3min21 truncate aptamer (SEQ ID NO: 486).
Figure 35:
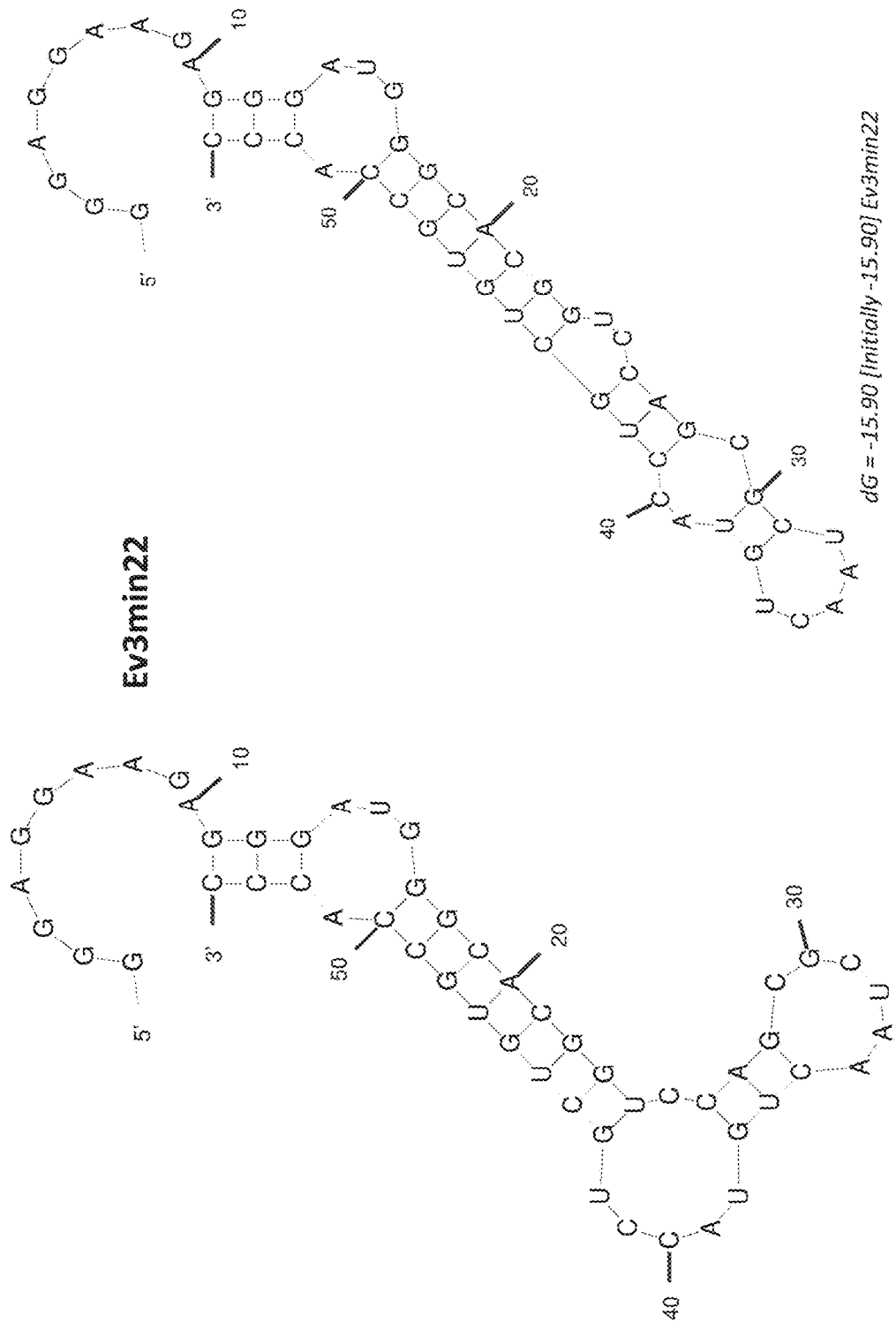
FIG. 35 shows predicted secondary structures for Ev3min22 truncate aptamer (SEQ ID NO: 487).
Figure 36:
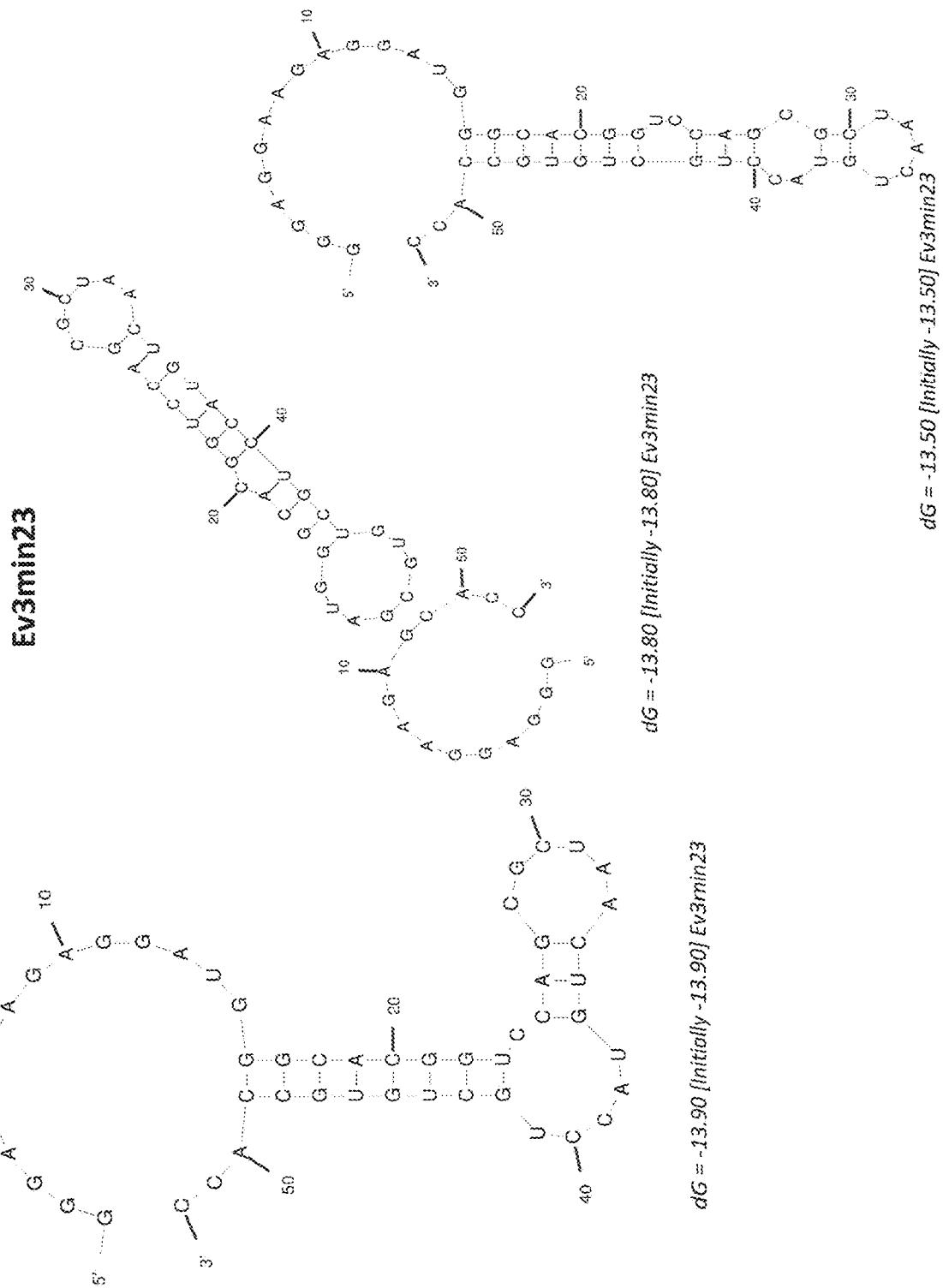
FIG. 36 shows predicted secondary structures for Ev3min23 truncate aptamer (SEQ ID NO: 488).
Figure 37A:
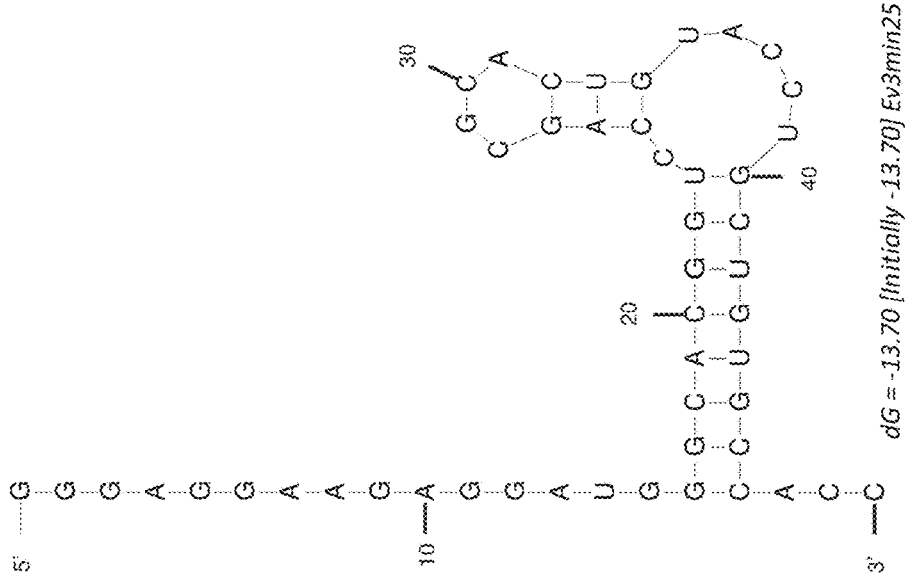
FIGS. 37A-37B show predicted secondary structures for Ev3min24 truncate aptamer (SEQ ID NO: 489) and Ev3min25 truncate aptamer (SEQ ID NO: 490).
Figure 37B:
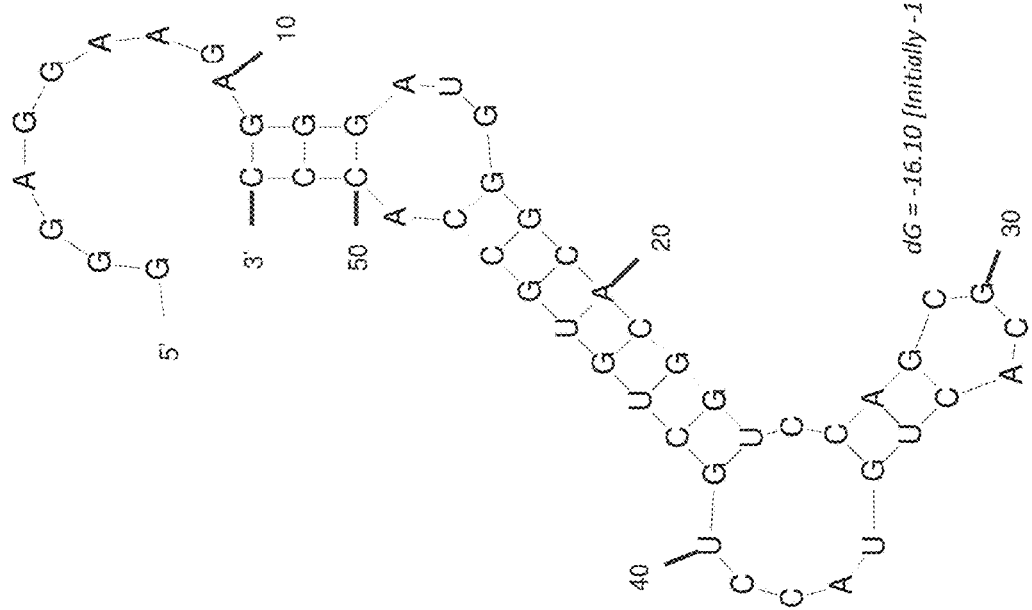

To determine whether the EV3 aptamer could be truncated without affecting its radiosensitization function, we tested some Ev3 aptamer truncates (FIG. 10). HCT 116 p53−/− colon cancer cells were treated with 5 μg of indicated full-length aptamers or Ev3 truncates and exposed to 2Gy IR 48h later. Cells were cultivated for 10d and survival was assessed by MTT assay. FIG. 10 shows truncation of Ev3 resulted in reduced activity as radiosensitizer.

The Ev3 nucleolin aptamer has the potential for clinical application as a cancer-specific radio- and chemosensitizer and could improve the current regimens of cancer therapy. Further, the aptamer can be radiolabeled for use as a DNA damaging agent that will preferentially target tumors and simultaneously blunt the ability of the tumor cell to repair the radiation damage, thus enhancing the sensitivity of the tumor to the radioisotope.

Example 3—Predicted Secondary Structures for Nucleolin Aptamers

Predicted secondary structures for nucleolin aptamers were generated using the mfold Web Server RNA Folding Form. Predicted structures for representative aptamers from families B, C, D, E, and F are shown in FIGS. 11A-11B, 12A-12B, 13A-13C, 14A-14D, and 15A-15B. Predicted structures for Ev3 truncates (Ev3.min2-25) are shown in FIGS. 16-37.

We claim:

1. An aptamer comprising a polynucleotide having at least 80% sequence identity to any one of SEQ ID NOS: 1-12, 22-473, 475-479, 481, 483-484, 486, 490-502, or 504-515, wherein the polynucleotide comprises an unmodified form or comprises a modified form comprising at least one nucleotide base modification.

2. The aptamer of claim 1, wherein the aptamer comprises a polynucleotide having at least 90% sequence identity to 5'-GGGAGAGAGGAAGAGGGAUGGG (SEQ ID NO: 491)-A Variable Region-CAUAACCCAGAGGUCGAU-AGUACUGGAUCCCCC (SEQ ID NO: 492)-3', wherein the variable region comprises any one of SEQ ID NOS: 22-473 or a portion thereof.

3. The aptamer of claim 1, wherein the dissociation constant ($K_D$) of the aptamer for a nucleolin protein is less than 100 nanomolar (nM).

4. The aptamer of claim 1, wherein the polynucleotide comprises an RNA polynucleotide.

5. The aptamer of claim 1, wherein the polynucleotide comprises a modified form comprising at least one nucleotide base modification selected from the group consisting of a 2'fluoro modification, a 2'O-methyl modification, a 5' modification, and a 3'modification.

6. The aptamer of claim 1, wherein the polynucleotide comprises a 5' linker and/or a 3' linker.

7. The aptamer of claim 1, wherein the polynucleotide further comprises an agent.

8. The aptamer of claim 7, wherein the agent is a stability agent selected from the group consisting of polyethylene glycol (PEG), cholesterol, albumin, and Elastin-like polypeptide or a reporter moiety.

9. The aptamer of claim 8, wherein said reporter moiety is selected from the group consisting of a fluorophore moiety, an optical moiety, a magnetic moiety, a radiolabel moiety, an X-ray moiety, an ultrasound imaging moiety, a photoacoustic imaging moiety, a nanoparticle-based moiety, and a combination of two or more of the reporter moieties.

10. The aptamer of claim 7, wherein the polynucleotide and the agent are linked by a covalent bond or a tag system.

11. A dimer, trimer, or tetramer comprising the aptamer of claim 1.

12. A method for treating cancer in a subject comprising administering to the subject a therapeutically effective amount of the composition of claim 1.

13. The method of claim 12, further comprising administering a chemotherapeutic agent or radiation therapy to the subject.

14. The method of claim 13, wherein the composition is administered prior to the administration of the chemotherapeutic agent or the radiation therapy.

15. The method of claim 12, wherein the cancer is colon cancer.

16. The method of claim 12, wherein the subject is a mammal.

17. A method of labeling or inhibiting nucleolin comprising contacting nucleolin with the composition of claim 1.

18. The method of claim 17, wherein the nucleolin is contacted by adding the composition to cells comprising nucleolin in vitro.

19. The method of claim 17, wherein the nucleolin is contacted by administering the composition to a subject.

* * * * *